US007420041B2

(12) United States Patent
Young et al.

(10) Patent No.: US 7,420,041 B2
(45) Date of Patent: Sep. 2, 2008

(54) CYTOTOXICITY MEDIATION OF CELLS EVIDENCING SURFACE EXPRESSION OF TROP-2

(75) Inventors: David S. F. Young, Toronto (CA); Helen P. Findlay, Toronto (CA); Susan E. Hahn, Toronto (CA); Luis A. G. DaCruz, Toronto (CA); Alison L. Ferry, Thornhill (CA)

(73) Assignee: Arius Research Inc., Toronto, Ontario (CA)

( * ) Notice: Subject to any disclaimer, the term of this patent is extended or adjusted under 35 U.S.C. 154(b) by 0 days.

(21) Appl. No.: 11/709,898

(22) Filed: Feb. 22, 2007

(65) Prior Publication Data

US 2007/0202043 A1 Aug. 30, 2007

Related U.S. Application Data

(60) Provisional application No. 60/776,466, filed on Feb. 24, 2006.

(51) Int. Cl.
*C07K 16/00* (2006.01)

(52) U.S. Cl. .............. 530/387.1; 530/387.3; 530/388.1; 530/391.3; 530/391.7; 435/326

(58) Field of Classification Search ............. 530/387.1, 530/387.3, 388.1, 391.3, 391.7; 435/326
See application file for complete search history.

(56) References Cited

U.S. PATENT DOCUMENTS

| 4,861,581 A | 8/1989 | Epstein et al. |
| 5,171,665 A | 12/1992 | Hellstrom et al. |
| 5,484,596 A | 1/1996 | Hanna, Jr. et al. |
| 5,693,763 A | 12/1997 | Codington et al. |
| 5,750,102 A | 5/1998 | Eisenbach et al. |
| 5,780,033 A | 7/1998 | Torchilin et al. |
| 5,783,186 A | 7/1998 | Arakawa et al. |
| 5,840,854 A | 11/1998 | Hellstrom et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 6,653,104 B2 | 11/2003 | Goldenberg |
| 7,238,785 B2 * | 7/2007 | Govindan et al. |
| 2004/0001825 A1 | 1/2004 | Govindan et al. |

FOREIGN PATENT DOCUMENTS

CA 2478047 9/2003

OTHER PUBLICATIONS

Faulk et al., "Antigens of Human Trophoblasts: A Working Hypothesis for their Role in Normal and Abnormal Pregnancies", Proc. Natl. Acad. Sci. USA (1978), vol. 75, No. 4, pp. 1947-1951.
Kohler et al., "Continuous Cultures of Fused Cells Secreting Antibody of Predefined Specificity", Nature (1975), vol. 256, pp. 495-497.
Basu et al., "The Epithelial/Carcinoma Antigen EGP-1, Recognized by Monoclonal Antibody RS7-3G11, is Phosphorylated on Serine 303", Int. J. Cancer (1995), vol. 62, pp. 472-479.
Fornaro et al., "Cloning of the Gene Encoding TROP-2, A Cell-surface Glycoprotein Expressed by Human Carcinomas", Int. J. Cancer (1995), vol. 62, pp. 610-618.
Fradet et al., "Cell Surface Antigens of Human Bladder Cancer Defined by Mouse Monoclonal Antibodies", Proc. Natl. Acad. Sci. USA (1984), vol. 81, pp. 224-228.
Calabrese et al., "Assignment of TACSTD1 (alias TROP1, M4S1) to Human Chromosome 2p21 and Refinement of Mapping of TACSTD2 (alias TROP2, M1S1) to Human Chromosome 1p32 by in Situ Hybridization", Cytogenet Cell Genet (2001), vol. 92, pp. 164-165.
Ripani et al., "Human TROP-2 is a Tumor-Associated Calcium Signal Transducer", Int J. Cancer (1998), vol. 76, pp. 671-676.
Santin et al., Gene Expression Profiles in Primary Ovarian Serous Papillary Tumors and Normal Ovarian Epithelium:Identification of Candidate Molecular Markets for Ovarian Cancer Diagnosis and Therapy:, Int. J. Cancer (2004), vol. 112, pp. 14-25.
Stein et al., "Murine Monoclonal Antibodies Raised against Human Non-Small Cell Carcinoma of the Lung: Specificity and Tumor Targeting", Cancer Research (1990), vol. 50, pp. 1330-1336.
Stein et al., "Radioimmunotherapy of a Human Lung Cancer Xenograft with Monoclonal Antibody RS7: Evaluation of 177 Lu and Comparison of its Efficacy with that of 90Y and Residualizing 131I", J. Nucl. Med. (2001), vol. 42, pp. 967-974.
Stein et al., "Specificity and Properties of MAb RS7-3G11 and the Antigen Defined by this Pancarcinoma Monoclonal Antibody", Int. J. Cancer (1993), vol. 55, pp. 938-946.
Stein et al., "Improved Iodine Radiolabels for Monoclonal Antibody Therapy", Cancer Research (2003), vol. 63, pp. 111-118.
Stein et al., "Characterization of Cluster 13: The Epithelial/Carcinoma Antigen Recognized by MAb RS7", Int. J. Cancer (1994), vol. 8, pp. 98-102.
Stein et al., "Comparative Biodistribution and Radioimmunotherapy of Monoclonal Antibody RS7 and its F(ab')2 in Nude Mice Bearing Human Tumor Xenografts", Cancer (1994), vol. 73, pp. 816-823.
Shih et al., "In Vitro and in Vivo Reactivity of an Internalizing Antibody, RS7, with Human Breast Cancer", Cancer Research (Suppl.) (1995), vol. 55, pp. 5857s-5863s.
Govindan et al., "Preclinical Therapy of Breast Cancer with a Radioiodinated Humanized Anti-EGP-1 Monoclonal Antibody: Advantage of a Residualizing Iodine Radiolabel", Breast Cancer Research Treatment (2004), vol. 84, pp. 173-182.
Miotti et al., "Characterization of Human Ovarian Carcinoma-Associated Antigens Defined by Novel Monoclonal Antibodies with Tumor-Restricted Specificity", Int. J. Cancer (1987), vol. 39, pp. 297-303.
Lipinski et al., "Human Trohoblast Cell-Surface Antigens Defined by Monoclonal Antibodies", Proc. Natl. Acad. Sci. USA (1981), vol. 78, pp. 5147-5150.
Nakashima et al., "Serological Identification of TROP2 By Recombinant cDNA Expression Cloning Using Sera of Patients with Esophageal Squamous Cell Carcinoma", Int. J. Cancer (2004), vol. 112, pp. 1029-1035.

* cited by examiner

*Primary Examiner*—Stephen L. Rawlings
*Assistant Examiner*—Brad Duffy
(74) *Attorney, Agent, or Firm*—McHale & Slavin, P.A.

(57) ABSTRACT

The present invention relates to a method for producing cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, cytokines, interferons, target or reporter moieties and hematogenous cells.

9 Claims, 34 Drawing Sheets

FIGURE 1

|  | Secreting ELISA | | Cytotoxicity | | | | | | IgG Binding | | |
|---|---|---|---|---|---|---|---|---|---|---|---|
|  | Fold | | OCC-1 | | OVCAR-3 | | CCD-27sk | | Fold | | |
|  | IgG | IgM | Average | CV | Average | CV | Average | CV | OCC-1 | OVCAR-3 | CCD-27sk |
| AR52A301.5 | 24.1 | 0.9 | -7 | 2 | 24 | 12 | -4 | 3 | 1.0 | 3.3 | 1.3 |
| Controls NaN₃ |  |  | 86 | 24 | 45 | 13 | 12 | 5 |  |  |  |
| Cycloheximide |  |  | 95 | 26 |  |  | 46 | 10 |  |  |  |

FIGURE 2

| | Cell Line | Pancreatic | | Breast | | Prostate | | Head & Neck | Thyroid | Esophageal | Lung | | Normals | |
| --- | --- | --- | --- | --- | --- | --- | --- | --- | --- | --- | --- | --- | --- | --- |
| | | PL45 | AsPC-1 | BxPC-3 | MDA-MB-468 | MCF-7 | PC-3 | DU-145 | FaDu | SW579 | T.Tn | NCI-H520 | A549 | CCD-27sk | Hs888.Lu |
| | AR52A301.5 | 12.9 | 1.3 | 29.4 | 22.7 | 16.0 | 5.0 | 3.9 | 59.8 | 1.4 | 18.6 | 2.1 | 1.3 | 1.2 | 2.6 |
| Positive Control | anti-EGFR | 15.8 | 15.3 | 28.4 | NA | 1.2 | 8.3 | 8.4 | NA | NA | NA | NA | 10.2 | 4.4 | 12.4 |

| | Cell Line | Ovarian | | | | | | | Colon | | | | |
| --- | --- | --- | --- | --- | --- | --- | --- | --- | --- | --- | --- | --- | --- |
| | | OV2008 | Hey | A2780-cp | A2780-s | OCC-1 | Sk-OV-3 | OVCAR-3 | C-13 | OVCA-429 | DLD-1 | Lovo | HT-29 | Colo-205 | SW1116 |
| | AR52A301.5 | 32.7 | 5.9 | 1.5 | 1.5 | 17.8 | 1.5 | 22.1 | 38.7 | 3.4 | 82.8 | 0.9 | 6.7 | 38.6 | 0.9 |
| Positive Control | anti-EGFR | 64.3 | 10.8 | 2.2 | 1.0 | 30.5 | NA | 14.8 | 19.4 | 10.9 | 60.4 | 3.8 | NA | NA | 4.9 |

FIGURE 24

| Tissue Data | | | | | AR52A301.5 | | TROP-2 | | Actin | | IgG negative control | |
|---|---|---|---|---|---|---|---|---|---|---|---|---|
| Tissue Type | Age | Sex | Diagnosis | Tissue ID | Tissue specificity | Section score | Tissue specificity | Section score | Tissue specificity | Section score | Section score | Tissue specificity |
| Ovary | 37 | F | Normal | HT01136 | Endothelium of blood vessels | +/- | Endothelium of blood vessels | +/- | Ovarian stroma | ++ | - | - |
| Pancreas | 62 | M | Normal | HT01137 | Acinar and ductal epithelium | +++ | Acinar and ductal epithelium | +++ | SMF of blood vessels | +++ | - | - |
| Thyroid | 62 | M | Normal | HT01138 | Follicular epithelium | ++ | Follicular epithelium | ++ | SMF of blood vessels | +++ | - | - |
| Brain, Cerebrum | 70 | F | Normal | HT01139 | - | - | Neural cells | +* | - | -* | -* | - |
| Brain, Cerebellum | 26 | M | Normal | HT01140 | - | - | Neural cells | + | Neural tissue | +* | - | - |
| Lung | 83 | F | Normal | HT01141 | Alveolar epithelium | +++ | Alveolar epithelium | +++ | SMF of blood vessels | +++ | -** | - |
| Spleen | 24 | M | Normal | HT01142 | Sinusoidal endothelium and Lymphoid tissue | +/- | - | - | SMF of blood vessels | ++ | -*** | - |
| Uterus | 47 | F | Normal | HT01143 | Endothelium of blood vessels | +/- | - | - | SMF | +++ | - | - |
| Cervix | 49 | F | Normal | HT01144 | Endothelium of blood vessels | + | - | - | SMF of blood vessels | ++ | - | - |
| Heart | 19 | F | Normal | HT01147 | Endothelium of blood vessels | +/- | Endothelium of blood vessels | +/- | Cardiac muscle fibers | +++ | - | - |
| Skin | 21 | F | Normal | HT01148 | Epidermal keratinocyte | ++ | Epidermal keratinocyte | +++ | SMF of blood vessels | ++ | - | - |
| Skeletal Muscle | 26 | M | Normal | HT01149 | - | - | Endothelium of blood vessels | +/- | Skeletal muscle fibers | ++ | - | - |

Legend: Negative staining: -; Equivocal staining: +/-; Weak staining: +; Moderate staining: ++; Strong staining: +++; Background staining of interstitial blood vessels: *; Background of interstitial cells: ; Extra cellular artifacts: *; SMF: smooth muscle fibers.

| Tissue | Total | IHC Score | | | | | Total positive (++,+++) | Total Weak (+/-,+) |
|---|---|---|---|---|---|---|---|---|
| | | - | +/- | + | ++ | +++ | | |
| Colon Cancer | 8 | 1 | 2 | 1 | 1 | 3 | 4/8 (50%) | 3/8 (38%) |
| Ovarian Cancer | 9 | 1 | 0 | 1 | 2 | 5 | 7/9 (78%) | 1/9 (11%) |
| Normal Ovary | 2 | 2 | 0 | 0 | 0 | 0 | 0 | 0 |
| Breast Cancer | 10 | 0 | 0 | 3 | 4 | 3 | 7/10 (70%) | 3/10 (30%) |
| Normal Breast | 3 | 1 | 0 | 0 | 2 | 0 | 2/3 (67%) | 0 |
| Lung Cancer | 9 | 0 | 0 | 3 | 2 | 4 | 6/9 (67%) | 3/9 (33%) |
| Normal Lung | 2 | 0 | 0 | 1 | 0 | 1 | 1/2 (50%) | 1/2 (50%) |
| Prostate Cancer | 13 | 1 | 0 | 0 | 3 | 9 | 12/13 (92%) | 0 |
| Normal Prostate | 3 | 0 | 0 | 0 | 0 | 3 | 3/3 (100%) | 0 |
| Pancreatic Cancer | 13 | 10 | 0 | 1 | 2 | 0 | 2/13 (15%) | 1/13 (8%) |
| Normal Pancreas | 4 | 0 | 1 | 3 | 0 | 0 | 0 | 4/4 (100%) |

| Species | Liver | Kidney | Heart | Lung | Pancreas | Brain | Skin | Colon | Spleen | Thyroid | Ovary | Testis |
|---|---|---|---|---|---|---|---|---|---|---|---|---|
| Human | ++ (Bile ducts epithelium) | ++ (Tubular epithelium) | - | +++ (Alveolar and bronchial epithelium) | +++ (Acinar and ductal epithelium) | +/- (Neural tissue) | +++ (Epidermal keratinocytes, sweat glands, sebaceous glands and hair follicle epithelium) | - | +/- (Sinusoidal epithelium) | - | ++ (Follicular epithelium) | - |
| Cynomolgus | + (Bile duct epithelium) | +++ (Tubular epithelium) | - | +++ (Alveolar and bronchial epithelium) | +++ (Ductal and acinar epithelium) | - | +++ (Epidermal keratinocytes, sweat glands, sebaceous glands and hair follicle epithelium) | - | - | +/- (Follicular epithelium) | - | - |
| Rabbit | - | - | - | - | | | | | | | | |
| Rhesus | ++ (Bile duct epithelium) | +++ (Tubular epithelium) | - | +++ (Alveolar and bronchial epithelium) | | | | | | | | |
| Mouse | NT | | - | - | - | NT | | | | | | |
| Rat | - | - | - | - | - | - | | | +/- | | | |
| Guinea pig | NT | | | - | | - | | | | | | |
| Goat | - | | - | - | | - | | | | | | |
| Sheep | NT | | | - | | - | | | | | | |
| Hamster | NT | | | - | | NT | | | | | | |
| Chicken | - | | | | | - | | | | | | |
| Bovine (Cow) | - | | - | | | - | | | | | | |
| Horse | NT | | | | | - | | | | | | |
| Dog | NT | | | | | ++ | | | | | | |
| Porcine (pig) | NT | | - | - | - | - | | - | - | | | - |
| Female and male SCID | - | - | - | - | - | | | | | | | |

NT: Tissue detached

FIGURE 30

| Antitope Code | Sequence | Length | Name-Pool |
|---|---|---|---|
| OL001 | CGCCAGGGTTTTCCCAGTCACGAC | 24 | M13/pUC for |
| OL002 | AGCGGATAACAATTTCACACAGGA | 24 | M13/pUC rev |
| OL007 | ATGRASTTSKGGYTMARCTKGRTTT | 25 | MuIgV$_H$5'-A |
| OL008 | ATGRAATGSASCTGGGTYWTYCTCTT | 26 | MuIgV$_H$5'-B |
| OL009 | ATGGACTCCAGGCTCAATTTAGTTTTCCT | 29 | MuIgV$_H$5'-C |
| OL010 | ATGGCTGTCYTRGBCTGYTCYTCTG | 26 | MuIgV$_H$5'-C |
| OL011 | ATGGVTTGGSTGTGGAMCTTGCYATTCCT | 29 | MuIgV$_H$5'-C |
| OL012 | ATGAAATGCAGCTGGRTYATSTTCTT | 26 | MuIgV$_H$5'-D |
| OL013 | ATGGRCAGRCTTACWTYYTCATTCCT | 26 | MuIgV$_H$5'-D |
| OL014 | ATGATGGTGTTAAGTCTTCTGTACCT | 26 | MuIgV$_H$5'-D |
| OL015 | ATGGGATGGAGCTRTATCATSYTCTT | 26 | MuIgV$_H$5'-E |
| OL016 | ATGAAGWTGTGGBTRAACTGGRT | 23 | MuIgV$_H$5'-E |
| OL017 | ATGGRATGGASCKKIRTCTTTMTCT | 25 | MuIgV$_H$5'-E |
| OL018 | ATGAACTTYGGGYTSAGMTTGRTTT | 25 | MuIgV$_H$5'-F |
| OL019 | ATGTACTTGGGACTGAGCTGTGTAT | 25 | MuIgV$_H$5'-F |
| OL020 | ATGAGAGTGCTGATTCTTTTGTG | 23 | MuIgV$_H$5'-F |
| OL021 | ATGGATTTTGGGCTGATTTTTTTATTG | 28 | MuIgV$_H$5'-F |
| OL022 | ACGAGGGGGAAGACATTTGGGAA | 23 | MuIgMV$_H$3'-1 |
| OL023 | CCAGGGRCCARKGGATARACIGRTGG | 26 | MuIgGV$_H$3'-2 |
| OL024 | ATGRAGWCACAKWCYCAGGTCTTT | 24 | MuIgkV$_L$5'-A |
| OL025 | ATGGAGACAGACACACTCCTGCTAT | 25 | MuIgkV$_L$5'-B |
| OL026 | ATGGAGWCAGACACACTSCTGYTATGGGT | 29 | MuIgkV$_L$5'-C |
| OL027 | ATGAGGRCCCCTGCTCAGWTTYTTGGIWTCTT | 32 | MuIgkV$_L$5'-D |
| OL028 | ATGGGCWTCAAGATGRAGTCACAKWYYCWGG | 31 | MuIgkV$_L$5'-D |
| OL029 | ATGAGTGTGCYCACTCAGGTCCTGGSGTT | 29 | MuIgkV$_L$5'-E |
| OL030 | ATGTGGGGAYCGKTTTYAMMCTTTTCAATTG | 31 | MuIgkV$_L$5'-E |
| OL031 | ATGGAAGCCCCAGCTCAGCTTCTCTTCC | 28 | MuIgkV$_L$5'-E |
| OL032 | ATGAGIMMKTCIMTTCAITTCYTGGG | 26 | MuIgkV$_L$5'-F |
| OL033 | ATGAKGTHCYCIGCTCAGYTYCTIRG | 26 | MuIgkV$_L$5'-F |
| OL034 | ATGGTRTCCWCASCTCAGTTCCTTG | 25 | MuIgkV$_L$5'-F |
| OL035 | ATGTATATATGTTTGTTGTCTATTTCT | 27 | MuIgkV$_L$5'-F |
| OL036 | ATGAAGTTGCCTGTTAGGCTGTTGGTGCT | 29 | MuIgkV$_L$5'-G |
| OL037 | ATGGATTTWCARGTGCAGATTWTCAGCTT | 29 | MuIgkV$_L$5'-G |
| OL038 | ATGGTYCTYATVTCCTTGCTGTTCTGG | 27 | MuIgkV$_L$5'-G |
| OL039 | ATGGTYCTYATVTTRCTGCTGCTATGG | 27 | MuIgkV$_L$5'-G |
| OL040 | ACTGGATGGTGGGAAGATGGA | 21 | MuIgkV$_L$3'-1 |
| OL041 | ATGGCCTGGAYTYCWCTYWTMYTCT | 25 | MuIgλV$_L$5'-A |
| OL042 | AGCTCYTCWGWGGAIGGYGGRAA | 23 | MuIgλV$_L$3'-1 |

FIGURE 33

```
         10        20      7abcde  30          40
    DVVMTQTPLSLPVSLGDQASISCRSSQSLVHSYGNTYLHWYLQKPGQSPK 50        60         70         80         90
    LLIYKVSNRFSGVPDRFSGSGSGTDFTLKISRVEAEDMGVYFCSQSTHV-

100
    YTFGGGTKLEIK
```

FIGURE 34

```
        10         20         30         40         50
EVQLQQSGPELVKPGASVKISCKASGYTFTDYNMHWVKQSHGKSLEWIGY 2a         60         70         80 2abc        90
IYPYNGGTGYNQRFKNKATLTVDISSSTAYMELRSLTSEDSAVYYCAREE 100a       110
DYYGFDYWGQGTTLTVSS
```

CYTOTOXICITY MEDIATION OF CELLS EVIDENCING SURFACE EXPRESSION OF TROP-2

REFERENCE TO RELATED APPLICATIONS

This application claims benefit of the filing date of Provisional Application 60/776,466, filed on Feb. 24, 2006, the contents of which are herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMAB of the instant invention.

BACKGROUND OF THE INVENTION

TROP-2 is a cell surface glycoprotein expressed on most carcinomas, as well as some normal human tissues. It was initially defined as a molecule recognized by two murine monoclonal antibodies raised to a human choriocarcinoma cell line BeWo that recognized an antigen on human trophoblast cells (Faulk 1978). The same molecule was independently discovered by other investigators which led to multiple names describing the same antigen. Hence, TROP-2 was also referred to as GA733-1 and epithelial glycoprotein-1 (EGP-1) (Basu 1995, Fornaro 1995).

The TROP-2 gene is an intronless gene that was thought to have been formed through the retroposition of a homologous gene GA 733-2 (also known as epithelial glycoprotein-2, EpCAM and Trop-1) via an RNA intermediate. The TROP-2 gene has been mapped to chromosome 1p32 (Calabrese 2001). The protein component of TROP-2 has a molecular mass of approximately 35 kilodaltons. Its mass may be increased by 11-13 kilodaltons with heterogeneous N-linked glycosylation of its extracellular domain. There are many cysteine residues in the extracellular domain which could form disulfide bridge sites. TROP-2 is a substrate for protein kinase C, a $Ca^{2+}$ dependent protein kinase and the intracellular serine 303 residue has been shown to be phosphorylated (Basu 1995). It has also been shown that crossing-linking of TROP-2 with anti-TROP-2 antibodies transduced a calcium signal as shown by a rise in cytoplasmic $Ca^{2+}$ (Ripani 1998). These data support signal transduction as a physiological function of TROP-2, although to date no physiological ligand has been identified. Recently an association between TROP-2 expression and cancer has been shown as TROP-2 was identified as a member of a group of genes reported to be the most highly overexpressed in ovarian serous papillary carcinoma compared to normal ovarian epithelium in a large-scale gene expression analysis using cDNA microarray technology (Santin 2004).

The expression profile of TROP-2 has been elucidated through immunohistochemistry (IHC) and flow cytometery studies using many different TROP-2 antibodies. Anti-TROP-2 antibodies 162-25.3 and 162-46.2 were produced through immunization of mice with the human choriocarcinoma cell line BeWo, and were investigated for their reactivity to a series of tumor and lymphoid cell lines and peripheral blood mononuclear cells. In this study both antibodies appeared to be trophoblast specific, staining 3 of the 4 choriocarcinoma cell lines tested, while none of the other lymphoid or tumor cell lines (representing fibrosarcoma, cervical sarcoma, colon carcinoma, melanoma, neuroblastoma, erythroleukemia) were stained in an indirect immunofluorescence FACS assay. In addition, none of the normal peripheral blood cells were stained. The antibodies were tested for staining of formalin-fixed paraffin-embedded placenta tissue sections and frozen normal sections of liver, kidney, spleen, thymus and lymph node tissues. The placenta tissue sections were stained with both antibodies, while there was no staining of the other normal tissues (Lipinski 1981). These two antibodies have strictly been reported for use in in vitro diagnostic studies.

Anti-TROP-2 antibody MOv16 was generated through the immunization of mice with a crude membrane preparation of poorly differentiated ovarian carcinoma OvCa4343/83. MOv16 was tested for reactivity to a series of frozen tissue sections of benign and malignant ovarian tumors. MOv16 reacted with 31 of 54 malignant ovarian tumors and 2 of 16 benign ovarian tumors. Of the 5 mucinous ovarian tumors that were tested, MOv16 was completely unreactive. MOv16 was also tested for reactivity to frozen sections of non-ovarian malignant tumors where it was found to bind 117 of 189 breast carcinoma sections and 12 of 18 lung carcinoma sections. MOv16 was completely unreactive on 16 non-epithelial tumors that were tested (including liposarcomas, chondrosarcomas, endotheliomas, histiocytomas and dysgerminomas). When tested on frozen normal tissue sections, MOv-16 was reactive with breast, pancreas, kidney and prostate sections. MOv16 reactivity was reported to be negative on lung, spleen, skin, ovary, thyroid, parotid gland, stomach, larynx, uterus and colon sections, though the number of tissue sections that were used was not reported. The authors noted that frozen tissue sections were used because MOv16 was unreactive to paraffin embedded tissues (Miotti 1987). This antibody has also only been reported for use in in vitro diagnositic studies.

Anti-TROP-2 antibody Rs7-3G11 (RS7) was generated through the immunization of mice with a crude membrane preparation derived from a surgically removed human primary squamous cell carcinoma of the lung. IHC was used to examine the staining of RS7 on frozen sections of human tumor and normal tissues. RS7 bound to 33 of the 40 sections representing tumors of the breast, colon, kidney, lung, prostate and squamous cell cancer. Of the normal tissues RS7 bound to 16 of 20 sections of breast, colon, kidney, liver, lung and prostate tissues while none of the five sections of spleen tissue were stained. In this study the authors noted that it appeared that antigen density in tumors was higher than in normal epithelial tissues (Stein 1990).

Additional studies of the tissue specificity of RS7 were carried out on both tumor and normal tissues. RS7 was tested on a panel of frozen tumor sections and bound to 65 of the 77 sections representing tumors of the lung, stomach, kidney, bladder, colon, breast, ovary, uterus and prostate. There was no binding to the 5 lymphomas tested. RS7 was tested on a panel of 85 frozen human normal tissue sections composed of a total of 24 tissue types. 39 sections of 13 normal tissues (lung, bronchus, trachea, esophagus, colon, liver, pancreas, kidney, bladder, skin, thyroid, breast and prostate) were stained by RS7. The authors of this study noted that in the tissues in which positive staining was observed, the reactivity was generally restricted to epithelial cells, primarily in ducts or glands. It was also noted that this study was limited to frozen sections since it was observed that RS7 was not reactive on formalin-fixed paraffin-embedded sections (Stein 1993).

Polyclonal anti-TROP-2 antibodies were prepared by immunizing mice with a synthetic peptide corresponding to amino acid positions between 169 and 182 of the cytoplasmic domain of human TROP-2. The polyclonal antibodies were tested on a tissue array slide that contained formalin-fixed human esophageal hyperplasia and carcinoma tissues. Ten of the 55 carcinoma specimens displayed heavy staining with the polyclonal antibodies, while the mild hyperplasia tissue stained very weakly, indicating expression levels may be related to malignant transformation (Nakashima 2004).

Overall, IHC reactivity patterns obtained with different anti-TROP-2 antibodies were consistent. Expression in cancer was seen primarily in carcinomas, and most carcinomas were reactive. In normal tissues, expression appeared to be limited to cells of epithelial origin, and there was some evidence that staining of carcinomas was stronger than staining of corresponding normal epithelial tissues.

In addition to being used in IHC studies, antibody RS7 was tested in in vivo models with initial experiments consisting of tumor targeting studies in nude mouse xenograft models. Radiolabeled RS7 injected i.v. was shown to accumulate specifically in the tumor of mice bearing either Calu-3 (lung adenocarcinoma) or GW-39 (colon carcinoma) tumors (Stein 1990). Further studies were done to investigate the biodistribution of radiolabeled RS7 in a xenograft system and to study the therapeutic potential of RS7 as an immunoconjugate. In this study the therapeutic efficacy of $^{131}$I-labeled RS7 F(ab')$_2$ was investigated in nude mice bearing Calu-3 human lung adenocarcinoma xenografts. Three weeks following inoculation of the mice with Calu-3 cells, when the tumors had reached a size of approximately 0.3-0.9 grams, groups of 6-7 mice were treated with a single dose i.v. of either 1.0 mCi $^{131}$I-RS7-F(ab')$_2$ or 1.5 mCi $^{131}$I-RS7-F(ab')$_2$ and compared to a similar group of untreated control mice. The single dose of 1.0 mCi $^{131}$I-RS7-F(ab')$_2$ resulted in tumor growth suppression for approximately 5 weeks, while the single dose of 1.5 mCi $^{131}$I-RS7-F(ab')$_2$ resulted in tumor regression, and the mean tumor size did not exceed the pre-therapy size until the eighth week after radioantibody injection. Mice receiving the 1.5 mCi $^{131}$I-RS7-F(ab')$_2$ dose experienced a mean body weight loss of 18.7 percent, indicating there was toxicity associated with the treatment. In this study, effects of treatment with naked RS7 or the F(ab')$_2$ fragment of RS7 were not tested (Stein 1994a). Another study was done to test the efficacy of $^{131}$I-RS7 in a MDA-MB-468 breast cancer xenograft model. Groups of ten mice bearing MDA-MB-468 tumors of approximately 0.1 cm$^3$ were treated with a single dose i.v. of either 250 microcuries $^{131}$I-RS7 or 250 microcuries $^{131}$I—Ag8 (an isotype matched control antibody). Groups of six mice were treated with a single dose i.v. of 30 micrograms of either unlabeled RS7 or Ag8. Complete regression of the tumors (except for one animal that had a transient reappearance of tumor) was seen in the animals treated with $^{131}$I-RS7, which lasted for the duration of the 11 week observation period. Tumor regression was also seen in $^{131}$I-Ag8 treated mice, though was only observed between 2 weeks and 5 weeks with tumors either persisting or continuing to grow for the remainder of the study. Tumor growth of mice that received unlabeled RS7 or Ag8 was not inhibited and there did not appear to be any differences in the mean tumor volume of RS7 treated mice compared to the Ag8 treated mice. Two additional groups of 10 mice bearing larger MDA-MB-468 tumors of approximately 0.2-0.3 cm$^3$ were treated with a slightly higher single dose of either 275 microcuries $^{131}$I-Rs7 or 275 microcuries $^{131}$Ag8 and compared to a similar group of untreated mice. Tumor volume was measured weekly for 15 weeks. Although in this case there was a significant difference in tumor growth between the $^{131}$I-RS7 treated mice compared to the untreated mice, there was no significant difference in the tumor growth of the $^{131}$I-RS7 compared to the $^{131}$I—Ag8 treated mice, indicating a portion of the efficacy may have been due to non-specific effects of the radiation. Unlabeled antibodies were not tested in mice containing 0.2-0.3 cm$^3$ tumors (Shih 1995).

There have been numerous additional studies examining the efficacy of RS7 as an immunoconjugate with an attempt to select the optimal radiolabel for radioimmunotherapy (Stein 2001a, Stein 2001b, Stein 2003). A humanized version of RS7 has also been generated, however it has only been tested in preclinical xenograft models as a radioconjugate (Govindan 2004). These studies show similar positive effects as the previously described studies with RS7, however in one study, even when radiolabeled RS7 was delivered at a previously determined maximum tolerable dose, toxicity occurred leading to death in some mice (Stein 2001a). Although effective treatment of xenograft tumors in mice was achieved with radiolabeled RS7 in these studies, naked RS7 was not evaluated.

Immunizing mice with neuramindase pre-treated H3922 human breast carcinoma cells produced the anti-TROP-2 monoclonal antibody BR110 (as disclosed in U.S. Pat. No. 5,850,854, refer to Prior Patents section). By immunohistology, using human frozen tissue specimens, BR110 was shown to react with a wide range of human carcinoma specimens including those of the lung, colon, breast, ovarian, kidney, esophagus, pancreas, skin, lung and tonsil. No human normal tissue sections were tested. In vitro studies demonstrated that BR110 had no ADCC or CDC activity on the human carcinoma cell lines H3396 or H3922. In vitro studies analyzing the cytotoxicity of BR110-immunotoxins was performed on the human cancer cell lines H3619, H2987, MCF-7, H3396 and H2981. The EC$_{50}$ for the cell lines tested was 0.06, 0.001, 0.05, 0.09 and >5 micrograms/mL respectively. No cytotoxicity data was disclosed for the naked BR110 antibody. No in vivo data was disclosed for the naked or immunoconjugated BR110.

A number of additional antibodies have been generated that target TROP-2, such as MR54, MR6 and MR23 which were generated from immunization of mice with the ovarian cancer cell line Colo 316 (Stein 1994b) and antibody T16 which was generated by immunization of mice with the T24 bladder cancer cell line (Fradet 1984). The use of these antibodies has been limited to biochemical characterization of the TROP-2 antigen and cell line and tissue expression studies. There have been no reports of anti-cancer efficacy of these antibodies, either in vitro or in vivo. RS7 was the only antibody that was tested for therapeutic efficacy in preclinical cancer models, with its use being limited to a carrier of radioisotope. There are no reports of any naked TROP-2 antibodies exhibiting therapeutic efficacy in preclinical cancer models either in vitro or in vivo.

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her2/neu antibody (Herceptin®) in combination with CISPLATIN. In this trial 37 patients were assessed for responses of which about a quarter had a partial response rate and an additional quarter had minor or stable disease progression. The median time to progression among the responders was 8.4 months with median response duration of 5.3 months.

Herceptin® was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the Herceptin® plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with Herceptin® and Taxol® led to a higher incidence of cardiotoxicity in comparison to Taxol® treatment alone (13 versus 1 percent respectively). Also, Herceptin® therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from Herceptin® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1 A, which has some specificity for adenocarcinomas, has undergone Phase 2 clinical trials in over 60 patients with only 1 patient having a partial response. In other trials, use of 17-1 A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like Herceptin®, treatment in Switzerland is only approved as a combination of monoclonal antibody and chemotherapy. In addition, treatment in both Switzerland and the US is only approved, for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluourouracil alone (20 months versus 16 months respectively). However, again like Herceptin® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX)

conjugated to the cell-killing drug doxorubicin in combination with the chemotherapeutic agent TAXOTERE®. TAXOTERE® is the only FDA approved chemotherapy for the second line treatment of lung cancer. Initial data indicate an improved overall survival compared to TAXOTERE® alone. Out of the 62 patients who were recruited for the study, two-thirds received SGN-15 in combination with TAXOTERE® while the remaining one-third received TAXOTERE® alone. For the patients receiving SGN-15 in combination with TAXOTERE®, median overall survival was 7.3 months in comparison to 5.9 months for patients receiving TAXOTERE® alone. Overall survival at 1 year and 18 months was 29 and 18 percent respectively for patients receiving SNG-15 plus TAXOTERE® compared to 24 and 8 percent respectively for patients receiving TAXOTERE® alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that could contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including Herceptin® and RITUXIMAB, have been produced using these methods and selected on the basis of their affinity. The flaws in this strategy are two-fold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, have been inadequate for all types of cancer.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single-chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

U.S. Pat. No. 5,850,854 discloses a specific antibody, BR110 directed against GA733-1. This patent discloses in vitro function for BR110 as an immunotoxin conjugate.

There was no in vitro function as a naked antibody disclosed for this antibody. There was also no in vivo function disclosed for this antibody.

U.S. Pat. No. 6,653,104 claims immunotoxin-conjugated antibodies, including but not limited to RS7, directed against a host of antigens, including but not limited to EGP-1. The immunotoxin is limited to those possessing ribonucleolytic activity. However, the examples disclose only a specific immunotoxin-conjugated antibody, LL2, directed against CD22. There was no in vitro or in vivo function for RS7 disclosed in this application.

U.S. Application No. 20040001825A1 discloses a specific antibody, RS7 directed against EGP-1. This application discloses in vitro function for RS7 as a radiolabeled conjugate. There was no in vitro function as a naked antibody disclosed for this antibody. This application also discloses in vivo function for RS7 resulting from radiolabled and unlabeled conjugate administered sequentially. However, this study was limited to one patient and it is unknown whether any of the observed function was due to the unlabeled antibody. There was no in vivo function for RS7 resulting from the administration of the naked antibody.

SUMMARY OF THE INVENTION

This application utilizes methodology for producing patient specific anti-cancer antibodies taught in the U.S. Pat. No. 6,180,357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinities of these antibodies are suited to requirements for initiation of the cytotoxic events that may not be amenable to stronger affinity interactions. Also, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, cytokines, interferons, target or reporter moieties or hematogenous cells, thereby forming an antibody conjugate. The CDMAB can be used alone or in combination with one or more CDMAB/chemotherapeutic agents.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity (ADCC) or complement dependent cytotoxicity (CDC). For example murine IgM and IgG2a antibodies can activate human complement by binding the C-I component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

The cytotoxicity mediated through the Fc region requires the presence of effector cells, their corresponding receptors, or proteins e.g. NK cells, T cells and complement. In the absence of these effector mechanisms, the Fc portion of an antibody is inert. The Fc portion of an antibody may confer properties that affect the pharmacokinetics of an antibody in vivo, but in vitro this is not operative.

The cytotoxicity assays under which we test the antibodies do not have any of the effector mechanisms present, and are carried out in vitro. These assays do not have effector cells (NK, Macrophages, or T-cells) or complement present. Since these assays are completely defined by what is added together, each component can be characterized. The assays used herein contain only target cells, media and sera. The target cells do not have effector functions since they are cancer cells or fibroblasts. Without exogenous cells which have effector function properties there is no cellular elements that have this function. The media does not contain complement or any cells. The sera used to support the growth of the target cells do not have complement activity as disclosed by the vendors. Furthermore, in our own labs we have verified the absence of complement activity in the sera used. Therefore, our work evidences the fact that the effects of the antibodies are due entirely to the effects of the antigen binding which is mediated through the Fab. Effectively, the target cells are seeing and interacting with only the Fab, since they do not have receptors for the Fc. Although the hybridoma is secreting complete immunoglobulin which was tested with the target cells, the only part of the immunoglobulin that interacts with the cells are the Fab, which act as antigen binding fragments.

With respect to the instantly claimed antibodies and antigen binding fragments, the application, as filed, has demonstrated cellular cytotoxicity as evidenced by the data in FIG. 1. As pointed out above, and as herein confirmed via objective evidence, this effect was entirely due to binding by the Fab to the tumor cells.

Ample evidence exists in the art of antibodies mediating cytotoxicity due to direct binding of the antibody to the target antigen independent of effector mechanisms recruited by the Fc. The best evidence for this is in vitro experiments which do not have supplemental cells, or complement (to formally exclude those mechanisms). These types of experiments have been carried out with complete immunoglobulin, or with antigen binding fragments such as F(ab)'2 fragments. In these types of experiments, antibodies or antigen binding fragments can directly induce apoptosis of target cells such as in the case of anti-Her2 and anti-EGFR antibodies, both of which have been approved by the US FDA for marketing in cancer therapy.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end 2003, there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

The present invention describes the development and use of AR52A301.5 identified by, its effect, in a cytotoxic assay, in non-established and established tumor growth in animal models and in prolonging survival time in those suffering from cancerous disease. This invention represents an advance-in the field of cancer treatment in that it describes, for the first time, reagents that bind specifically to an epitope or epitopes present on the target molecule, TROP-2, and that also have in vitro cytotoxic properties, as a naked antibody, against malignant tumor cells but not normal cells, and which also directly mediate, as a naked antibody, inhibition of tumor growth and extension of survival in in vivo models of human cancer. This is an advance in relation to any other previously described anti-TROP-2 antibody, since none have been shown to have similar properties. It also provides an advance in the field since it clearly demonstrates, and for the first time, the direct involvement of TROP-2 in events associated with growth and development of certain types of tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the AR52A301.5 antigen as a target for a therapeutic agent, that when administered can reduce the tumor burden of a cancer expressing the antigen in a mammal, and can also lead to a prolonged survival of the treated mammal. This invention also teaches the use of CDMAB (AR52A301.5), and its derivatives, and antigen binding fragments thereof, and cellular cytotoxicity inducing ligands thereof to target their antigen to reduce the tumor burden of a cancer expressing the antigen in a mammal, and lead to prolonged survival of the treated mammal. Furthermore, this invention also teaches the use of detecting the AR52A301.5 antigen in cancerous cells that can be useful for the diagnosis, prediction of therapy, and prognosis of mammals bearing tumors that express this antigen.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 compares the percentage cytotoxicity and binding levels of the hybridoma supernatants against cell lines OCC-1, OVCAR-3 and CCD-27sk.

FIG. 2 tabulates binding of AR52A301.5 and the anti-EGFR antibody control to cancer and normal cell lines. The data is presented as the mean fluorescence intensity as a fold increase above isotype control.

Figure 23:
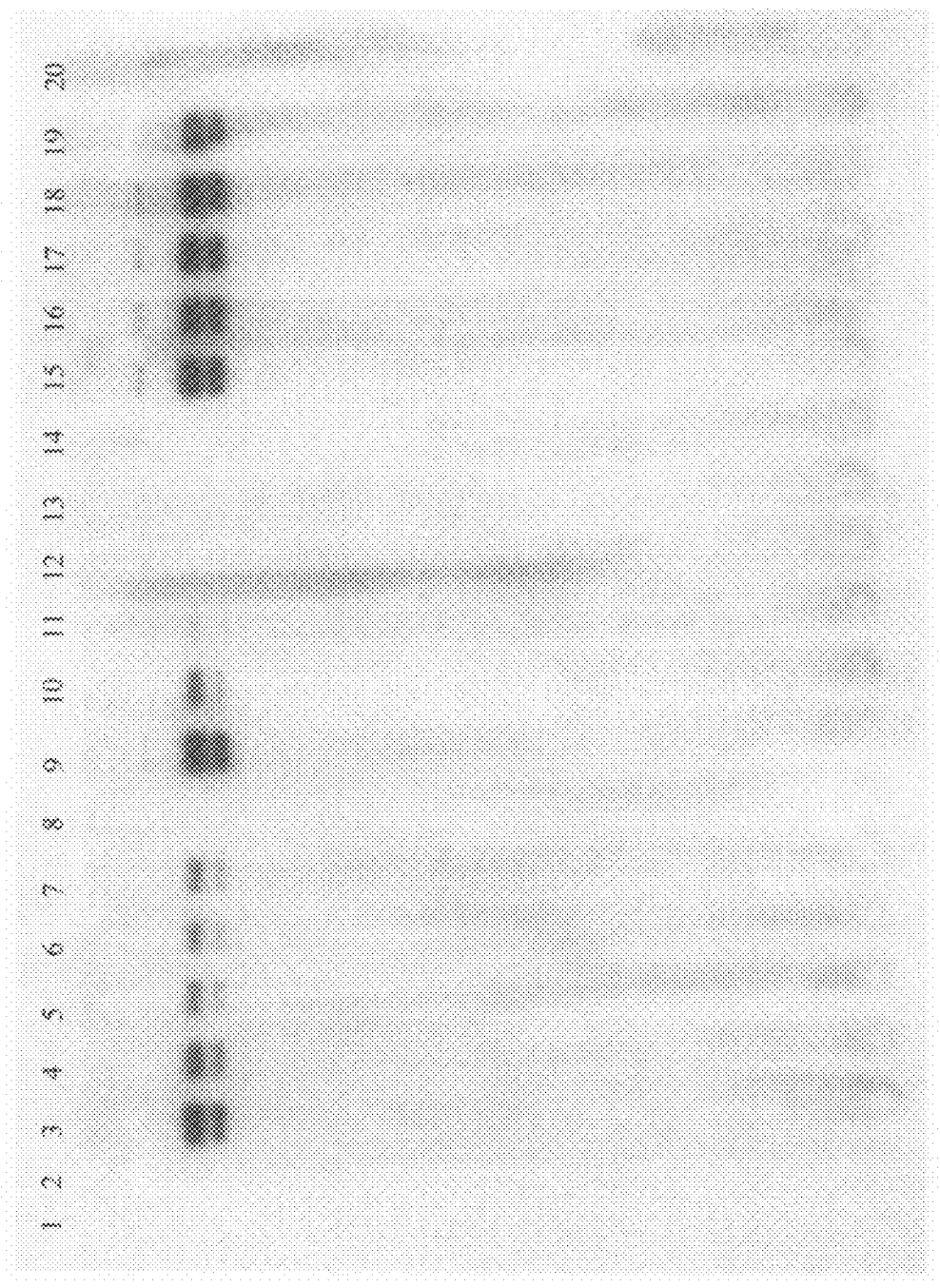

FIG. 23. Western blot of recombinant human TROP-2 probed with different primary antibody solutions. Lanes 3 to 7 were probed with biotinylated AR47A6.4.2 mixed with 0.5 microgram/mL, 5 microgram/mL, 50 microgram/mL, 500 microgram/mL and 1000 microgram/mL of non-biotinylated AR52A301.5 respectively. Lanes 9 to 13 were probed with biotinylated AR47A6.4.2 mixed with 0.5 microgram/mL, 5 microgram/mL, 50 microgram/mL, 500 microgram/mL and 1000 microgram/mL of non-biotinylated AR47A6.4.2 respectively. Lanes 15 to 19 were probed with biotinylated AR47A6.4.2 mixed with 0.5 microgram/mL, 5 microgram/mL, 50 microgram/mL, 500 microgram/mL and 1000 microgram/mL of non-biotinylated 1B7.11 respectively. Lanes 8 and 14 were incubated with negative control solution and lane 8 was not incubated in secondary solution. Lanes 1, 2 and 20 were incubated with TBST only.

FIG. 24 tabulates an IHC comparison of AR52A301.5 versus positive and negative controls on a normal human tissue micro array.

Figure 25:
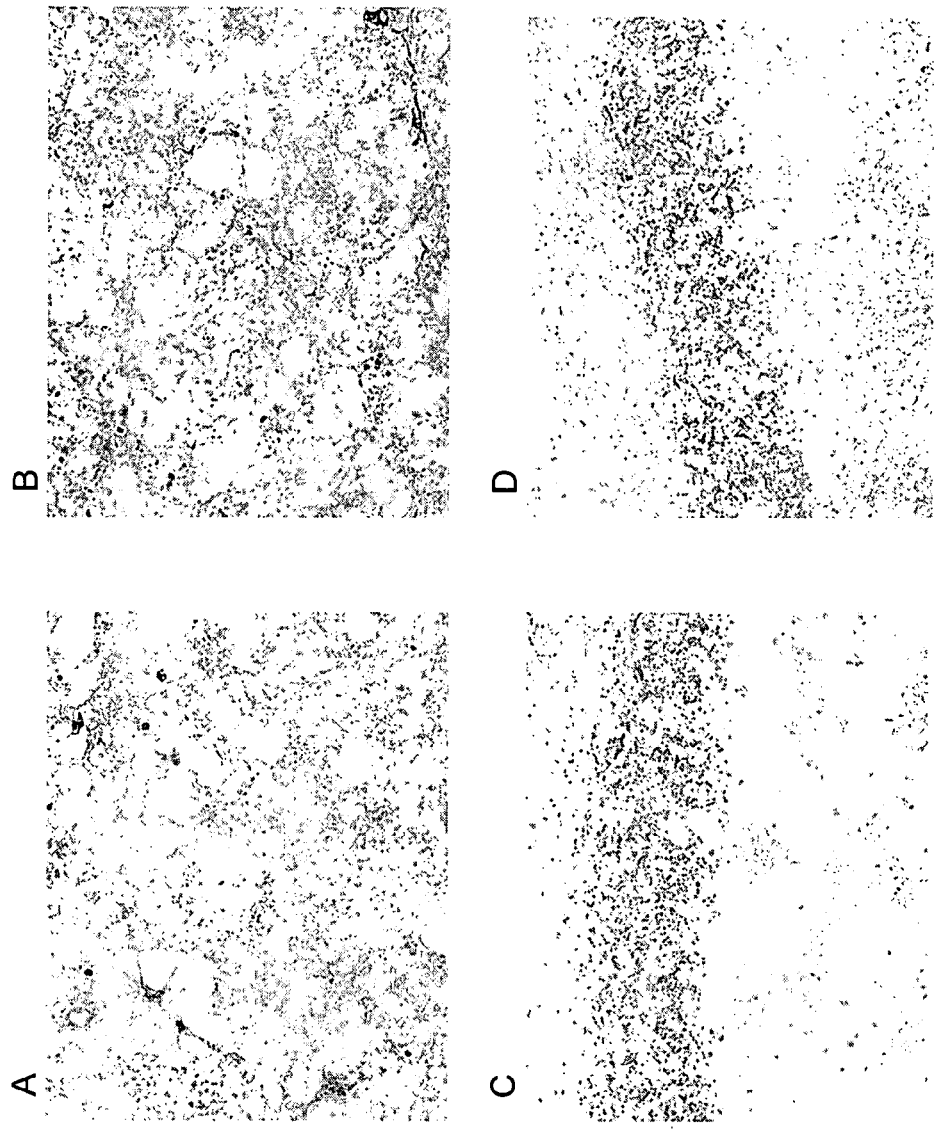

FIG. 25. Representative micrographs showing the binding pattern on spleen tissue obtained with AR52A301.5 (A) or the isotype control antibody (B) and on brain tissue obtained with AR52A301.5 (C) or the isotype control antibody (D) from a normal human tissue microarray. Magnification is 200×.

FIG. 26 tabulates an IHC comparison of AR52A301.5 on various human tumor and normal tissue sections from different normal human tissue micro arrays.

Figure 27:
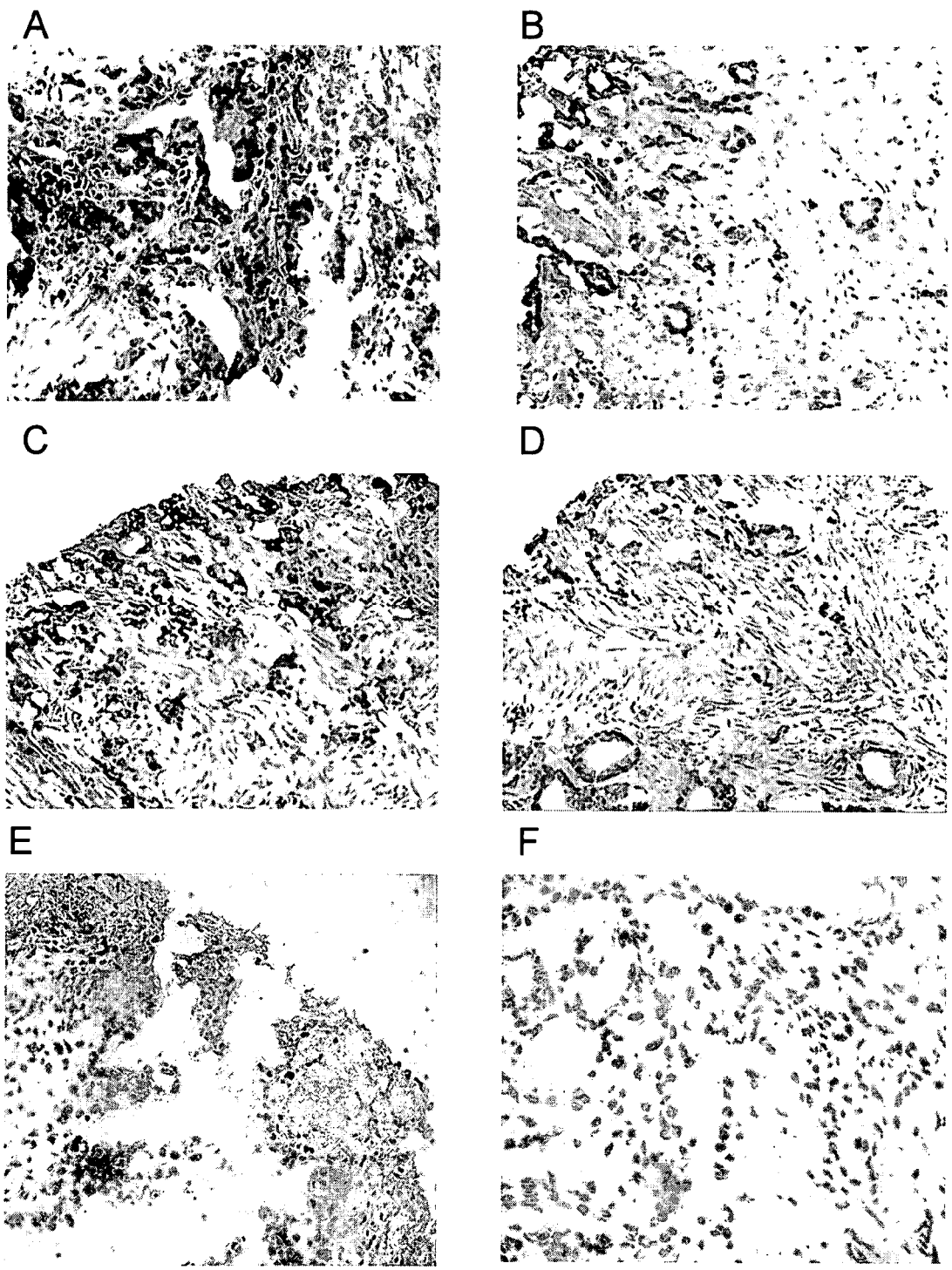

FIG. 27. Representative micrographs showing the binding pattern on breast tumor tissue obtained with AR52A301.5 (A) or the isotype control antibody (B) and on prostate tumor tissue obtained with AR52A301.5 (C) or the isotype control antibody (D) and on pancreatic tumor tissue obtained with AR52A301.5 (E) or the isotype control antibody (F) from various human tumor tissue microarrays. Magnification is 200×.

FIG. 28 tabulates an IHC comparison of AR52A301.5 on various human and other species normal tissue sections from different normal species tissue micro arrays.

Figure 29:
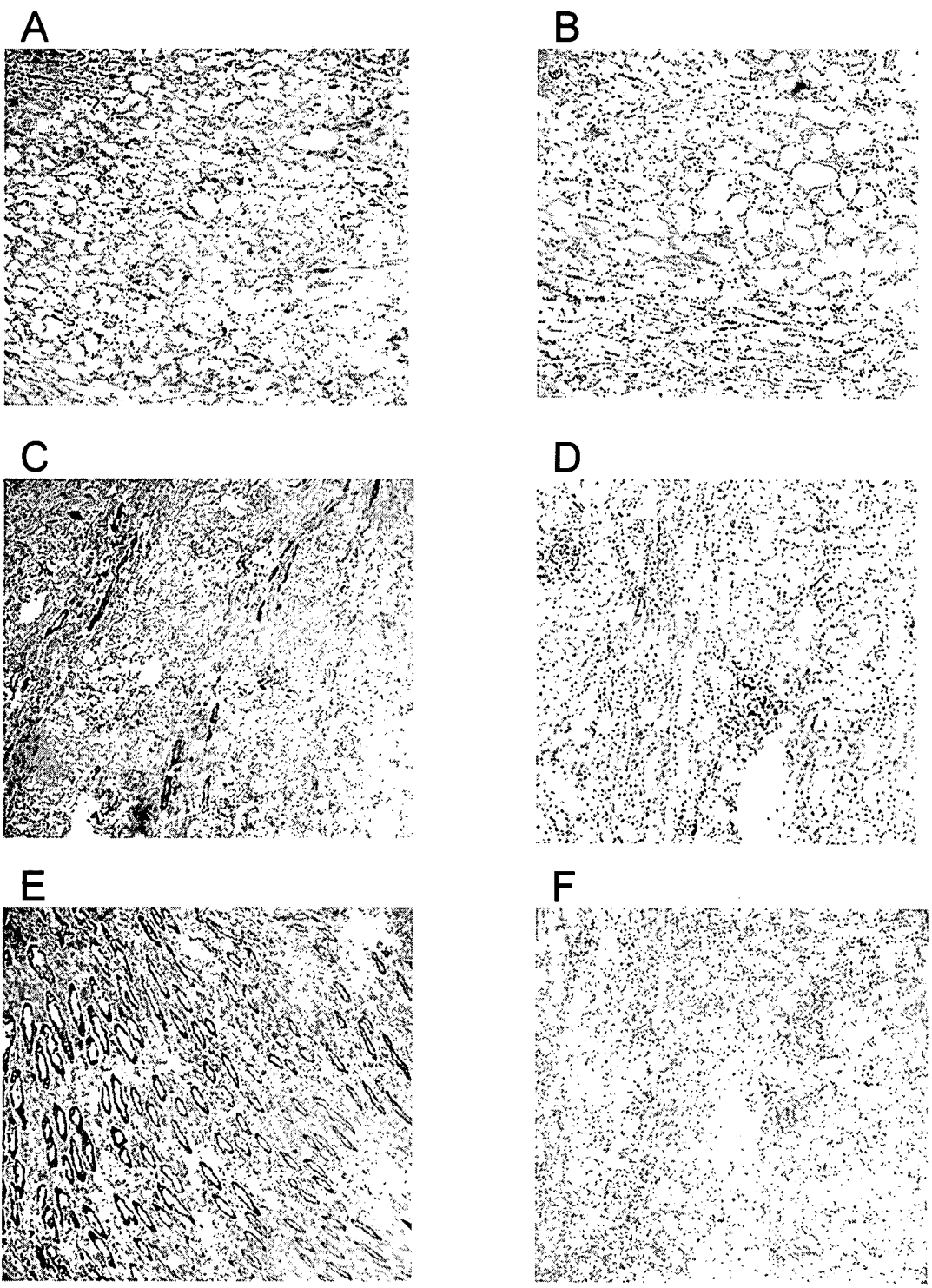

FIG. 29. Representative micrographs showing the binding pattern on normal human kidney tissue obtained with AR52A301.5 (A) or the isotype control antibody (B) and on normal cynomolgus kidney tissue obtained with AR52A301.5 (C) or the isotype control antibody (D) and on normal rhesus tissue obtained with AR52A301.5 (E) or the isotype control antibody (F) from various multi-species tissue microarrays. Magnification is 200×.

FIG. 30. Sequences of all oligonucleotide primers (SEQ ID NOS:9-46) used in the murine sequence determination of AR52A301.5.

Figure 31:
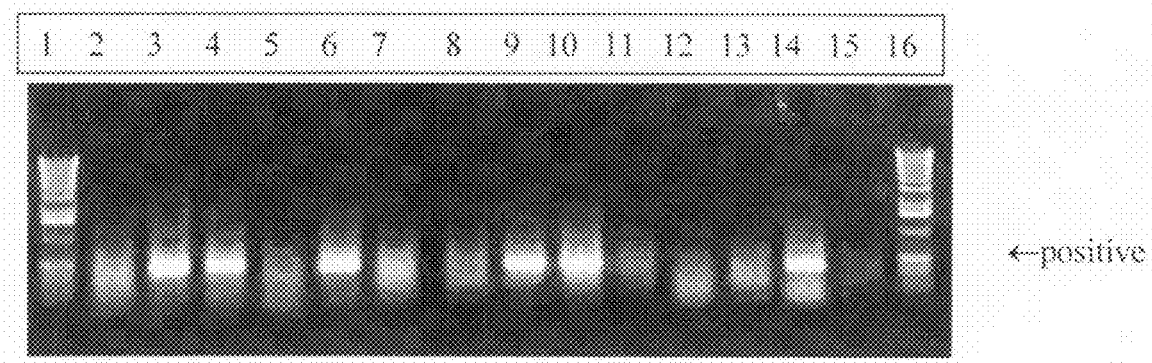

FIG. 31. Agarose gel of the RT/PCR amplification of AR52A301.5 $V_H$ and $V_L$ regions.

Figure 32:

FIG. 32. Agarose gel of the PCR colony screen of AR52A301.5 $V_H$-B, $V_H$-E and $V_L$-G.

FIG. 33. AR52A301.5 $V_L$ amino acid sequence (SEQ ID NO:8).

FIG. 34. AR52A301.5 $V_H$ amino acid sequence (SEQ ID NO:7).

DETAILED DESCRIPTION OF THE INVENTION

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimeric or humanized antibodies), antibody compositions with polyepitopic specificity, single-chain antibodies, diabodies, triabodies, immunoconjugates and antibody fragments (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are. advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multi-specific antibodies formed from antibody fragment(s).

An "intact" antibody is one which comprises an antigen-binding variable region as well as a light chain constant domain (C$_L$) and heavy chain constant domains, C$_H$1, C$_H$2 and C$_H$3. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, d, e, ?, and µ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc?RIII only, whereas monocytes express Fc?RI, Fc?RII and Fc?RIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Effector cells" are leukocytes which express one or more FcRs and perform effector functions. Preferably, the cells express at least Fc?RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc?RI, Fc?RII, and Fc?RIII subclasses, including allelic variants and alternatively spliced forms of these receptors. Fc?RII receptors include Fc?RIIA (an "activating receptor") and Fc?RIIB (an "inhibiting receptor"), which have similar amino acid sequences that differ primarily in the cytoplasmic domains thereof. Activating receptor Fc?RIIA contains an immunoreceptor tyrosine-based activation motif (ITAM) in its cytoplasmic domain. Inhibiting receptor Fc?RIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., Eur. *J. Immunol.* 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (?).and lambda (?), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/1116 1; and Hollinger et al., *Proc. Natl. Acad. Sci. USA*, 90:6444-6448 (1993).

The term "triabodies" or "trivalent trimers" refers to the combination of three single chain antibodies. Triabodies are constructed with the amino acid terminus of a $V_L$ or $V_H$ domain, i.e., without any linker sequence. A triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. TROP-2 antigen, is one capable of binding that antigen with sufficient affinity such that the antibody is useful as a therapeutic or diagnostic agent in targeting a cell expressing the antigen. Where the antibody is one which binds TROP-2, it will usually preferentially bind TROP-2 as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment or treating" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, camomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2?-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats; cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.*, 14:5399-5407, 1986. They are then purified on polyacrylamide gels.

In accordance with the present invention, "humanized" and/or "chimeric" forms of non-human (e.g. murine) immunoglobulins refer to antibodies which contain specific chimeric immunoglobulins, immunoglobulin chains or fragments thereof (such as Fv, Fab, Fab', F(ab')$_2$ or other antigen-binding subsequences of antibodies) which results in the decrease of a human anti-mouse antibody (HAMA), human anti-chimeric antibody (HACA) or a human anti-human antibody (HAHA) response, compared to the original antibody, and contain the requisite portions (e.g. CDR(s), antigen binding region(s), variable domain(s) and so on) derived from said non-human immunoglobulin, necessary to reproduce the desired effect, while simultaneously retaining binding characteristics which are comparable to said non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

An antibody which induces "apoptosis" is one which induces programmed cell death by any means, illustrated by but not limited to binding of annexin V, caspase activity, fragmentation of DNA, cell shrinkage, dilation of endoplasmic reticulum, cell fragmentation, and/or formation of membrane vesicles (called apoptotic bodies).

As used herein "antibody induced cytotoxicity" is understood to mean the cytotoxic effect derived from the hybridoma supernatant or antibody produced by the hybridoma deposited with the IDAC as accession number 141205-03 which effect is not necessarily related to the degree of binding.

Throughout the instant specification, hybridoma cell lines, as well as the isolated monoclonal antibodies which are produced therefrom, are alternatively referred to by their internal designation, AR52A301.5 or Depository Designation, IDAC 141205-03.

As used herein "antibody-ligand" includes a moiety which exhibits binding specificity for at least one epitope of the target antigen, and which may be an intact antibody molecule, antibody fragments, and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds at least one epitope of the antigen bound by the isolated monoclonal antibody produced by the hybridoma cell line designated as IDAC 141205-03 (the IDAC 141205-03 antigen).

As used herein "cancerous disease modifying antibodies" (CDMAB) refers to monoclonal antibodies which modify the cancerous disease process in a manner which is beneficial to the patient, for example by reducing tumor burden or prolonging survival of tumor bearing individuals, and antibody-ligands thereof.

A "CDMAB related binding agent", in its broadest sense, is understood to include, but is not limited to, any form of human or non-human antibodies, antibody fragments, antibody ligands, or the like, which competitively bind to at least one CDMAB target epitope.

A "competitive binder" is understood-to include any form of human or non-human antibodies, antibody fragments, antibody ligands, or the like which has binding affinity for at least one CDMAB target epitope.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents but recur up to five years, sometimes up to ten years or longer after treatment is discontinued.

Tumors that can be treated include tumors that are not vascularized, or not yet substantially vascularized, as well as vascularized tumors. Examples of solid tumors, which can be accordingly treated, include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma.

As used herein "antigen-binding region" means a portion of the molecule which recognizes the target antigen.

As used herein "competitively inhibits" means being able to recognize and bind a determinant site to which the monoclonal antibody produced by the hybridoma cell line designated as IDAC 141205-03, (the IDAC 141205-03 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the IDAC 141205-03 antigen or portions thereof.

As used herein, an "immunoconjugate" means any molecule or CDMAB such as an antibody chemically or biologically linked to cytotoxins, radioactive agents, cytokines, interferons, target or reporter moieties, enzymes, toxins, anti-tumor drugs or therapeutic agents. The antibody or CDMAB may be linked to the cytotoxin, radioactive agent, cytokine, interferon, target or reporter moiety, enzyme, toxin, anti-tumor drug or therapeutic agent at any location along the molecule so long as it is able to bind its target. Examples of immunoconjugates include antibody toxin chemical conjugates and antibody-toxin fusion proteins.

Radioactive agents suitable for use as anti-tumor agents are known to those skilled in the art. For example, 131I or 211At is used. These isotopes are attached to the antibody using conventional techniques (e.g. Pedley et al., Br. J. Cancer 68, 69-73 (1993)). Alternatively, the anti-tumor agent which is attached to the antibody is an enzyme which activates a prodrug. A prodrug may be administered which will remain in its inactive form until it reaches the tumor site where it is converted to its cytotoxin form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-a). The antibody targets the cytokine to the tumor so that the cytokine mediates damage to or destruction of the tumor without affecting other tissues. The cytokine is fused to the antibody at the DNA level using conventional recombinant DNA techniques. Interferons may also be used.

As used herein, a "fusion protein" means any chimeric protein wherein an antigen binding region is connected to a biologically active molecule, e.g., toxin, enzyme, fluorescent proteins, luminescent marker, polypeptide tag, cytokine, interferon, target or reporter moiety or protein drug.

The invention further contemplates CDMAB of the present invention to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is avidin and biotin. In a preferred embodiment, biotin is conjugated to the target antigen of the CDMAB of the present invention, and thereby provides a target for an anti-tumor agent or other moiety which is conjugated to avidin or streptavidin. Alternatively, biotin or another such moiety is linked to the target antigen of the CDMAB of the present invention and used as a reporter, for example in a diagnostic system where a detectable signal-producing agent is conjugated to avidin or streptavidin.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

Moreover, included within the scope of the present invention is use of the present CDMAB in vivo and in vitro for investigative or diagnostic methods, which are well known in the art. In order to carry out the diagnostic methods as contemplated herein, the instant invention may further include kits, which contain CDMAB of the present invention. Such kits will be useful for identification of individuals at risk for certain type of cancers by detecting over-expression of the CDMAB's target antigen on cells of such individuals.

Diagnostic Assay Kits

It is contemplated to utilize the CDMAB of the present invention in the form of a diagnostic assay kit for determining the presence of a tumor. The tumor will generally be detected in a patient based on the presence of one or more tumor-specific antigens, e.g. proteins and/or polynucleotides which encode such proteins in a biological sample, such as blood, sera, urine and/or tumor biopsies, which samples will have been obtained from the patient.

The proteins function as markers which indicate the presence or absence of a particular tumor, for example a colon, breast, lung or prostate tumor. It is further contemplated that the antigen will have utility for the detection of other cancerous tumors. Inclusion in the diagnostic assay kits of binding agents comprised of CDMABs of the present invention, or CDMAB related binding agents, enables detection of the level of antigen that binds to the agent in the biological sample. Polynucleotide primers and probes may be used to detect the level of mRNA encoding a tumor protein, which is also indicative of the presence or absence of a cancer. In order for the binding assay to be diagnostic, data will have been generated which correlates statistically significant levels of antigen, in relation to that present in normal tissue, so as to render the recognition of binding definitively diagnostic for the presence of a cancerous tumor. It is contemplated that a plurality of formats will be useful for the diagnostic assay of the present invention, as are known to those of ordinary skill in the art, for using a binding agent to detect polypeptide markers in a sample. For example, as illustrated in Harlow and Lane, Antibodies: A Laboratory Manual, Cold Spring Harbor Laboratory, 1988. Further contemplated are any and all combinations, permutations or modifications of the afore-described diagnostic assay formats.

The presence or absence of a cancer in a patient will typically be determined by (a) contacting a biological sample obtained from a patient with a binding agent; (b) detecting in the sample a level of polypeptide that binds to the binding agent; and (c) comparing the level of polypeptide with a predetermined cut-off value.

In an illustrative embodiment, it is contemplated that the assay will involve the use of a CDMAB based binding agent immobilized on a solid support to bind to and remove the polypeptide from the remainder of the sample. The bound polypeptide may then be detected using a detection reagent that contains a reporter group and specifically binds to the binding agent/polypeptide complex. Illustrative detection reagents may include a CDMAB based binding agent that specifically binds to the polypeptide or an antibody or other agent that specifically binds to the binding agent, such as an anti-immunoglobulin, protein G, protein A or a lectin. In an alternative embodiment, it is contemplated that a competitive assay may be utilized, in which a polypeptide is labeled with a reporter group and allowed to bind to the immobilized binding agent after incubation of the binding agent with the sample. Indicative of the reactivity of the sample with the immobilized binding agent, is the extent to which components of the sample inhibit the binding of the labeled polypeptide to the binding agent. Suitable polypeptides for use within such assays include full length tumor-specific proteins and/or portions thereof, to which the binding agent has binding affinity.

The diagnostic kit will be provided with a solid support which may be in the form of any material known to those of ordinary skill in the art to which the protein may be attached. Suitable examples may include a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

It is contemplated that the binding agent will be immobilized on the solid support using a variety of techniques known to those of skill in the art, which are amply described in the patent and scientific literature. The term "immobilization" refers to both noncovalent association, such as adsorption, and covalent attachment, which, in the context of the present invention, may be a direct linkage between the agent and functional groups on the support, or may be a linkage by way of a cross-linking agent. In a preferred, albeit non-limiting embodiment, immobilization by adsorption to a well in a microtiter plate or to a membrane is preferable. Adsorption may be achieved by contacting the binding agent, in a suitable buffer, with the solid support for a suitable amount of time. The contact time may vary with temperature, and will generally be within a range of between about 1 hour and about 1 day.

Covalent attachment of binding agent to a solid support would ordinarily be accomplished by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12 A13).

It is further contemplated that the diagnostic assay kit will take the form of a two-antibody sandwich assay. This assay may be performed by first contacting an antibody, e.g. the instantly disclosed CDMAB that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

In a specific embodiment, it is contemplated that once the antibody is immobilized on the support as described above, the remaining protein binding sites on the support will be blocked, via the use of any suitable blocking agent known to those of ordinary skill in the art, such as bovine serum albumin or Tween 20™ (Sigma Chemical Co., St. Louis, Mo.). The immobilized antibody would then be incubated with the sample, and polypeptide would be allowed to bind to the antibody. The sample could be diluted with a suitable diluent, such as phosphate-buffered saline (PBS) prior to incubation. In general, an appropriate contact time (i.e., incubation time) would be selected to correspond to a period of time sufficient to detect the presence of polypeptide within a sample obtained from an individual with the specifically selected tumor. Preferably, the contact time is sufficient to achieve a level of binding that is at least about 95 percent of that achieved at equilibrium between bound and unbound polypeptide. Those of ordinary skill in the art will recognize that the time necessary to achieve equilibrium may be readily determined by assaying the level of binding that occurs over a period of time.

It is further contemplated that unbound sample would then be removed by washing the solid support with an appropriate buffer. The second antibody, which contains a reporter group, would then be added to the solid support. Incubation of the detection reagent with the immobilized antibody-polypeptide complex would then be carried out for an amount of time sufficient to detect the bound polypeptide. Subsequently, unbound detection reagent would then be removed and bound detection reagent would be detected using the reporter group. The method employed for detecting the reporter group is necessarily specific to the type of reporter group selected, for example for radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

In order to utilize the diagnostic assay kit of the present invention to determine the presence or absence of a cancer, such as prostate cancer, the signal detected from the reporter group that remains bound to the solid support would generally be compared to a signal that corresponds to a predetermined cut-off value. For example, an illustrative cut-off value for the detection of a cancer may be the average mean signal obtained when the immobilized antibody is incubated with samples from patients without the cancer. In general, a sample generating a signal that is about three standard deviations above the predetermined cut-off value would be considered positive for the cancer. In an alternate embodiment, the cut-off value might be determined by using a Receiver Operator Curve, according to the method of Sackett et al., Clinical Epidemiology. A Basic Science for Clinical Medicine, Little Brown and Co., 1985, p. 106-7. In such an embodiment, the cut-off value could be determined from a plot of pairs of true positive rates (i.e., sensitivity) and false positive rates (100 percent-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

It is contemplated that the diagnostic assay enabled by the kit will be performed in either a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound will be immersed in a solution containing the sample. The sample migrates along the membrane through a region containing second binding agent and to the area of immobilized binding agent. Concentration of the second binding agent at the area of immobilized antibody indicates the presence of a cancer. Generation of a pattern, such as a line, at the binding site, which can be read visually, will be indicative of a positive test. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in the instant diagnostic assay are the instantly disclosed antibodies, antigen-binding fragments thereof, and any CDMAB related binding agents as herein described. The amount of antibody immobilized on the membrane will be any amount effective to produce a diagnostic assay, and may range from about 25 nanograms to about 1 microgram. Typically such tests may be performed with a very small amount of biological sample.

Additionally, the CDMAB of the present invention may be used in the laboratory for research due to its ability to identify its target antigen.

In order that the invention herein described may be more fully understood, the following description is set forth.

The present invention provides CDMAB (i.e., IDAC 141205-03 CDMAB) which specifically recognize and bind the IDAC 141205-03 antigen.

The CDMAB of the isolated monoclonal antibody produced by the hybridoma deposited with the IDAC as accession number 141205-03 may be in any form as long as it has an antigen-binding region which competitively inhibits the immunospecific binding of the isolated monoclonal antibody produced by hybridoma IDAC 141205-03 to its target antigen. Thus, any recombinant proteins (e.g., fusion proteins wherein the antibody is combined with a second protein such as a lymphokine or a tumor inhibitory growth factor) having the same binding specificity as the IDAC 141205-03 antibody fall within the scope of this invention.

In one embodiment of the invention, the CDMAB is the IDAC 141205-03 antibody.

In other embodiments, the CDMAB is an antigen binding fragment which may be a Fv molecule (such as a single-chain Fv molecule), a Fab molecule, a Fab' molecule, a F(ab')2 molecule, a fusion protein, a bispecific antibody, a heteroantibody or any recombinant molecule having the antigen-binding region of the IDAC 141205-03 antibody. The CDMAB of the invention is directed to the epitope to which the IDAC 141205-03 monoclonal antibody is directed.

The CDMAB of the invention may be modified, i.e., by amino acid modifications within the molecule, so as to produce derivative molecules. Chemical modification may also be possible. Modification by direct mutation, methods of affinity maturation, phage display or chain shuffling may also be possible.

Affinity and specificity can be modified or improved by mutating CDR and/or phenylalanine tryptophan (FW) residues and screening for antigen binding sites having the desired characteristics (e.g., Yang et al., J. Mol. Biol., (1995) 254: 392-403). One way is to randomize individual residues or combinations of residues so that in a population of otherwise identical antigen binding sites, subsets of from two to twenty amino acids are found at particular positions. Alternatively, mutations can be induced over a range of residues by error prone PCR methods (e.g., Hawkins et al., J. Mol. Biol., (1992) 226: 889-96). In another example, phage display vectors containing heavy and light chain variable region genes can be propagated in mutator strains of E. coli (e.g., Low et al., J. Mol. Biol., (1996) 250: 359-68). These methods of mutagenesis are illustrative of the many methods known to one of skill in the art.

Another manner for increasing affinity of the antibodies of the present invention is to carry out chain shuffling, where the heavy or light chain are randomly paired with other heavy or light chains to prepare an antibody with higher affinity. The various CDRs of the antibodies may also be shuffled with the corresponding CDRs in other antibodies.

Derivative molecules would retain the functional property of the polypeptide, namely, the molecule having such substitutions will still permit the binding of the polypeptide to the IDAC 141205-03 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these-hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

EXAMPLE 1

Hybridoma Production—Hybridoma Cell Line AR52A301.5

The hybridoma cell line AR52A301.5 was deposited, in accordance with the Budapest Treaty, with the International Depository Authority of Canada (IDAC), Bureau of Microbiology, Health Canada, 1015 Arlington Street, Winnipeg, Manitoba, Canada, R3E 3R2, on Dec. 14, 2005, under Accession Number 141205-03. In accordance with 37 CFR 1.808, the depositors assure that all restrictions imposed on the availability to the public of the deposited materials will be irrevocably removed upon the granting of a patent. The deposit will be replaced if the depository cannot dispense viable samples.

To produce the hybridoma that produces the anti-cancer antibodies AR52A301.5, a single cell suspension of frozen human ovarian tumor tissue (endometroid adenocarcinoma; Genomics Collaborative, Cambridge, Mass.) was prepared in PBS. IMMUNEASY™ (Qiagen, Venlo, Netherlands) adjuvant was prepared for use by gentle mixing. Five to seven week old BALB/c mice were immunized by injecting intraperitoneally, 2 million cells in 50 microliters of the antigen-adjuvant. Recently prepared antigen-adjuvant was used to boost both the AR52A301.5 immunized mice intraperitoneally, 2 and 5 weeks after the initial immunization, with approximately 2 million cells in 50-60 microliters. A spleen was used for fusion three days after the last immunization. The hybridomas were prepared by fusing the isolated splenocytes with NSO-1 myeloma partners. The supernatants from the fusions were tested from subclones of the hybridomas.

To determine whether the antibodies secreted by the hybridoma cells are of the IgG or IgM isotype, an ELISA assay was employed. 100 microliters/well of goat anti-mouse IgG+IgM (H+L) at a concentration of 2.4 micrograms/mL in coating buffer (0.1 M carbonate/bicarbonate buffer, pH 9.2-9.6) at 4° C. was added to the ELISA plates overnight. The plates were washed thrice in washing buffer (PBS+0.05 percent Tween-20). 100 microliters/well blocking buffer (5 percent milk in wash buffer) was added to the plate for 1 hour at room temperature and then washed thrice in washing buffer. 100 microliters/well of hybridoma supernatant was added and the plate incubated for 1 hour at room temperature. The plates were washed thrice with washing buffer and 1/100,000 dilution of either goat anti-mouse IgG or IgM horseradish peroxidase conjugate (diluted in PBS containing 1 percent milk), 100 microliters/well, was added. After incubating the plate for 1 hour at room temperature the plate was washed thrice with washing buffer 100 microliters/well of TMB solution was incubated for 1-3 minutes at room temperature. The color reaction was terminated by adding 50 microliters/well 2M $H_2SO_4$ and the plate was read at 450 nm with a Perkin-Elmer HTS7000 plate reader. As indicated in FIG. 1, the AR52A301.5 hybridoma secreted primarily antibodies of the IgG isotype.

To determine the subclass of antibody secreted by the hybridoma cells, an isotyping experiment was performed using a Mouse Monoclonal Antibody Isotyping Kit (HyCult Biotechnology, Frontstraat, Netherlands). 500 microliters of buffer solution was added to the test strip containing rat anti-mouse subclass specific antibodies. 500 microliters of hybridoma supernatant was added to the test tube, and submerged by gentle agitation. Captured mouse immunoglobulins were detected directly by a second rat monoclonal antibody which is coupled to colloid particles. The combination of these two proteins creates a visual signal used to analyse the isotype. The anti-cancer antibody AR52A301.5 is of the IgG1, kappa isotype.

After one round of limiting dilution, hybridoma supernatants were tested for antibodies that bound to target cells in a cell ELISA assay. Two human ovarian cancer cell lines and 1 human normal skin cell line were tested: OCC-1, OVCAR-3 and CCD-27sk respectively. All cell lines, except for OCC-1, were obtained from the American Type Tissue Collection (ATCC, Manassas, Va.). The OCC-1 ovarian cancer cell line was obtained from the Ottawa Regional Cancer Center (Ottawa, ON).

The plated cells were fixed prior to use. The plates were washed thrice with PBS containing $MgCl_2$ and $CaCl_2$ at room temperature. 100 microliters of 2 percent paraformaldehyde diluted in PBS was added to each well for 10 minutes at room temperature and then discarded. The plates were again washed with PBS containing $MgCl_2$ and $CaCl_2$ three times at room temperature. Blocking was done with 100 microliters/well of 5 percent milk in wash buffer (PBS+0.05 percent Tween-20) for 1 hour at room temperature. The plates were washed thrice with wash buffer and the hybridoma supernatant was added at 75 microliters/well for 1 hour at room temperature. The plates were washed 3 times with wash buffer and 100 microliters/well of 1/25,000 dilution of goat anti-mouse IgG antibody conjugated to horseradish peroxidase (diluted in PBS containing 1 percent milk) was added. After 1 hour incubation at room temperature the plates were washed 3 times with wash buffer and 100 microliter/well of TMB substrate was incubated for 1-3 minutes at room temperature. The reaction was terminated with 50 microliters/well 2M $H_2SO_4$ and the plate read at 450 nm with a Perkin-Elmer HTS7000 plate reader. The results as tabulated in FIG. 1 were expressed as the number of folds above background compared to an in-house IgG isotype control that has previously been shown not to bind to the cell lines tested. The antibodies from the hybridoma AR52A301.5 showed binding to the ovarian cancer cell line OVCAR-3. AR52A301.5 did not display a detectable level of binding to the normal skin cell line CCD-27sk.

In conjunction with testing for antibody binding, the cytotoxic effect of the hybridoma supernatants was tested in the cell lines: OCC-1, OVCAR-3 and CCD-27sk. Calcein AM was obtained from Molecular Probes (Eugene, Oreg.). The assays were performed according to the manufacturer's instructions with the changes outlined below. Cells were plated before the assay at the predetermined appropriate density. After 2 days, 75 microliters of supernatant from the hybridoma microtitre plates were transferred to the cell plates and incubated in a 5 percent $CO_2$ incubator for 5 days. The wells that served as the positive controls were aspirated until empty and 100 microliters of sodium azide ($NaN_3$) or cycloheximide was added. After 5 days of treatment, the plates were then emptied by inverting and blotting dry. Room temperature DPBS (Dulbecco's phosphate buffered saline) containing $MgCl_2$ and $CaCl_2$ was dispensed into each well from a multichannel squeeze bottle, tapped 3 times, emptied by inversion and then blotted dry. 50 microliters of the fluorescent calcein dye diluted in DPBS containing $MgCl_2$ and $CaCl_2$ was added to each well and incubated at 37° C. in a 5 percent $C0_2$ incubator for 30 minutes. The plates were read in a Perkin-Elmer HTS7000 fluorescence plate reader and the data was analyzed in Microsoft Excel. The results are tabulated in FIG. 1. Supernatant from the AR52A301.5 hybridoma produced specific cytotoxicity of 24 percent on the OVCAR-3 cells. This was 53 percent of the cytotoxicity obtained with the positive control cycloheximide. Results from FIG. I demonstrate that the cytotoxic effects of AR52A301.5 are proportional to the binding levels on the cancer cell types. There was a greater level of cytotoxicity produced in the OVCAR-3 cells as compared to the OCC-1 cells, coinciding with the higher level of binding in the OVCAR-3 cells. As tabulated in FIG. 1, AR52A301.5 did not produce cytotoxicity in the CCD-27sk normal cell line. The known non-specific cytotoxic agents cycloheximide and sodium azide generally produced cytotoxicity as expected.

EXAMPLE 2

In Vitro Binding

AR52A301.5 monoclonal antibodies were produced by culturing the hybridoma in CL-1000 flasks (BD Biosciences, Oakville, ON) with collections and reseeding occurring twice/week. Standard antibody purification procedures with Protein G Sepharose 4 Fast Flow (Amersham Biosciences, Baie d'Urfé, QC) were followed. It is within the scope of this invention to utilize monoclonal antibodies that are de-immunized, humanized, chimeric or murine.

Binding of AR52A301.2 to pancreatic (BxPC-3, AsPC-1 and PL45), colon (DLD-1, Lovo, SW1116, HT-29 and Colo-205), breast (MDA-MB-468 and MCF-7), prostate (PC-3 and DU-145), lung (NCl-H520 and A549), esophageal (T.Tn), thyroid (SW579), head and neck (FaDu) and ovarian (OCC-1, C-13, OVCA-429, Sk-OV-3, OV2008, Hey, A2780-cp, A2780-s and OVCAR-3) cancer cell lines, and non-cancer cell lines from skin (CCD-27sk) and lung (Hs888.Lu) was assessed by flow cytometry (FACS). All cell lines, except for the majority of ovarian cancer cell lines, were obtained from the American Type Tissue Collection (ATCC, Manassas, Va.). C-13, OV2008, Hey, A2780-cp, A2780-s, OCC-1 and OVCA-429 ovarian cancer cell lines were obtained from the Ottawa Regional Cancer Center (Ottawa, ON).

Figure 3:
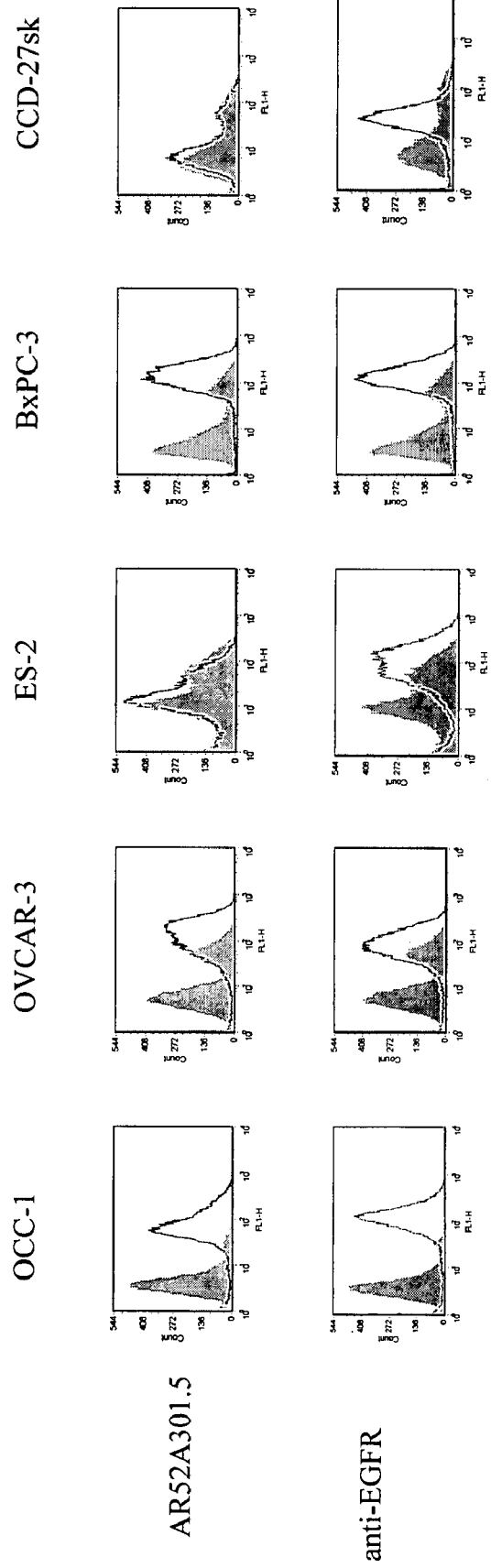
FIG. 3 includes representative FACS histograms of AR52A301.5 and anti-EGFR antibodies directed against several cancer and non-cancer cell lines.

Cells were prepared for FACS by initially washing the cell monolayer with DPBS (without $Ca^{++}$ and $Mg^{++}$). Cell dissociation buffer (INVITROGEN, Burlington, ON) was then used to dislodge the cells from their cell culture plates at 37° C. After centrifugation and collection, the cells were resuspended in DPBS containing $MgCl_2$, $CaCl_2$ and 2 percent fetal bovine serum at 4° C. (staining media) and counted, aliquoted to appropriate cell density, spun down to pellet the cells and resuspended in staining media at 4° C. in the presence of test antibodies (AR52A301.5) or control antibodies (isotype control, anti-EGFR) at 20 micrograms/mL on ice for 30 minutes. Prior to the addition of Alexa Fluor 546-conjugated secondary antibody the cells were washed once with staining media. The Alexa Fluor 546-conjugated antibody in staining media was then added for 30 minutes at 4° C. The cells were then washed for the final time and resuspended in fixing media (staining media containing 1.5 percent paraformaldehyde). Flow cytometric acquisition of the cells was assessed by running samples on a FACSarray™ using the FACSarray™ System Software (BD Biosciences, Oakville, ON). The forward (FSC) and side scatter (SSC) of the cells were set by adjusting the voltage and amplitude gains on the FSC and SSC detectors. The detectors for the fluorescence (Alexa-546) channel was adjusted by running unstained cells such that cells had a uniform peak with a median fluorescent intensity of approximately 1-5 units. For each sample, approximately 10,000 gated events (stained fixed cells) were acquired for analysis and the results are presented in FIG. 3.

FIG. 2 presents the mean fluorescence intensity fold increase above isotype control. Representative histograms of AR52A301.5 antibodies were compiled for FIG. 3. AR52A301.5 showed strong binding to the pancreatic cancer cell line BxPC-3 (29.4-fold), breast cancer cell line MDA-MB-468 (22.7-fold), head and neck cancer cell line FaDu (59.8-fold), ovarian cancer cell lines OV2008, OVAR-3 and C-13 (32.7-fold, 22.1-fold and 38.7-fold) and the colon cancer cell lines Colo-205 and DLD-1 (38.6-fold and 82.8-fold). Binding was also observed on the ovarian cancer cell lines Hey, OCC-1, OVCA-429 and OVCAR-3 (5.9-fold, 17.8-fold, 3.4-fold and 22.1-fold respectively), breast cancer cell line MCF-7 (16.0-fold), prostate cancer cell lines PC-3 and DU-145 (5.0-fold and 3.9-fold), esophageal cancer cell line T.Tn (18.6-fold), colon cancer cell line HT-29 (6.7-fold) and pancreatic cell line PL45 (12.9-fold) with weaker binding on the lung cancer cell line NCl-H520 (2.1-fold) and non-cancer lung cell line Hs888.Lu (2.6-fold). Binding to the non-cancer cell line from skin (CCD-27sk) was not detectable under these conditions. These data demonstrate that AR52A301.5 exhibited functional specificity in that although there was clear binding to a variety of cancer cell lines there was only associated cytotoxicity with some of the lines tested.

EXAMPLE 3

In Vivo Prophylactic Tumor Experiments with BxPC-3 Cells

Examples 1 and 2 demonstrated that AR52A301.5 had anti-cancer properties against a human cancer cell line with detectable binding across several different cancer indications. With reference to FIGS. 4 and 5, 6 to 8 week old female SCID mice were implanted with 5 million human pancreatic cancer cells (BxPC-3) in 100 microliters saline injected subcutaneously in the scruff of the neck. The mice were randomly divided into 3 treatment groups of 5. On the day after implantation, 20 mg/kg of AR52A301.5 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for a period of 7 weeks in the same fashion. Tumor growth was measured about every seventh day with calipers for 8 weeks or until individual animals reached Canadian Council for Animal Care (CCAC) endpoints. Body weights of the animals were recorded once per week for the duration of the study. At the end of the study all animals were euthanised according to CCAC guidelines.

Figure 4:
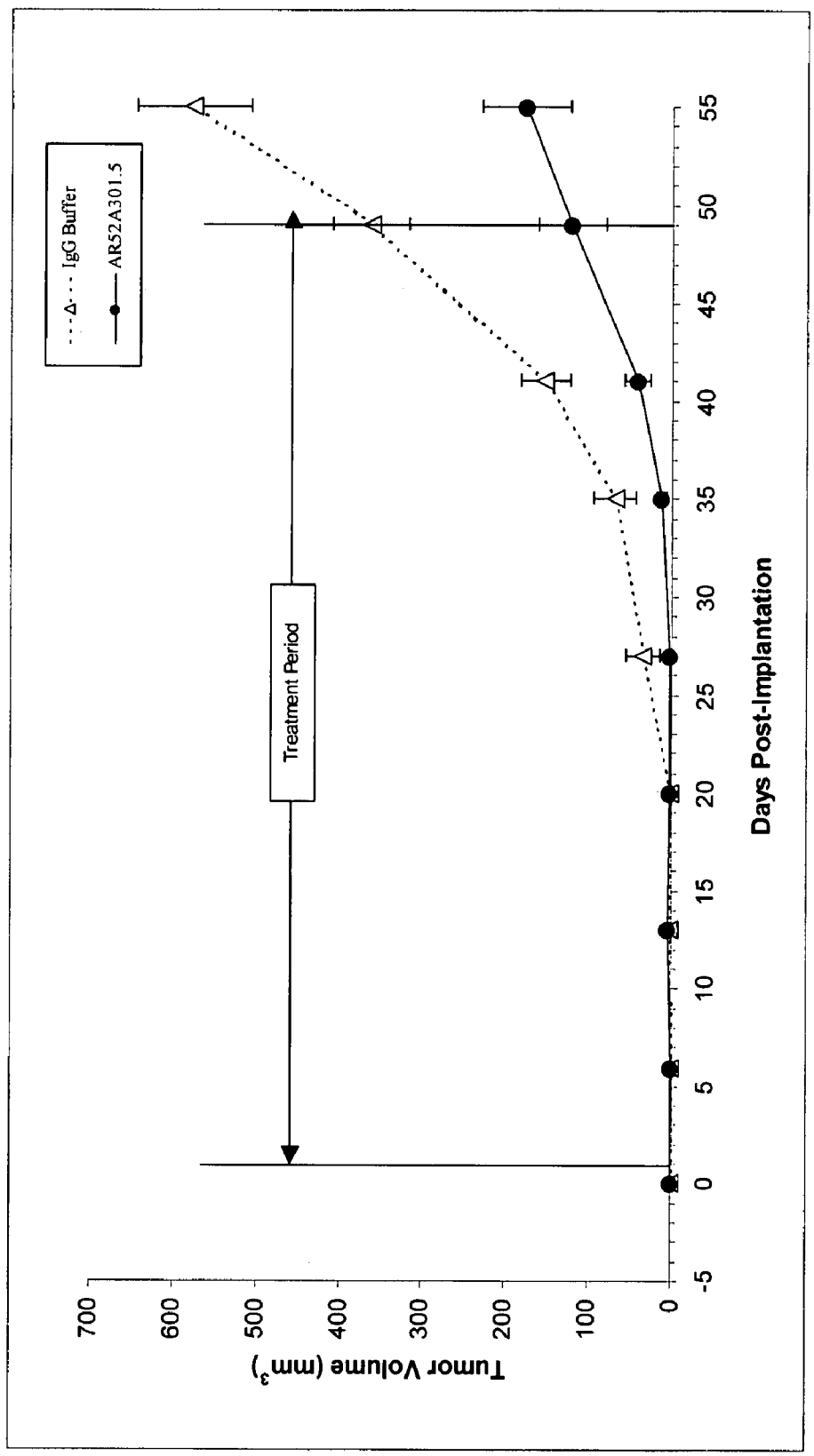
FIG. 4 demonstrates the effect of AR52A301.5 on tumor growth in a prophylactic BxPC-3 pancreatic cancer model. The vertical lines indicate the period during which the antibody was administered. Data points represent the mean +/– SEM.
Figure 5:
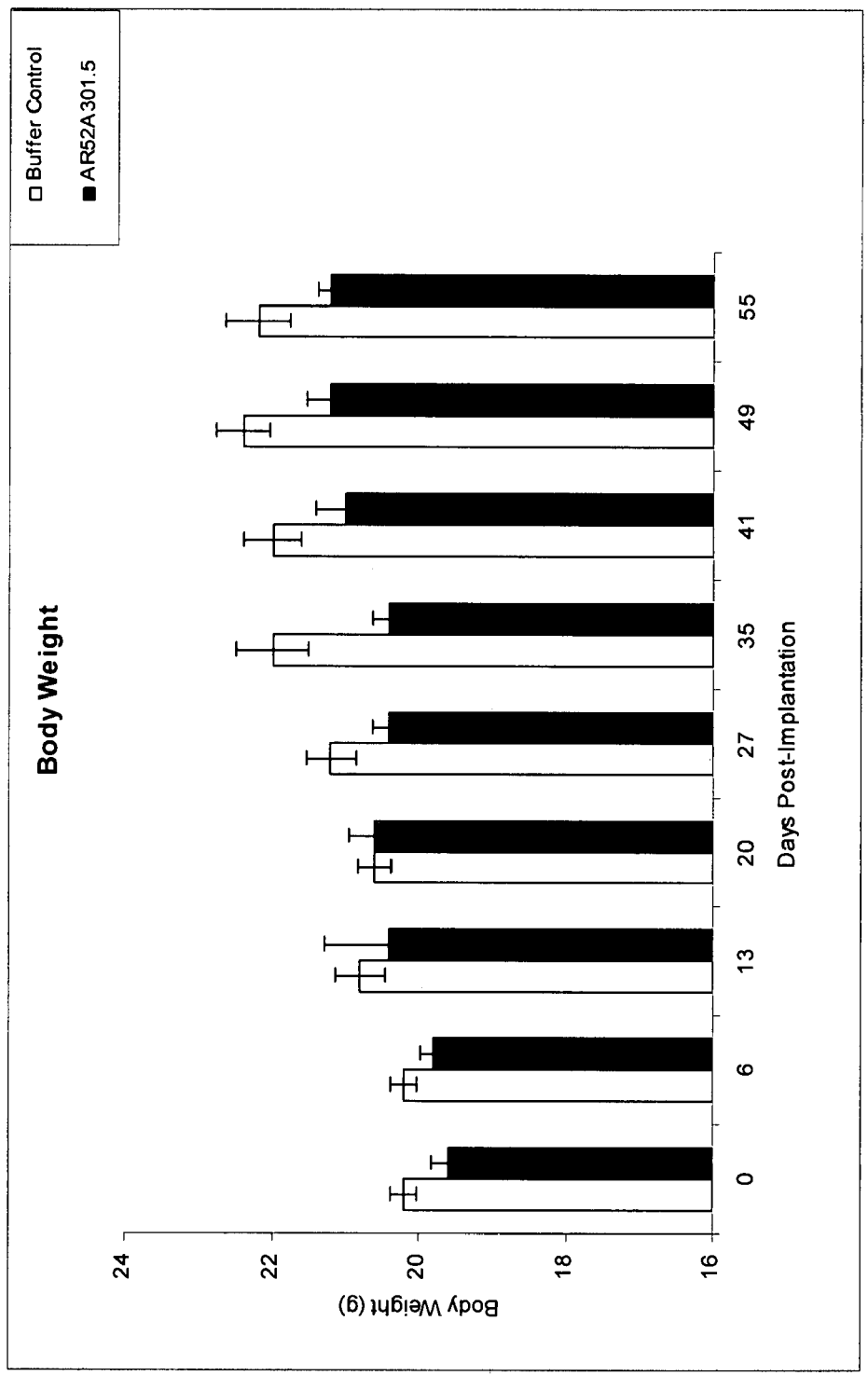
FIG. 5 demonstrates the effect of AR52A301.5 on body weight in a prophylactic BxPC-3 pancreatic cancer model. Data points represent the mean +/– SEM.

AR52A301.5 also prevented tumor growth and reduced tumor burden in an in vivo prophylactic model of human pancreatic cancer. On day 55 post-implantation, 6 days after the last treatment dose, the mean tumor volume in the AR52A301.5 treated group was 70 percent less than that of the buffer control-treated group ($p<0.002$; FIG. 4).

There were no clinical signs of toxicity throughout the study. Body weight, shown in FIG. 5, was used as a surrogate for well-being and failure to thrive. Within groups, there was a nonsignificant 10 percent increase in body weight in the control group over the duration of the study. As well, there was a nonsignificant increase in the body weight of the AR52A301.5 treated group; an 8 percent increase from a mean of 19.6 g to 21.2 g.

In summary, AR52A301.5 was well-tolerated and decreased the tumor burden in this human pancreatic cancer xenograft model.

EXAMPLE 4

In Vivo Established Tumor Experiments with BxPC-3 Cells

Figure 6:
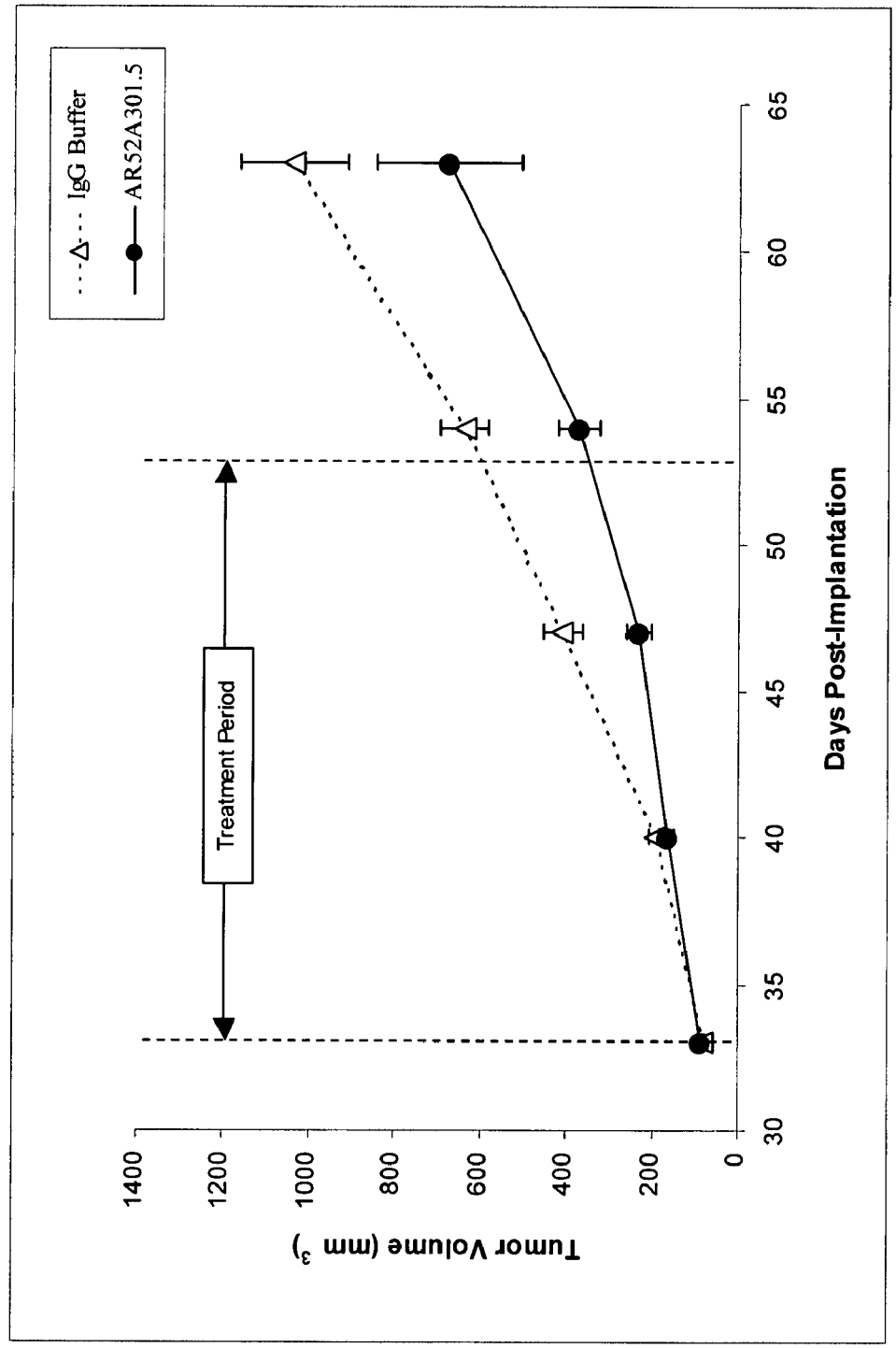
FIG. 6 demonstrates the effect of AR52A301.5 on tumor growth in an established BxPC-3 pancreatic cancer model. The vertical lines indicate the period during which the antibody was administered. Data points represent the mean +/– SEM.
Figure 7:
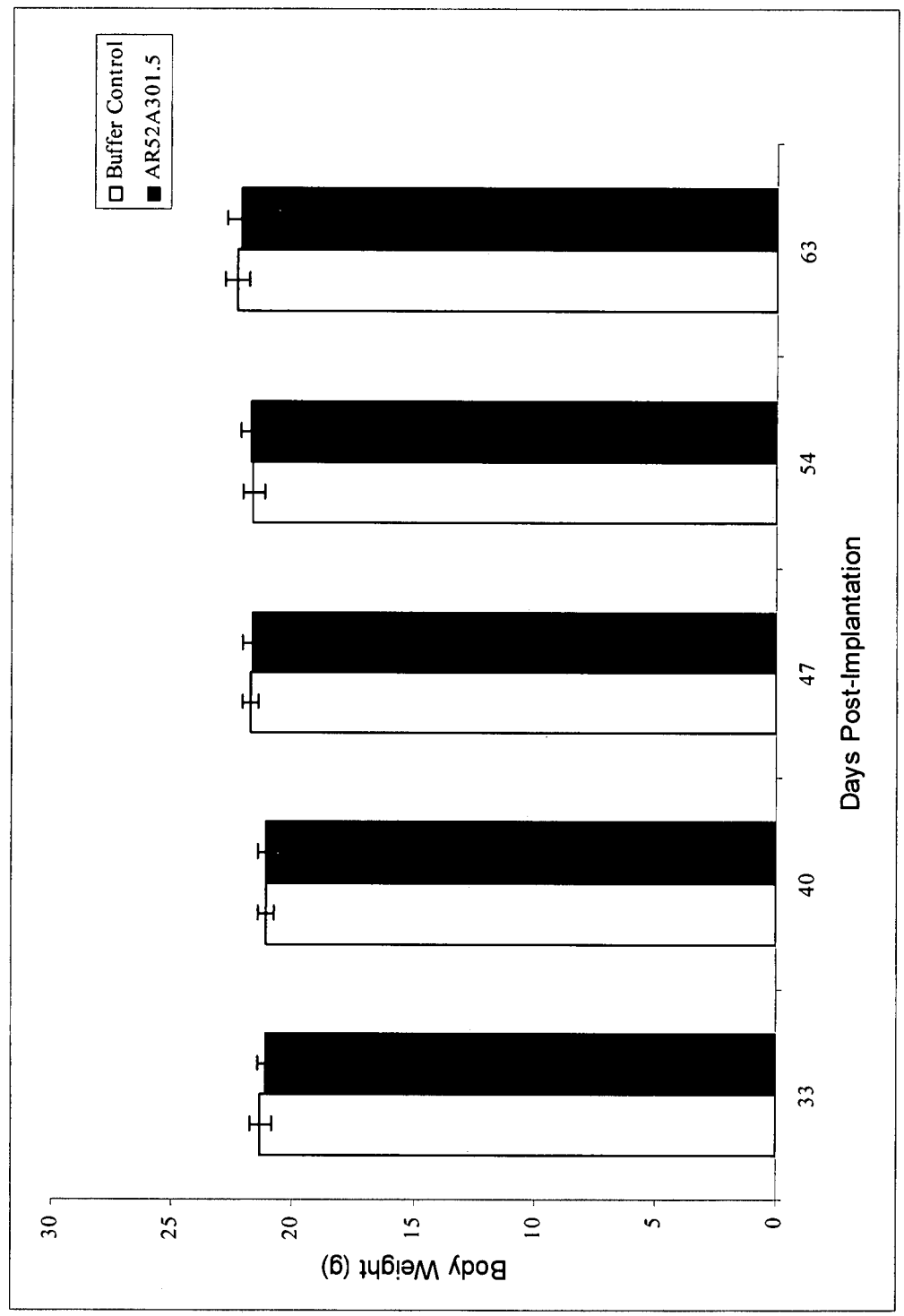
FIG. 7 demonstrates the effect of AR52A301.5 on body weight in an established BxPC-3 pancreatic cancer model. Data points represent the mean +/– SEM.
Figure 8:
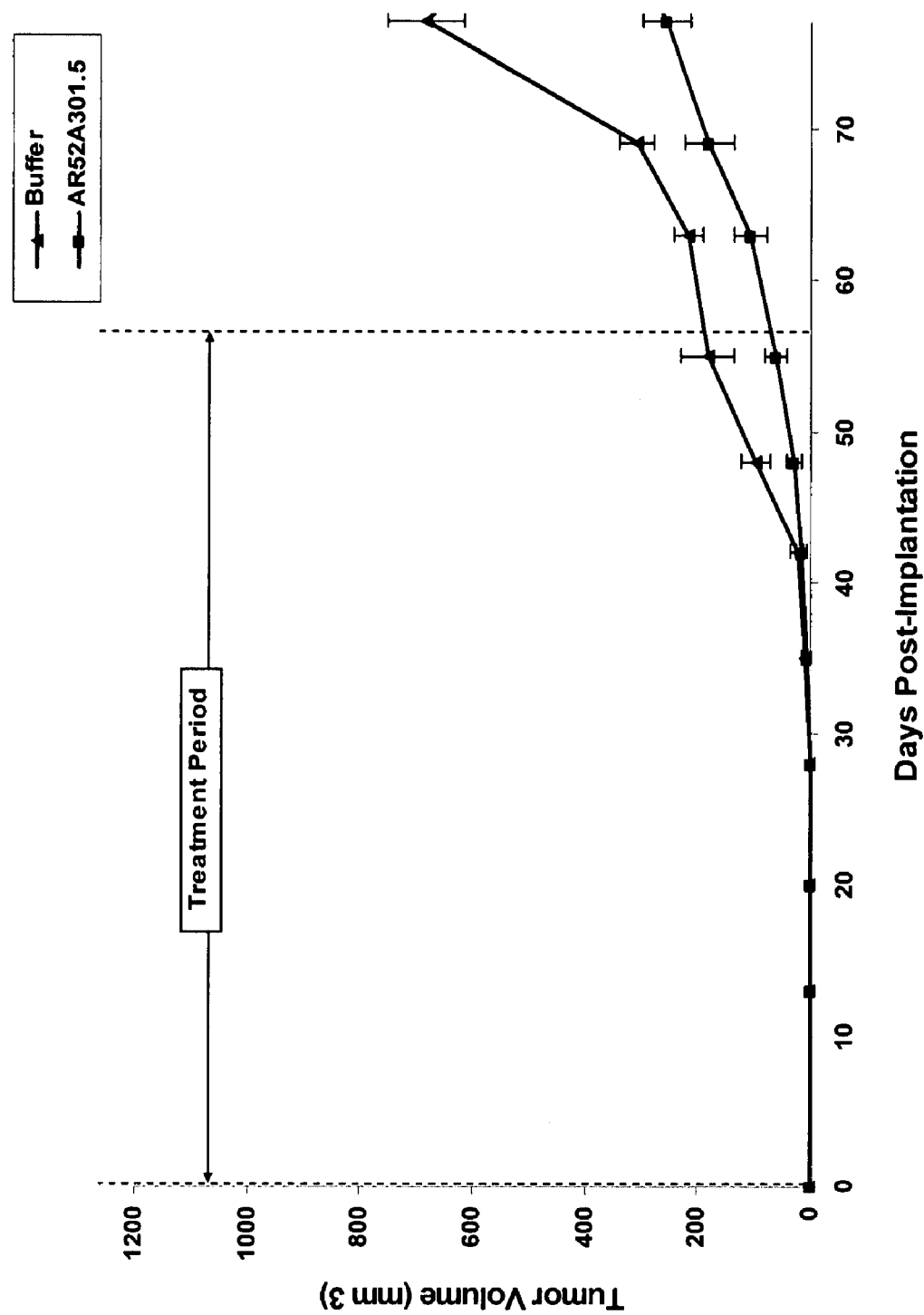
FIG. 8 demonstrates the effect of AR52A301.5 on tumor growth in a prophylactic PL45 pancreatic cancer model. The vertical lines indicate the period during which the antibody was administered. Data points represent the mean +/– SEM.

To further determine the efficacy of AR52A301.5 on the BxPC-3 model of human pancreatic cancer, the antibody was tested on an established BxPC-3 xenograft model. With reference to FIGS. 6 and 7, 6 to 8 week old female SCID mice were implanted with 5 million human pancreatic cancer cells (BxPC-3) in 100 microliters saline injected subcutaneously in the scruff of the neck. Tumor growth was measured with calipers every week. When the majority of the cohort reached an average tumor volume of 85 mm3 (range 56-111) at 33 days post-implantation 9 mice were randomly assigned into each of 2 treatment groups. AR52A301.5 test antibody or buffer control was administered intraperitoneally to each cohort, with dosing at 20 mg/kg of antibody in a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered 3 times per week for a total of 10 doses in the same fashion until day 53 post-implantation. Tumor growth was measured about every seventh day with calipers until day 63 post-implantation or until individual animals reached the CCAC end-points. Body weights of the animals were recorded once per week for the duration of the study. At the end of the study all animals were euthanised according to CCAC guidelines.

AR52A301.5 significantly reduced tumor burden in an established model of human pancreatic cancer. On day 54, AR52A301.5-treated animals had a mean tumor volume that was 58 percent of the mean tumor volume in control-treated animals (p<0.002; FIG. 6). These results correspond to a mean T/C of 51 percent for AR52A301.5

Body weight measured at weekly intervals was used as a surrogate for well-being and failure to thrive. As seen in FIG. 7, there was no significant difference in mean body weight between the two antibody-treated groups and the control at the end of the study. In addition, body weight in all groups did not vary significantly over the course of the study.

In summary, AR52A301.5 was well-tolerated and decreased the tumor burden in this established human pancreatic cancer xenograft model. AR52A301.5 has demonstrated efficacy in both a preventative and established model of human pancreatic cancer.

EXAMPLE 5

In Vivo Prophylactic Tumor Experiments with PL45 Cells

Figure 9:
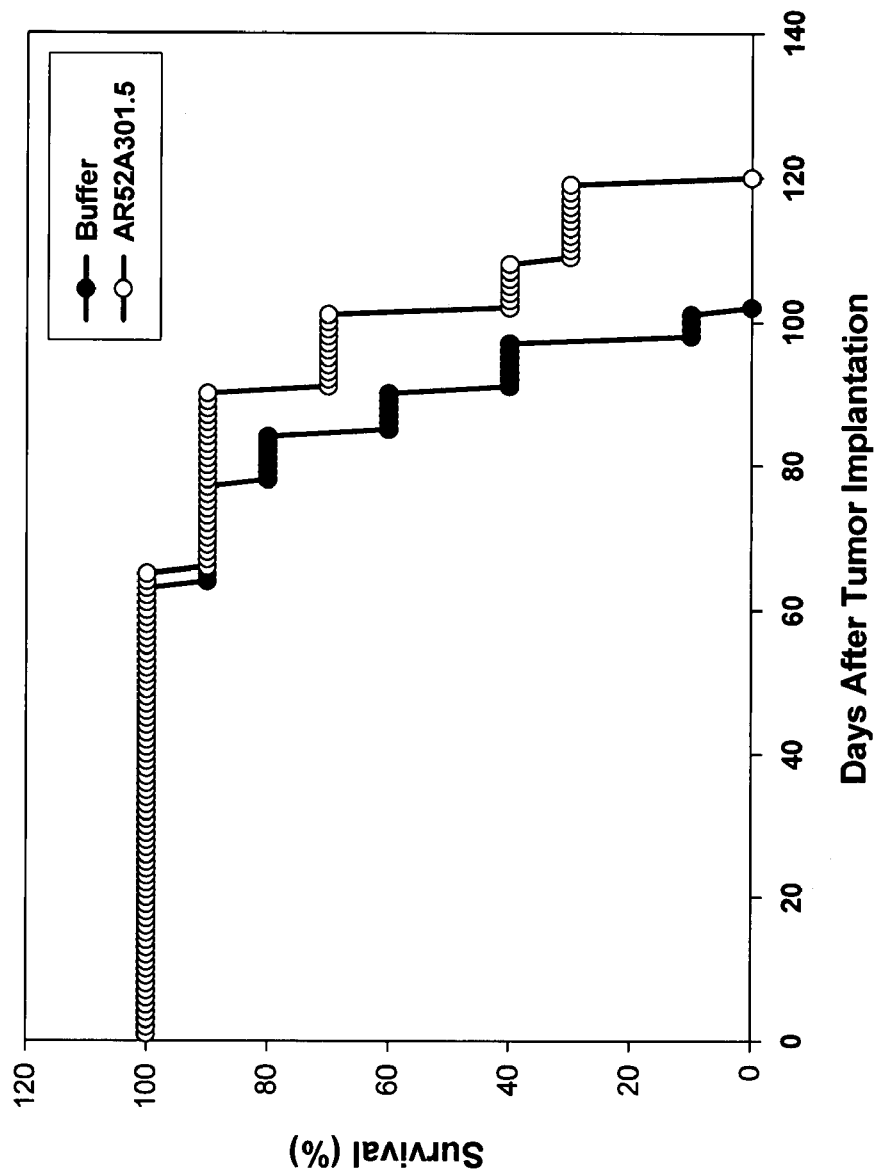
FIG. 9 demonstrates the effect of AR52A301.5 on survival in a prophylactic PL45 pancreatic cancer model.
Figure 10:
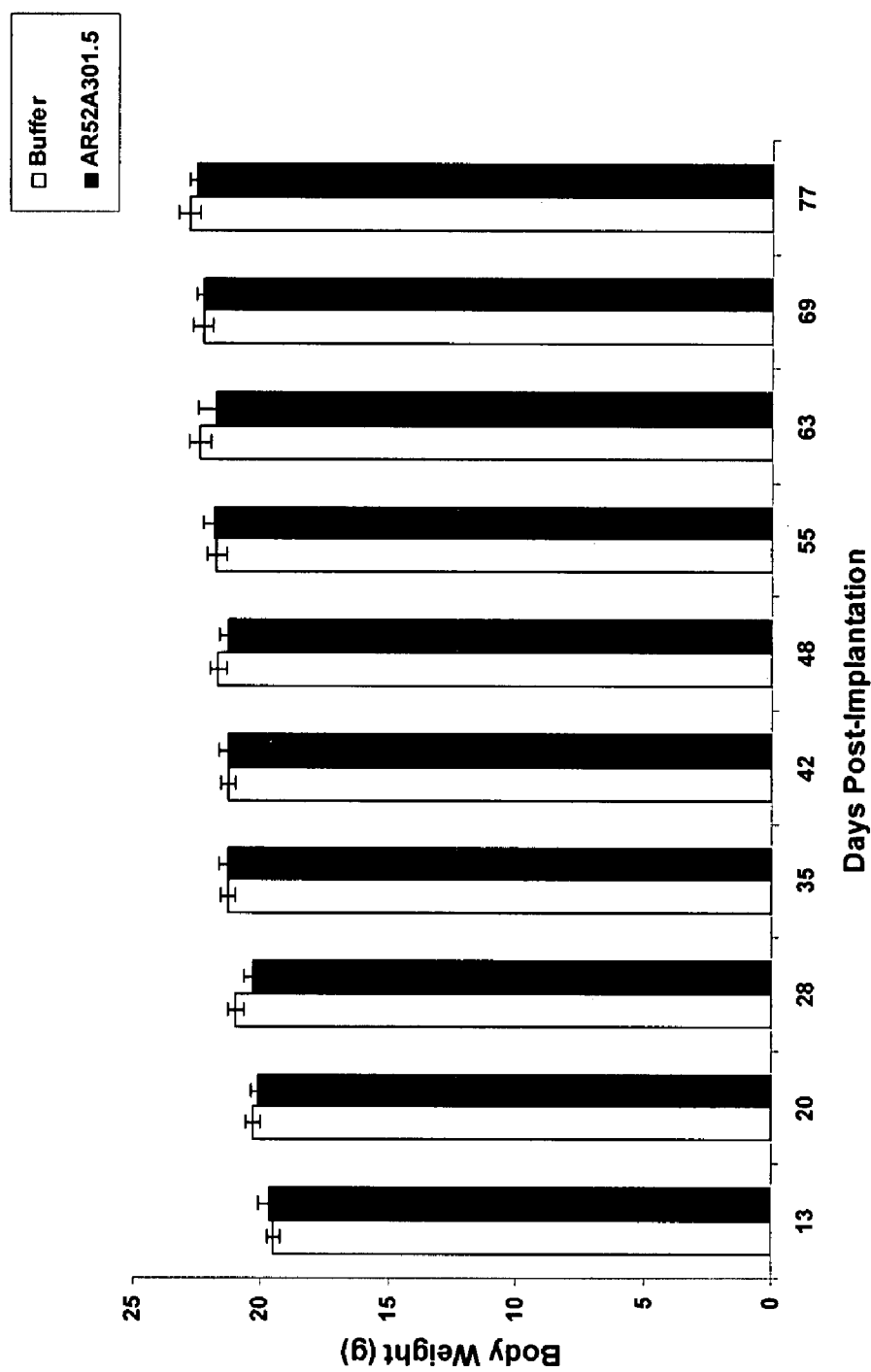
FIG. 10 demonstrates the effect of AR52A301.5 on body weight in a prophylactic PL45 pancreatic cancer model. Data points represent the mean +/– SEM.
Figure 11:
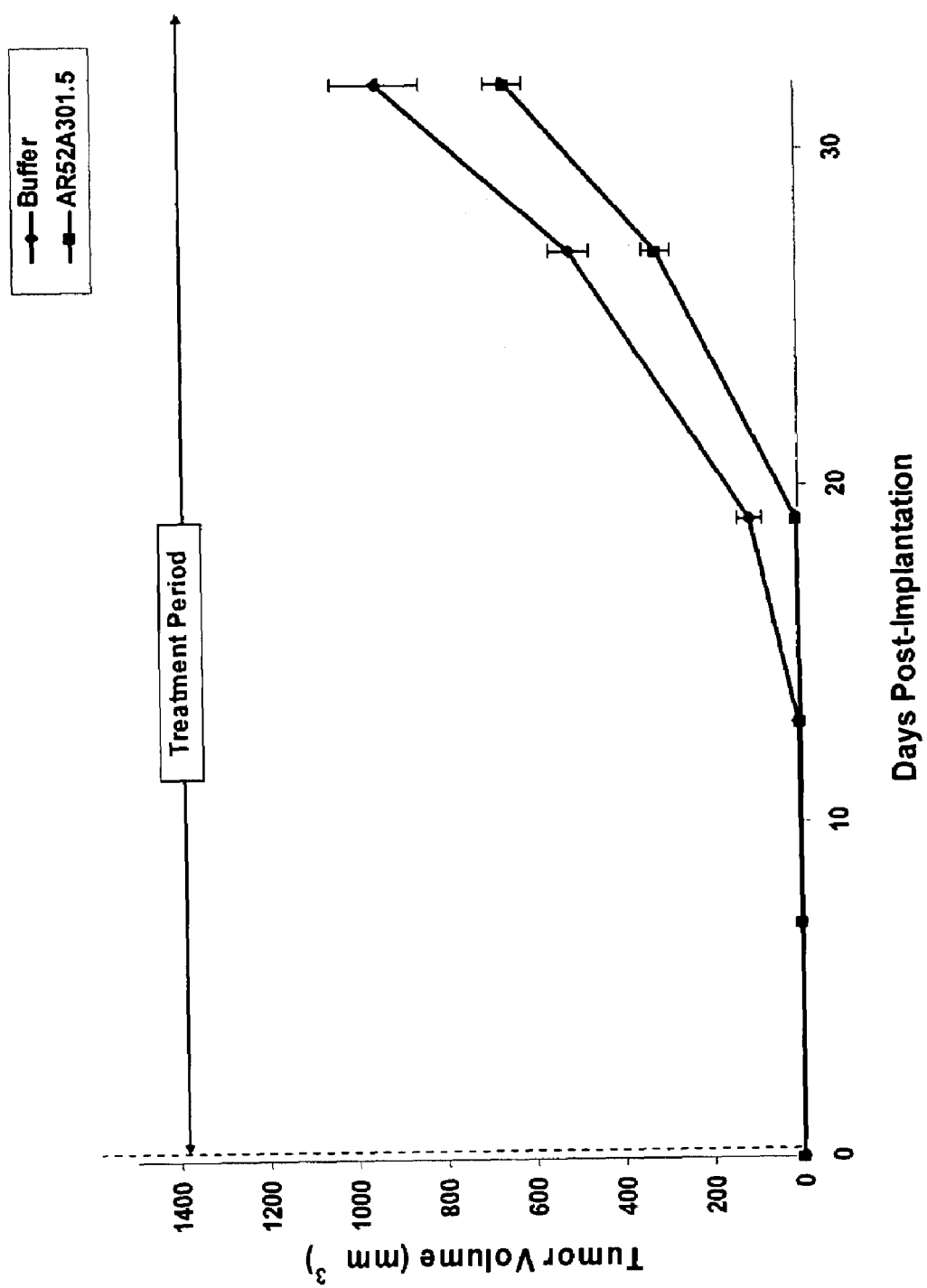
FIG. 11 demonstrates the effect of AR52A301.5 on tumor growth in a prophylactic PC-3 prostate cancer model. The vertical lines indicate the period during which the antibody was administered. Data points represent the mean +/– SEM.

Examples 3 and 4 demonstrated that AR52A301.5 had anti-cancer properties against a human pancreatic cancer cell line. To determine the efficacy of AR52A301.5 against another human pancreatic cell line, the antibody was tested on a xenograft model of PL45 human pancreatic cancer. With reference to FIGS. 8, 9, and 10, 8 to 10 week old female SCID mice were implanted with 5 million human pancreatic cancer cells (PL45) in 100 microliters PBS solution injected subcutaneously in the scruff of the neck. The mice were randomly divided into 2 treatment groups of 10. On the day after implantation, 20 mg/kg of AR52A301.5 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study. Tumor growth was measured about every 7 day with calipers. The study was completed after 9 doses of antibody. Body weights of the animals were recorded once per week for the duration of the study. At the end of the study all animals were euthanized according to CCAC guidelines.

AR52A301.5 significantly inhibited tumor growth in the PL45 in vivo prophylactic model of human pancreatic cancer cells. Treatment with ARIUS antibody AR52-A301.5 reduced the growth of PL45 tumors by 46.8 percent (p=0.00068, t-test), compared to the buffer treated group, as determined on day 77, 20 days after the last dose of antibody (FIG. 8) when almost all mice in control and antibody-treated group were still alive. The study was still ongoing at day 102, 45 days after last dose, at which point all mice in the control group had been removed from the study due to tumor volume. However, 40 percent of the mice in the AR52A301.5-treated group were still alive at this time-point (FIG. 9).

There was no obvious clinical signs of toxicity throughout the study. Body weight measured at weekly intervals was a surrogate for well-being and failure to thrive. The mean body weight increased in all groups over the duration of the study (FIG. 10). The mean weight gain between day 13 and day 77 was 3.39 g (17.4 percent) in the control group and 2.86 g (14.5 percent) in the AR52A301.5-treated group. There were no significant differences between the groups during the treatment period or at day 77, 20 days after last the dose.

In summary, AR52A301.5 was well-tolerated and significantly reduced the tumor growth in this human pancreatic cancer xenograft model at day 77. AR52A301.5 treatment also demonstrated increased survival in comparison to buffer treatment. AR52A301.5 therefore has demonstrated efficacy in two different models of human pancreatic cancer.

EXAMPLE 6

In Vivo Prophylactic Tumor Experiments with PC-3 Cells

Examples 3, 4 and 5 demonstrated that AR52A301.5 had anti-cancer properties against two different human pancreatic cancer xenograft models. To determine the efficacy of AR52A302.5 against a different human cancer xenograft model, the antibody was tested on a PC-3 prostate cancer xenograft model. With reference to FIGS. 11, 12, and 13, 8 to 10 week old female SCID mice were implanted with 5 million human prostate cancer cells (PC-3) in 100 microliters PBS solution injected subcutaneously in the scruff of the neck. The mice were randomly divided into 2 treatment groups of 10. On the day after implantation, 20 mg/kg of AR52A301.5 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study. Tumor growth was measured about every 7 day with calipers. The study was completed after 8 doses of antibody. Body weights of the animals were recorded once per week for the duration of the study. At the end of the study all animals were euthanized according to CCAC guidelines when reaching endpoint.

Figure 12:
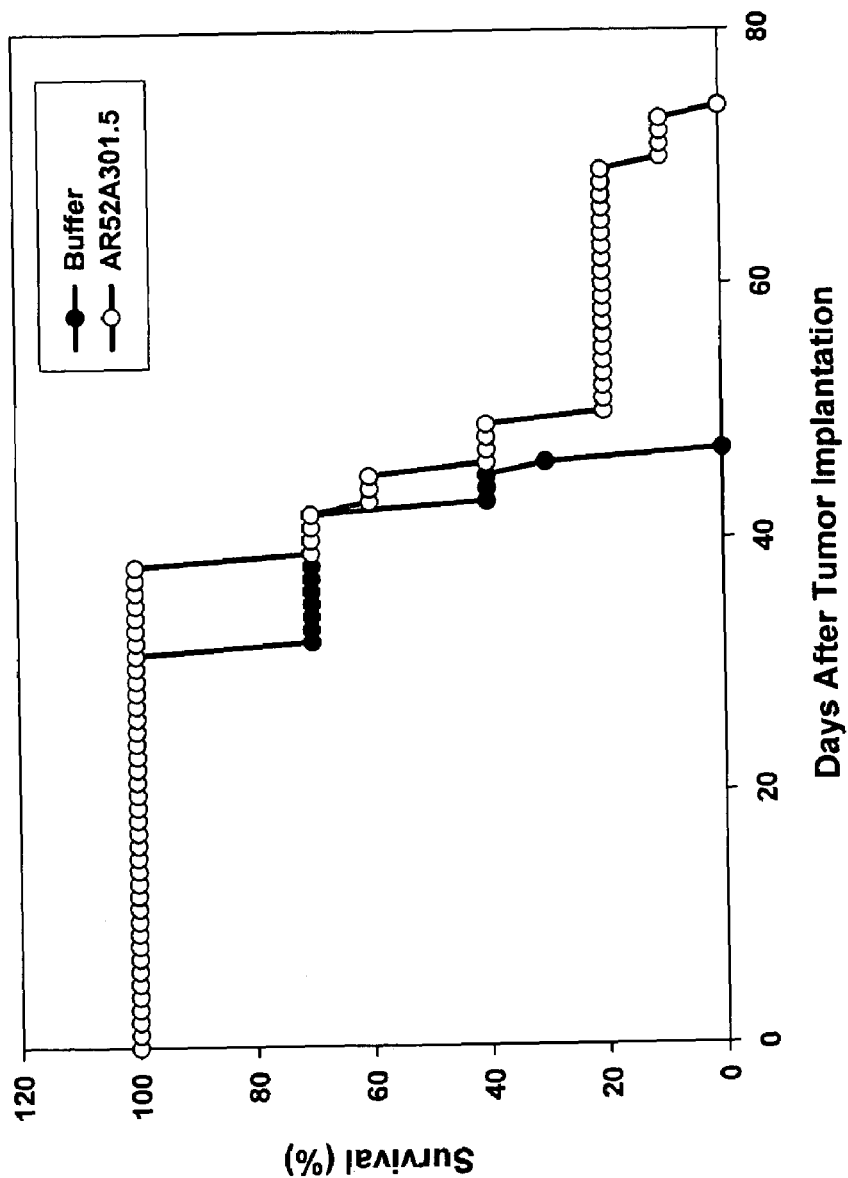
FIG. 12 demonstrates the effect of AR52A301.5 on survival in a prophylactic PC-3 prostate cancer model.

AR52A301.5 inhibited tumor growth in the PC-3 in vivo prophylactic model of human prostate cancer. Treatment with ARIUS antibody AR52A301.5 reduced the growth of PC-3 tumors by 30.9 percent (p=0.01443, t-test), compared to the buffer treated group, as determined on day 32 after 5 doses (FIG. 11) when almost all the mice in both the control and antibody-treated group were still alive. The study was still ongoing at day 47, 3 days before the last dose, at which point all mice in the control group had been removed from the study due to tumor volume/lesions. However, at this time-point 40 percent of the mice in AR52A301.5-treated group were still alive (FIG. 12).

Figure 13:
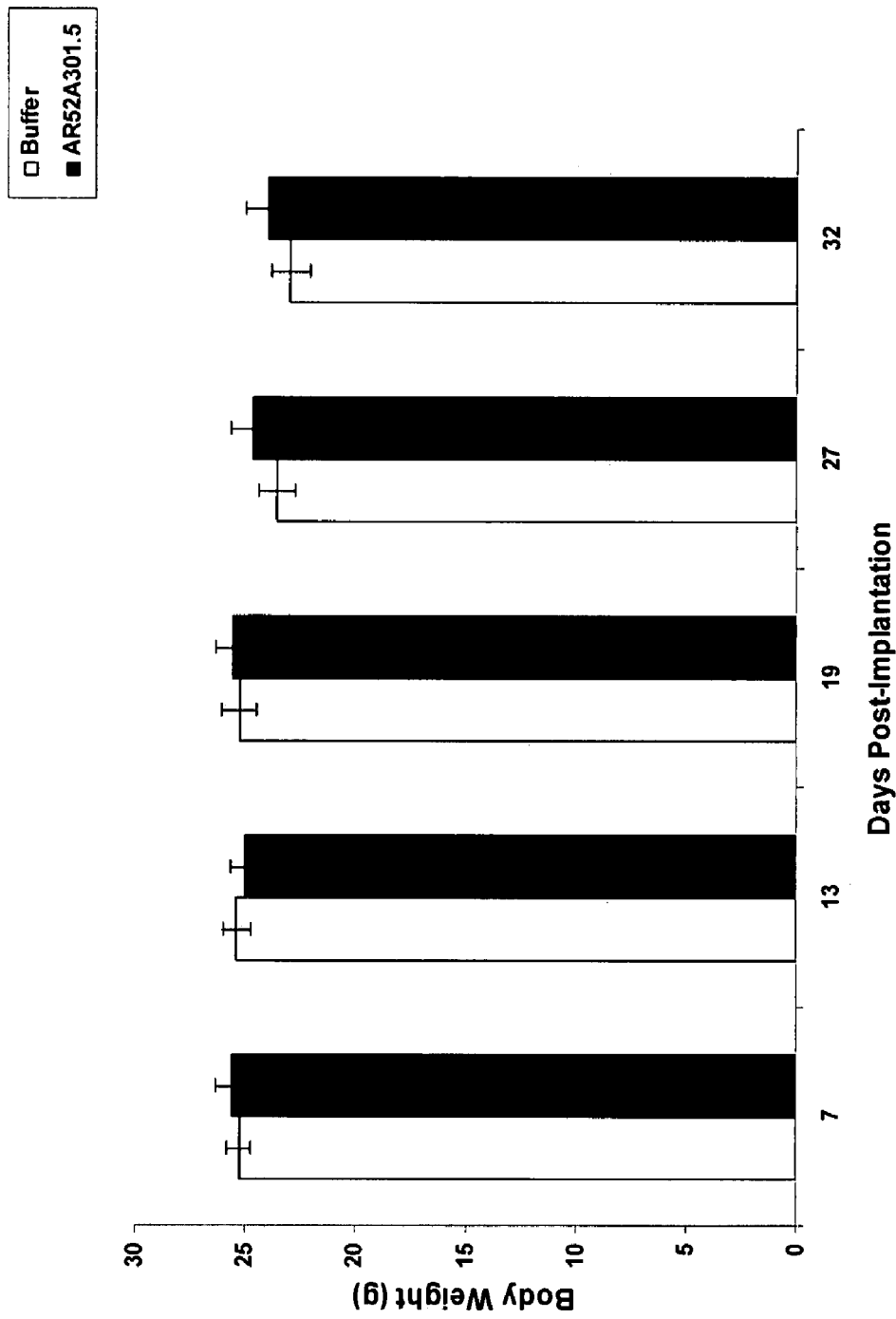
FIG. 13 demonstrates the effect of AR52A301.5 on body weight in a prophylactic PC-3 prostate cancer model. Data points represent the mean +/– SEM.

There were no obvious clinical signs of toxicity throughout the study. Body weight measured at weekly intervals was a surrogate for well-being and failure to thrive. The mean body weight remained relatively constant (FIG. 13). There was no significant difference between the groups during the treatment period and or at day 32, after 5 doses.

In summary, AR52A301.5 was well-tolerated and reduced the tumor growth in this human prostate cancer xenograft model. Treatment with antibody also demonstrated a survival benefit in comparison to the control group. AR52A301.5 has demonstrated efficacy against two different human cancer indications; pancreatic and prostate.

EXAMPLE 7

In Vivo Prophylactic Tumor Experiments With Colo 205 Cells

Examples 3, 4, 5 and 6 demonstrated that AR52A301.5 had anti-cancer properties against two different human pancreatic and a prostate cancer xenograft model. To determine the efficacy of AR52A302.5 against a different human cancer xenograft model, the antibody was tested on a Colo 205 colon cancer xenograft model. With reference to FIGS. 14 and 15, 8 to 10 week old female SCID mice were implanted with 5 million human colon cancer cells (Colo 205) in 100 microliters PBS solution injected subcutaneously in the right flank of each mouse. The mice were randomly divided into 2 treatment groups of 10. One day after implantation, 20 mg/kg of AR52A301.5 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the first two weeks and twice per week for another 3 weeks. Tumor growth was measured about every 3-4 days with calipers. The treatment was completed after 8 doses of antibody. Body weights of the animals were recorded when tumors were measured for the duration of the study. At the end of the study all animals were euthanized according to CCAC guidelines when reaching endpoint.

Figure 14:
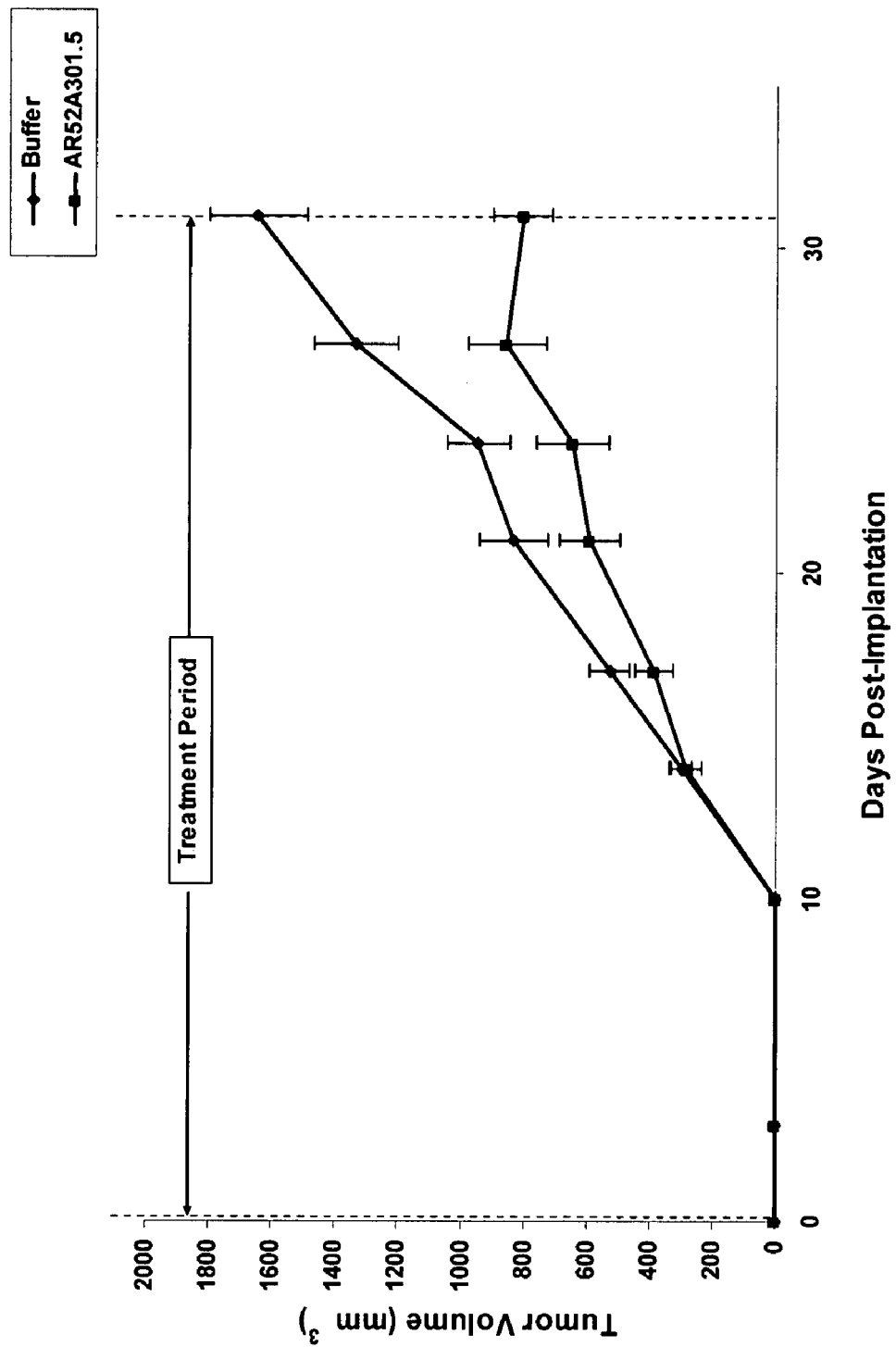
FIG. 14 demonstrates the effect of AR52A301.5 on tumor growth in a prophylactic Colo 205 colon cancer model. The vertical lines indicate the period during which the antibody was administered. Data points represent the mean +/– SEM.

AR52A301.5 significantly inhibited tumor growth in the Colo 205 in vivo prophylactic model of human colon cancer. Treatment with ARIUS antibody AR52A301.5 reduced the growth of Colo 205 colon tumors by 35.9 percent (p=0.01872, t-test), compared to the buffer treated group, as determined on day 27, 4 days before the last dose of antibody (FIG. 14).

Figure 15:
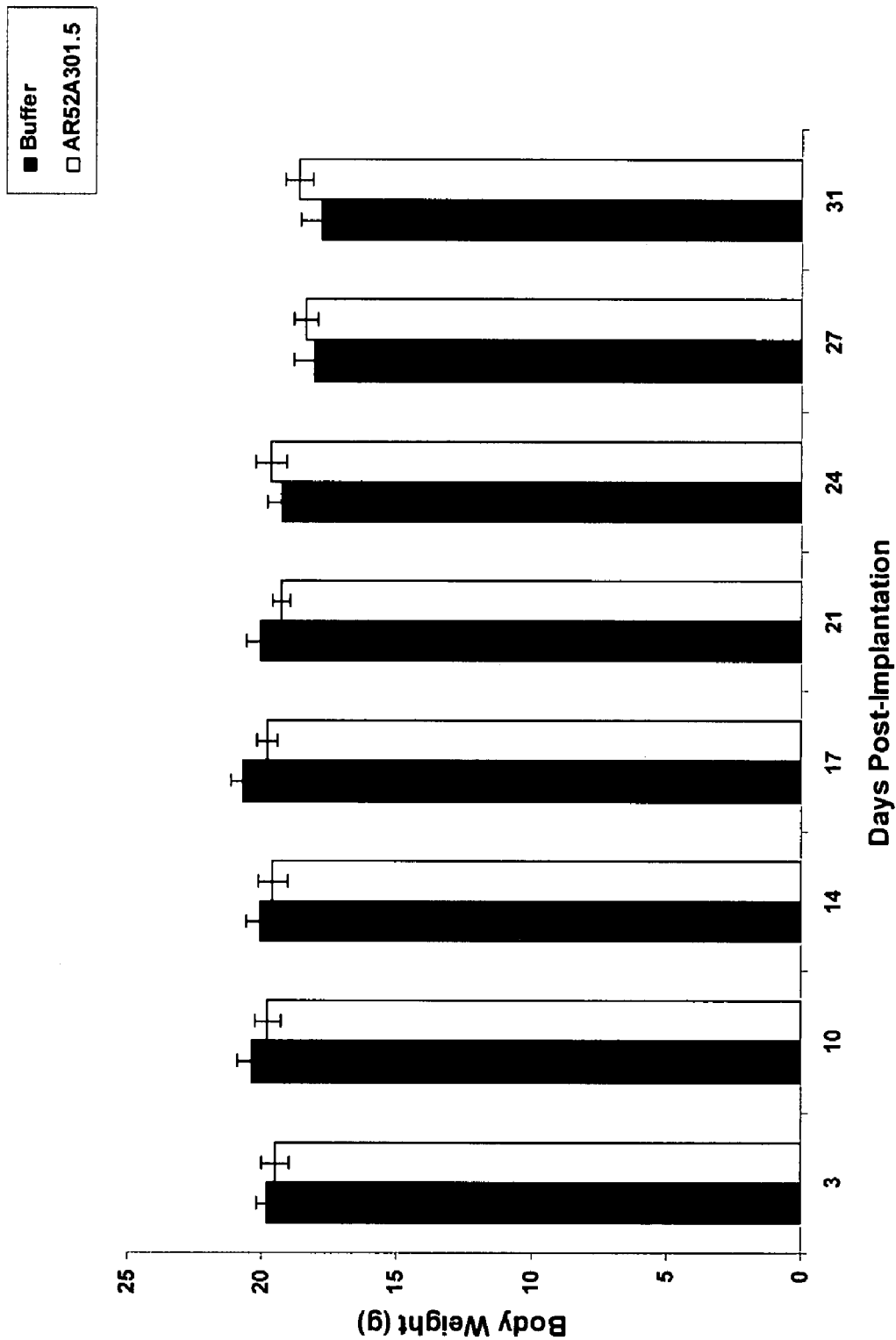
FIG. 15 demonstrates the effect of AR52A301.5 on body weight in a prophylactic Colo 205 colon cancer model. Data points represent the mean +/– SEM.

There were no obvious clinical signs of toxicity throughout the study. Body weight measured at weekly intervals was a surrogate for well-being and failure to thrive. There were no significant differences in mean body weight between the groups during the treatment period (FIG. 15).

In summary, AR52A301.5 was well-tolerated and significantly inhibited the tumor growth in this human colon cancer xenograft model. AR52A301.5 has demonstrated efficacy against three different human cancer indications; pancreatic, prostate and colon. Treatment benefits were observed in two different well-recognized models of human cancer disease suggesting pharmacologic and pharmaceutical benefits of this antibody for therapy in other mammals, including man.

EXAMPLE 8

Identification of Cross-Reactivity of Antibody AR52A301.5 with Human TROP-2

Figure 16:
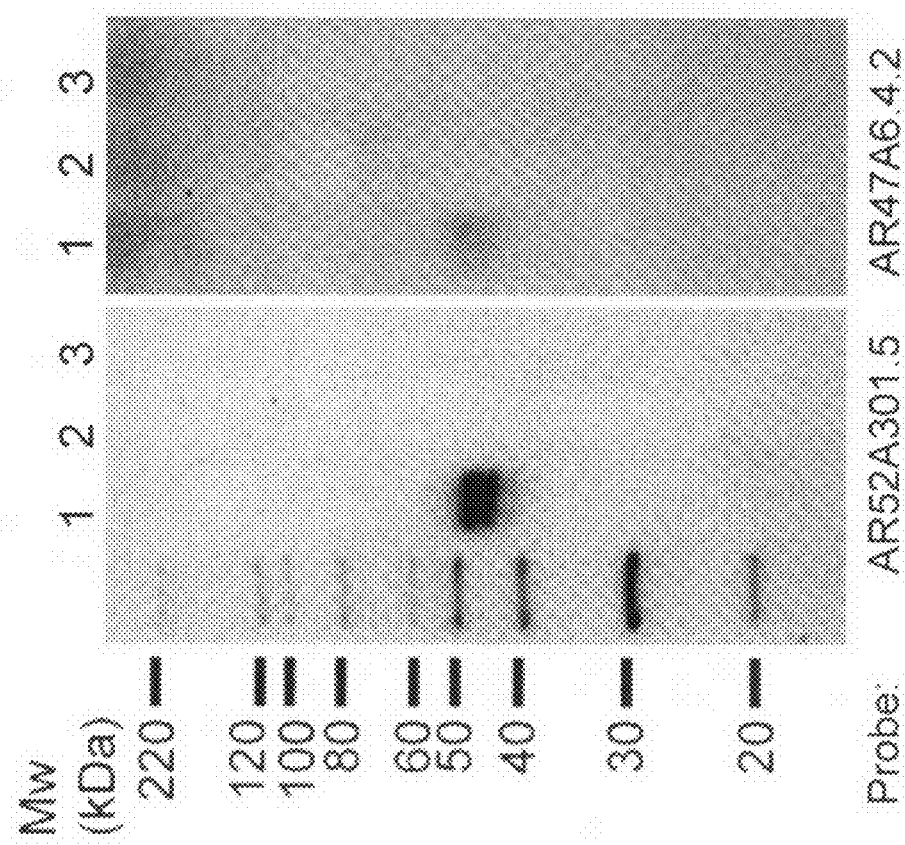
FIG. 16. Western blot of samples from the total membrane fraction of MDA-MB-231 cells (lane 1) and of whole cell lysates from PC-3 (lane 2) and CCD-27sk (lane 3) cell lines. Blots were probed with the AR47A6.4.2 and AR52A301.5. Molecular weight markers are indicated on the left.

Western blot results suggested that AR52A301.5 cross-reacted with a band of similar properties to that recognized by the antibody AR47A6.4.2 (known to bind to human TROP-2; FIG. 16). To further characterize the antigen recognized by AR52A301.5, this antibody was used as a probe on the Western blot of an immunocomplex prepared with AR47A6.4.2 from the total membrane fraction of MDA-MB-231 (MB-231) cells.

Total cell membranes were prepared from confluent cultures of MB-231 breast cancer cells. Media was removed from cell stacks and the cells were washed with phosphate buffered saline (PBS). Cells were dissociated with dissociation buffer (Gibco-BRL; Grand Island, N.Y.) for 20 minutes at 37° C. on a platform shaker. Cells were collected and centrifuged at 900 g for 10 minutes at 4° C. After centrifugation, cell pellets were washed by resuspending in PBS and centrifuging again at 900 g for 10 minutes at 4° C. Pellets were then stored at −80° C. until required. To prepare membranes, cell pellets were thawed and resuspended in homogenization buffer containing 1 tablet per 50 mL of complete protease inhibitor cocktail (Roche; Laval QC) at a ratio of 3 mL buffer per gram of cells. The cell suspension was subjected to homogenization using a polytron homogenizer on ice in order to lyse the cells. The cell homogenate was centrifuged at 15,000 g for 10 minutes at 4° C. to remove the nuclear particulate. Supernatant was harvested, divided into tubes and then centrifuged at 75,600 g for 90 minutes at 4° C. Supernatant was carefully removed and each membrane pellet was resuspended in approximately 5 mL of homogenization buffer. The membrane pellets from all tubes were combined, divided one more time, and centrifuged at 75,600 g for 90 minutes at 4° C. Supernatant was carefully removed and the pellets were weighed. Solubilization buffer containing 1 percent Triton X-100 was added to the pellets at a ratio of 3 mL buffer per gram of membrane pellet. Membranes were solubilized by shaking on a platform shaker at 300 rpm, for 1 hour on ice. The membrane suspension was centrifuged at 75,600 g to pellet insoluble material. The supernatant, containing the solubilized membrane proteins, was carefully removed from the tubes, assayed for protein concentration, and stored at −80° C.

Figure 17:
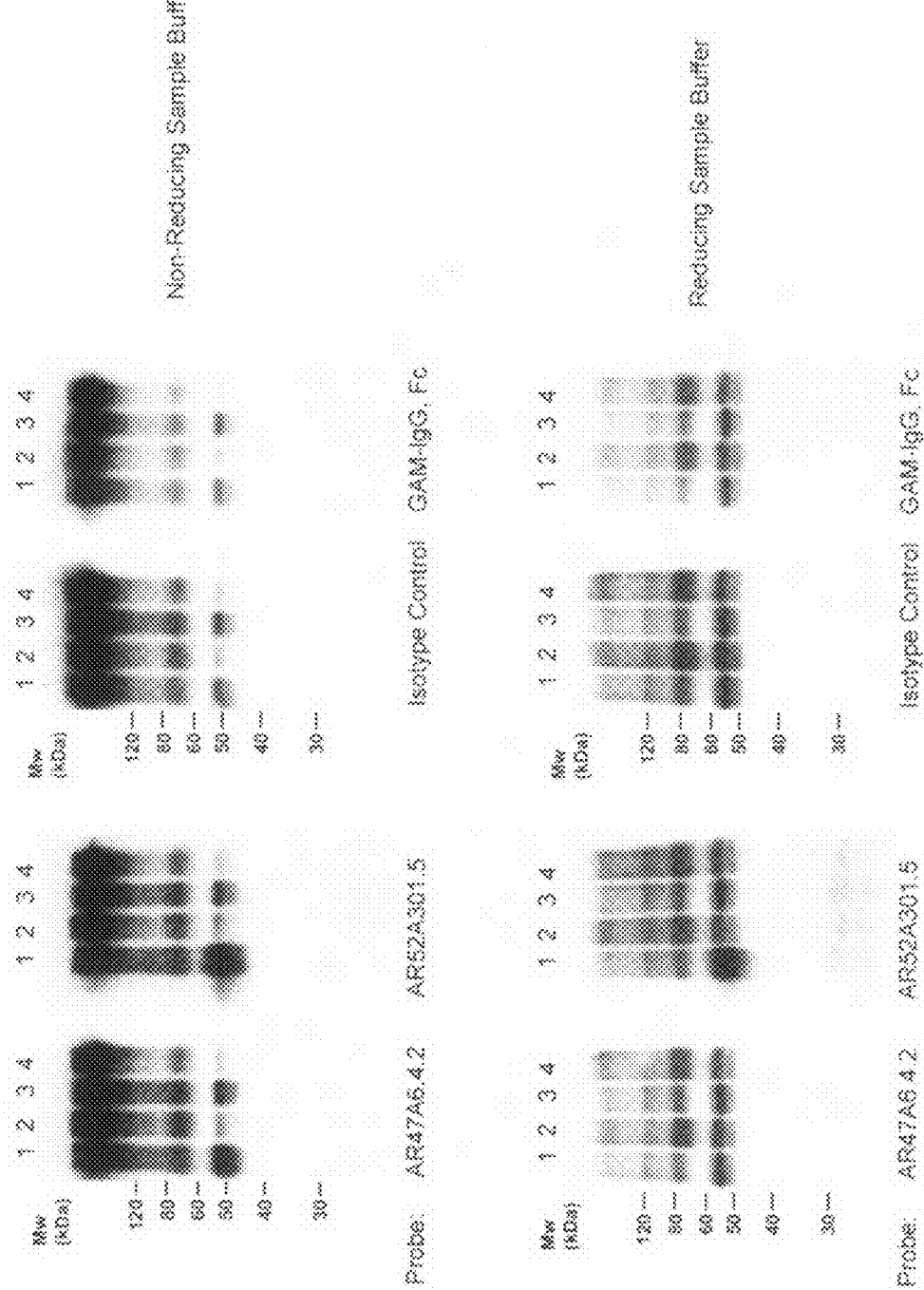
FIG. 17. Western blot of an immunocomplex prepared by immunoprecipitation with AR47A6.4.2 (lane 1) and with an isotype control (lane 2), from the total membrane fraction of the MDA-MB-231 cell line. Antibody-conjugated Protein G-Sepharose beads not incubated with total membrane fraction of MDA-MB-231 were also used as negative controls (lanes 3 and 4). Replicate blots were probed either with the antibodies AR47A6.4.2, AR52A301.5 (hybridoma supernatant), IgG2a isotype control or without primary antibody. Samples were analyzed by SDS-PAGE electrophoresis under reducing and non-reducing conditions. Molecular weight markers are indicated on the left.

Total membrane fraction of MB-231 was diluted with 1×RIPA buffer to a final protein concentration of 1 mg/mL. This sample was divided in two aliquots of identical size. Each aliquot was incubated with antibody-conjugated Protein G Sepharose, conjugated with either AR47A6.4.2 or with the 8A3B.6 isotype control antibody, for 2 hours at 4° C. After washing, each antibody-conjugated beads sample was divided in two identical aliquots. One of the sets of IP samples, and one set of each of AR47A6.4.2 and 8A3B.6 conjugated 'mock IP' beads were resuspended with 1× non-reducing SDS-PAGE sample buffer, and a second set was resuspended in 1× reducing SDS-PAGE sample buffer. After boiling an identical aliquot from each sample was loaded onto replicate lanes of 10 percent SDS-polyacrylamide gels. After SDS-PAGE the gels were transferred onto PVDF membranes and the latter blocked for 1 hour with 5 percent milk in TBST followed by incubation with the antibodies AR47A6.4.2, AR52A301.5, with the isotype control antibody 8A3B.6 or with no primary antibody, in blocking buffer, for 2 hours at room temperature. Blots were washed, as described above, and incubated with a horseradish peroxidase-conjugated goat anti-mouse IgG, Fc fragment-specific, diluted in blocking buffer, and incubated for 1 hour at room temperature. After washing as described above, the blots were developed with the ECL Plus reagent following the manufacturer's recommendations. The result from this experiment (FIG. 17) demonstrate that the antibody AR52A301.5 cross-reacted specifically with an antigen that is immunoprecipitated by AR47A6.4.2 and that had the same apparent molecular weight as the antigen recognized by the latter antibody. The results also show that the cross-reactivity of AR47A6.4.2, when used as a probe on a Western blot, is abolished by the boiling of the AR47A6.4.2 immunocomplexes with reducing SDS-PAGE sample buffer. However, cross-reactivity of AR52A301.5, with the same immunocomplexes under reducing conditions, was not detectably affected, suggesting that both antibodies may cross-react with different epitopes on the same antigen. While the epitope recognized by AR47A6.4.2 appears to be a disulfide-bond-dependent conformational epitope, that does not appear to be the case for the epitope recognized by AR52A301.5.

Figure 18:
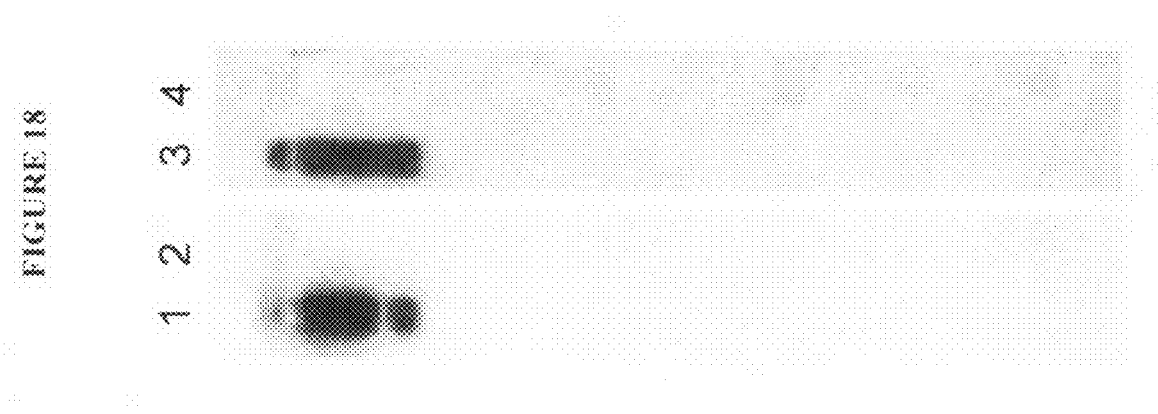
FIG. 18. Western blot of recombinant human TROP-2. Individual lanes were probed with the AR52A301.5 (lane 1) and AR47A6.4.2 (lane 3), and with isotype control antibodies (lanes 2 and 4).

In order to further establish the nature of the antigen recognized by the antibody AR52A301.5, Western blots of recombinant human TROP-2 (R&D Systems, Minneapolis, Minn.) prepared under non-reducing conditions for SDS-PAGE, were probed with AR52A301.5 and with AR47A6.4.2. The results from this experiment show (FIG. 18) that both AR47A6.4.2 and AR52A301.5 cross-reacted specifically with the recombinant TROP-2. Therefore we can conclude that the epitope recognized by the monoclonal antibody AR52A301.5 was also contained within the human TROP-2 antigen.

EXAMPLE 9

Deglycosylation Studies

In order to determine the effects of glycosylation on the binding of AR52A301.5, deglycosylation reactions were set up as per manufacturer's (Enzymatic Deglycosylation Kit, Prozyme, San Leandro, Calif.) instructions under both denaturing and non-denaturing conditions. For denaturing reactions, 0.4 micrograms recombinant TROP-2 (rhTROP-2; R&D Systems, Minneapolis, Minn.) or 100 micrograms of MDA-MB-231 membrane proteins (isolated as described above) were diluted to 30 microliters with water. 10 microliters of incubation buffer (5×, 0.25 M $NaH_2PO_4$, pH 7.0) and 2.5 microliters of denaturation solution (2 percent SDS, 1 M beta-mercaptoethanol) were added, and reactions were boiled for 5 minutes. Once reactions cooled to room temperature, 2.5 microliters of detergent solution (15 percent NP-40) and 1 microliter of each of the following enzymes were added: N-Glycanase® PNGase F (≧5 U/mL), Sialidase A™ (≧5 U/mL), O-Glycanase® (≧1.25 U/mL), beta(1-4) Galactosidase (3 U/mL) and beta-N-Acetylglucosaminidase (40 U/mL). Control reactions were included which contained 5 microliters of water instead of deglycosylation enzymes. For non-denaturing reactions, 0.4 micrograms rhTROP-2 or 100 micrograms of MDA-MB-231 membrane proteins were diluted to 35 microliters with water. 10 microliter of incubation buffer was added, along with 1 microliter of each enzyme listed above. Control reactions were included which contained 5 microliters of water instead of deglycosylation enzymes. All reactions were incubated at 37° C. for 24 hours.

Following deglycosylation, reactions were prepared for SDS-PAGE. 16.7 microliters of reducing or non-reducing sample loading buffer (4×) was added to the denatured and non-denatured reactions, respectively. Samples were boiled for 5 minutes, then cooled to room temperature. 16.7 microliters of each reaction was loaded onto quadruplicate 12 percent SDS-PAGE gels. Gels were run at 150 V until the dye front ran off. Proteins were transferred to PVDF membranes overnight at 40 V. Membranes were blocked with 5 percent milk prepared with TBST (Tris-buffered saline with 0.05 percent Tween-20) for 1 hour, followed by incubation with primary antibodies for 2 hours. Each primary antibody was diluted to 5 micrograms/mL in 5 percent milk, except anti-human TROP-2, which was diluted to 2 micrograms/mL. Blots were incubated with one of AR52A301.5, anti-human TROP-2 (R&D Systems, Minneapolis, Minn.) or IB7.11 (produced in-house) IgG1 isotype control. Following primary antibody incubation, blots were washed 3 times, 10 minutes each, with TBST. Blots were incubated with goat anti-mouse IgG Fc HRP secondary antibody diluted to 1:50,000 in 5 percent milk for 1 hour, then washed 3 times, 10 minutes each, with TBST. Blots were developed with ECL Plus Western Blotting Detection Reagents (GE Healthcare, Life Sciences formerly Amersham Biosciences; Piscataway, N.J.) and an X-ray developer.

Figure 19:
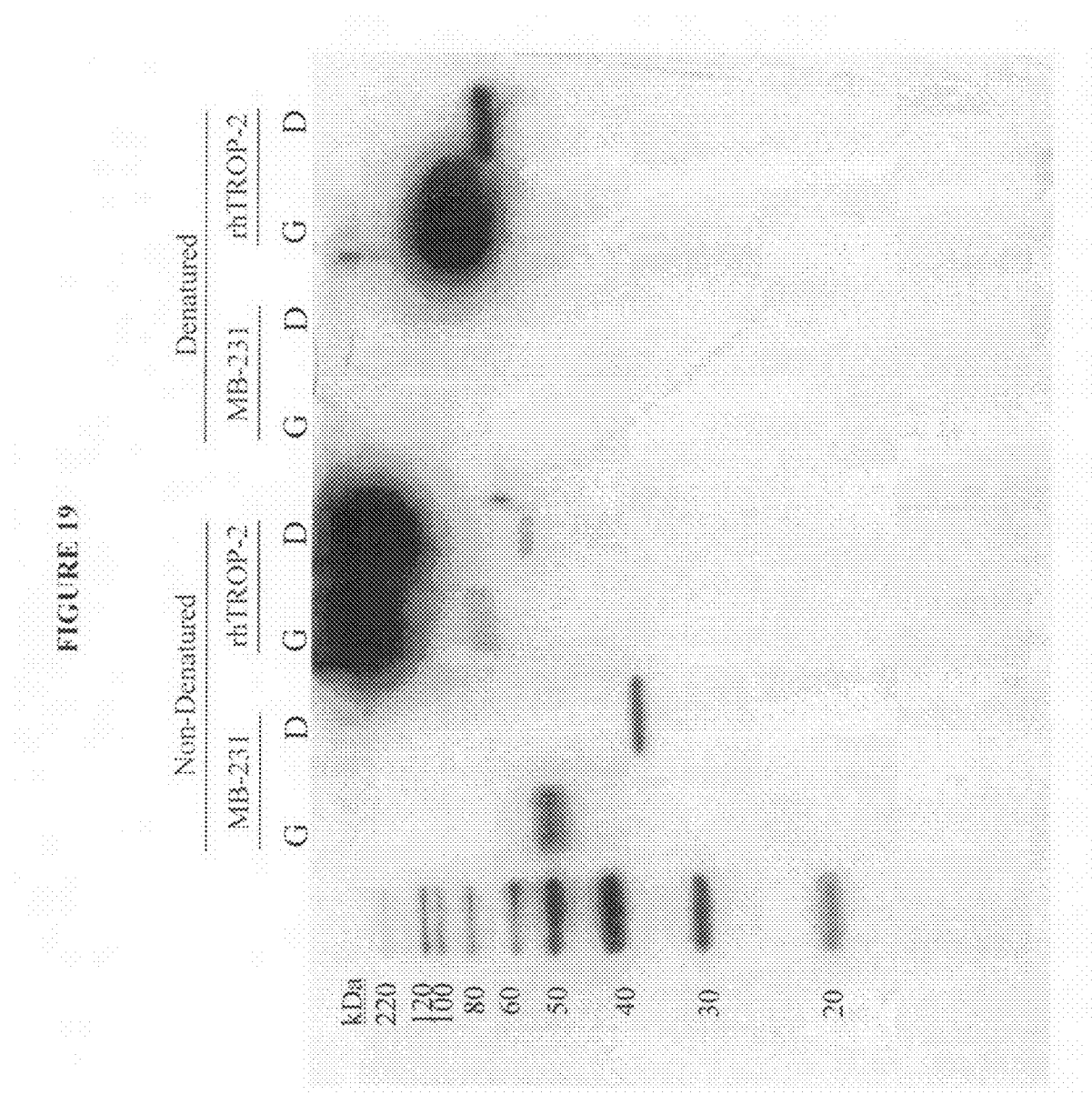
FIG. 19. MDA-MB-231 membrane proteins (MB-231) and recombinant human TROP-2 (rhTROP-2) glycosylated (G) and deglycosylated (D) under denaturing and non-denaturing conditions, probed with AR52A301.5.
Figure 20:
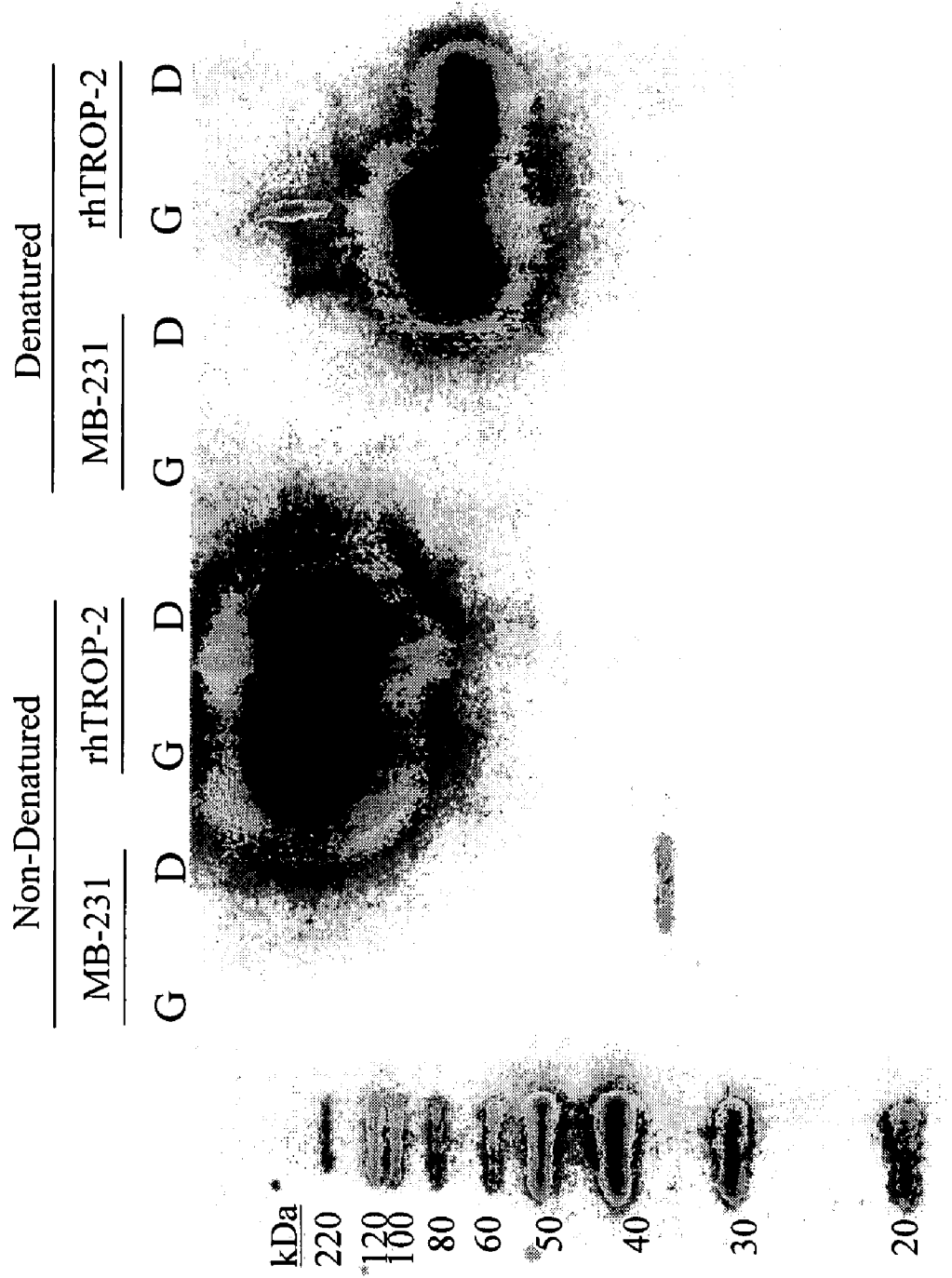
FIG. 20. MDA-MB-231 membrane proteins (MB-231) and recombinant human TROP-2 (rhTROP-2) glycosylated (G) and deglycosylated (D) under denaturing and non-denaturing conditions, probed with anti-human TROP-2.
Figure 21:
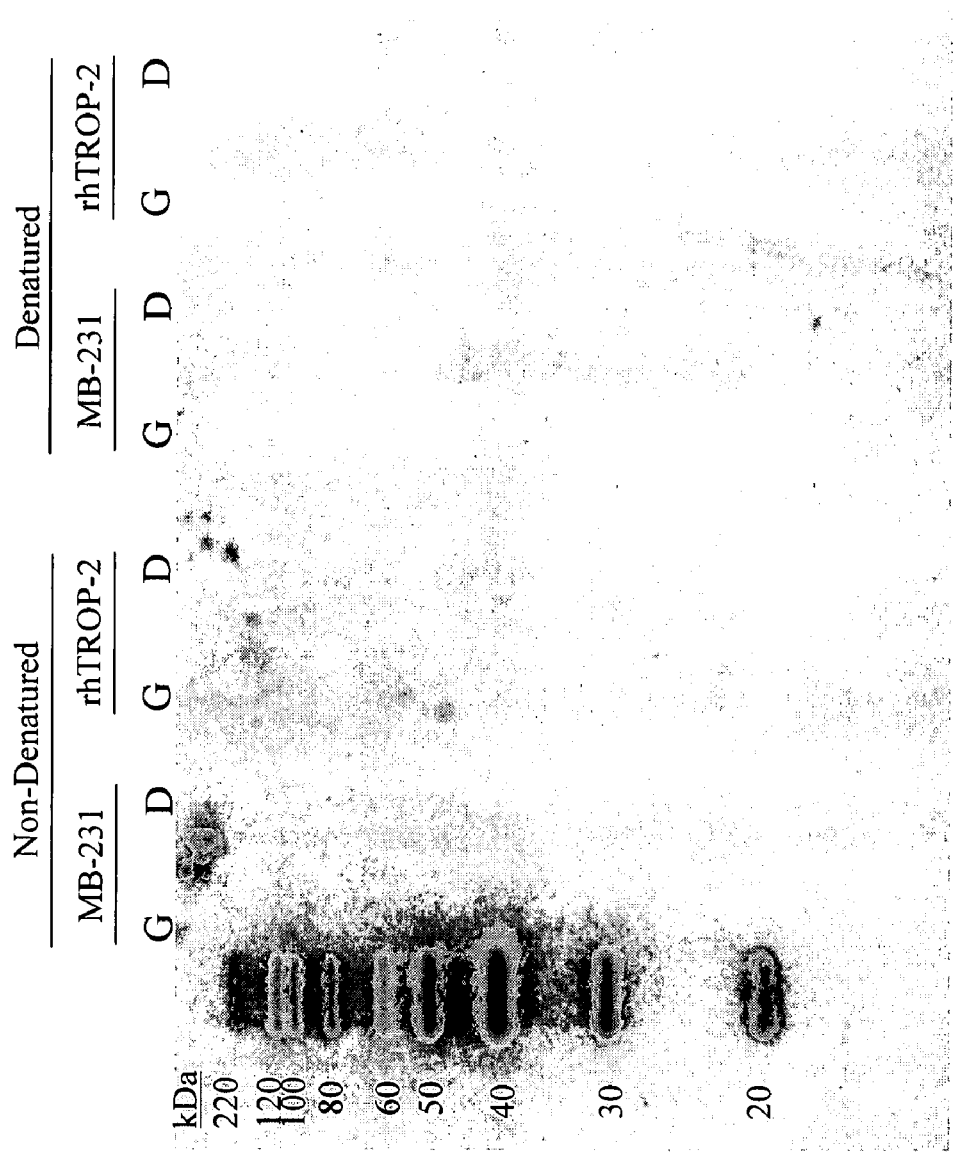
FIG. 21. MDA-MB-231 membrane proteins (MB-231) and recombinant. human TROP-2 (rhTROP-2) glycosylated (G) and deglycosylated (D) under denaturing and non-denaturing conditions, probed with 1B7.11 IgG1 isotype control.

FIGS. 19-21 show the results of the 3 blots probed with AR52A301.5, anti-human TROP-2 and 1B7.11 $IgG_1$ isotype control respectively. FIG. 19 (blot probed with AR52A301.5) shows a band of similar size in lane 1. This band is not detectable in FIG. 20 (blot probed with anti-human TROP-2). The reactive band in the sample from lane 2 (non-denatured and deglycosylated MB-231 total membrane fraction) shows a shift to around 37 kDa and was recognized by AR52A301.5 (FIG. 19) and by the commercial anti-TROP-2 antibody (FIG. 20) blot, but not by the isotype control (FIG. 21). No bands were detected in lanes 5 or 6 (denatured and non-deglycosylated and deglycosylated MB-231 total membrane fraction) in any of the blots, indicating that the antibodies did not detectably bind to the target protein in the total membrane fraction under reducing conditions.

Recombinant human TROP-2 appears as a very intense, very high molecular weight band (apparent molecular weight larger than 220 kDa) in lanes 3 and 4 (non-denatured non-deglycosylated and deglycosylated rhTROP-2, respectively) in FIGS. 19 and 20 (blots probed with AR52A301.5 and anti-human TROP-2, respectively) and correspond to disulfide-bond linked multimers of rhTROP-2. Less intense bands appear at ~70 kDa in lane 3 (non-denatured non-deglycosylated rhTROP-2) and ~55 kDa in lane 4 (non-denatured and deglycosylated rhTROP-2) in FIG. 19 (blot probed with AR52A301.5) and correspond to the monomeric forms of rhTROP-2. The shift in apparent molecular weight of both the multimer and monomer bands from larger than 220 kDa and 70 kDa to lower than 220 kDa and 55 kDa, respectively (lanes 3 and 4) result form the loss of carbohydrate groups due to deglycosylation. Under reducing conditions (lanes 7 and 8), rhTROP-2 is detected only as the smaller monomeric polypeptide, with a decrease of approximately 20 kDa in apparent molecular weight upon treatment with the glycosidase mixture (FIG. 20). FIG. 21 (blot probed with the isotype control antibody 1B7.11) does not display reactivity in any of the lanes.

All the anti-human TROP-2 antibodies used, AR52A301.5 and the commercial anti-human TROP-2 antibody, recognized the human TROP-2 antigen in a total membrane preparation from MDA-MB-231, and the purified recombinant human TROP-2, prior to, and after, treatment with a mixture of glycosidases. This result suggests that the antibodies may recognize a non-carbohydrate epitope, possibly a polypeptide epitope, although it is not possible to rule out that binding may be occurring to a carbohydrate group that was not removed by the particular mixture of glycosidases used in this experiment.

EXAMPLE 10

Competition Experiments

In order to further characterize the binding properties of AR47A6.4.2 and AR52A301.5, antibody competition experiments were carried out by Western blot to determine if AR47A6.4.2 and AR52A301.5 recognize similar or distinct epitopes of TROP-2. Two micrograms of recombinant fusion polypeptides containing the extracellular domain of human TROP-2 and the Fc region of human IgG1, and expressed by the mouse myeloma cell line NSO (R&D Systems, Minneapolis, Minn.) were subjected to SDS-PAGE under non-reducing conditions using preparative well combs that spanned the entire length of each of two 10 percent polyacrylamide gels. The proteins from the gels were transferred to PVDF membranes at 40V for approximately 17 hours at 4° C. The membranes were blocked with 5 percent skim milk in TBST for one hour at room temperature on a rotating platform. The membranes were washed twice with approximately 20 mL of TBST and were placed in a Western multiscreen apparatus creating twenty separate channels in which different probing solutions were applied. Previously, biotinylated AR47A6.4.2 and AR52A301.5 had been prepared using EZ-Link NHS-PEO Solid Phase Biotinylation Kit (Pierce, Rockford, Ill.). Primary antibody solutions were prepared by mixing biotinylated AR47A6.4.2 or biotinylated AR52A301.5 with varying concentrations of non-biotinylated antibodies. Specifically, solutions were prepared containing 0.05 micrograms/mL of biotinylated AR52A301.5 in 3 percent skim milk in TBST plus 0.5 micrograms/mL, 5 micrograms/mL, 50 micrograms/mL, 500 micrograms/mL or 1000 micrograms/mL of non-biotinylated antibody. The non-biotinylated antibodies that were used were AR52A301.5, AR47A6.4.2 and control antibody 8A3B.6 (anti-bluetongue virus; IgG2a, kappa, purified in-house). Solutions containing 0.05 micrograms/mL of biotinylated AR47A6.4.2 were prepared with the same concentrations listed above of the non-biotinylated antibodies AR52A301.5, AR47A6.4.2 and control antibody 1B7.11 (anti-TNP; IgG1, kappa, 20 µg/mL, purified in-house). A negative control solution consisting of three percent skim milk in TBST was added to two channels on each membrane.

The primary antibody solutions were incubated in separate channels on the membranes for 2 hours at room temperature on a rocking platform. Each channel was washed 3 times with TBST for ten minutes on a rocking platform. Secondary solution consisting of 0.01 micrograms/mL peroxidase conjugated streptavidin (Jackson Immunoresearch, West Grove Pa.) in 3 percent skim milk in TBST was applied to each channel on the membrane, except for one channel on each membrane to which 3 percent milk in TBST alone was applied as a negative control. The membranes were incubated in secondary solution for 1 hour at room temperature on a rocking platform. Each channel was washed 3 times with TBST for ten minutes on a rocking platform. The membranes were removed from the multiscreen apparatus and incubated with an enhanced chemiluminescence detection solution (GE Healthcare, Life Sciences formerly Amersham Biosciences; Piscataway, N.J.) according to manufacturer's directions. The membranes were then exposed to film and developed.

Figure 22:
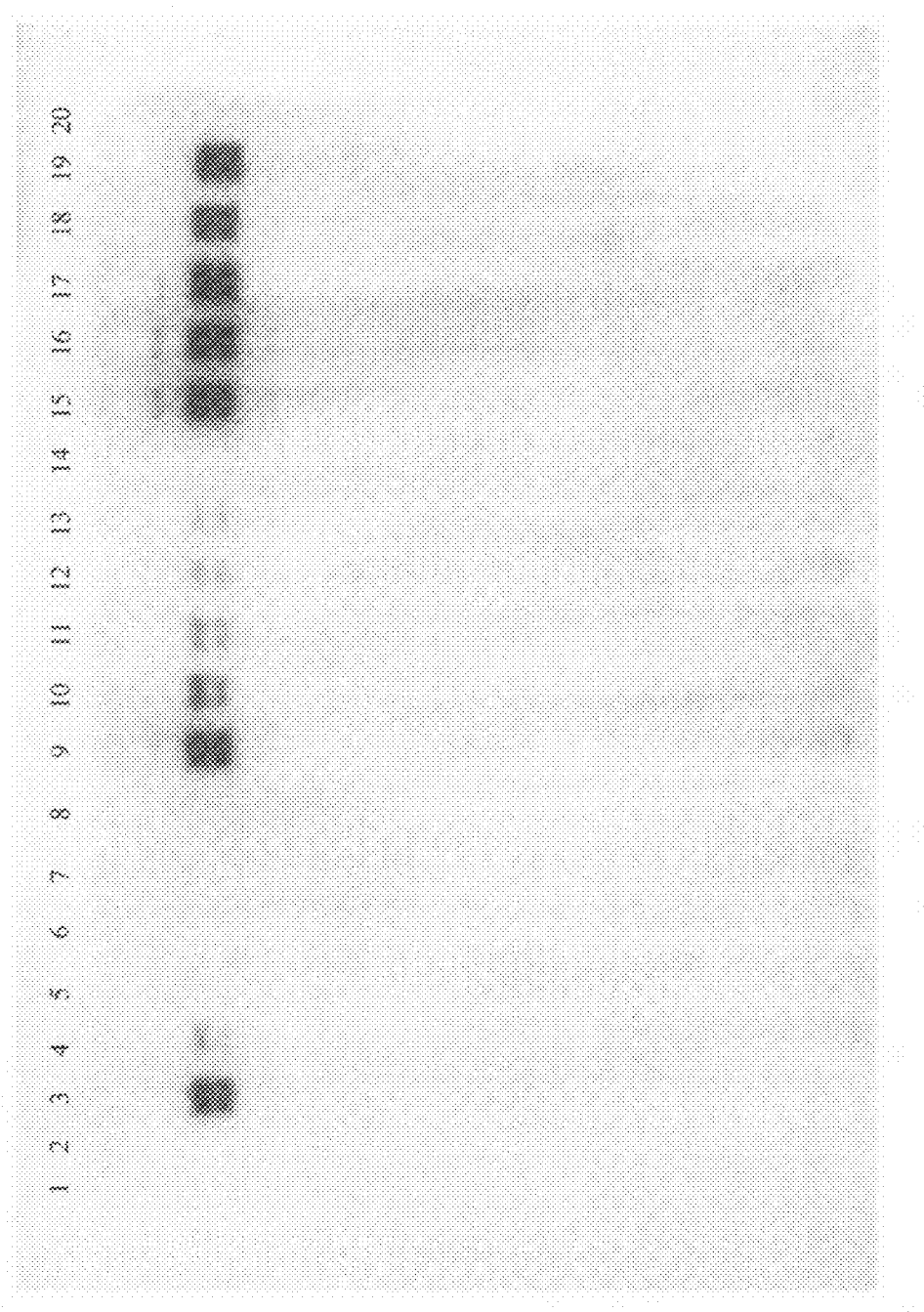
FIG. 22. Western blot of recombinant human TROP-2 probed with different primary antibody solutions. Lanes 3 to 7 were probed with biotinylated AR52A301.5 mixed with 0.5 microgram/mL, 5 microgram/mL, 50 microgram/mL, 500 microgram/mL and 1000 microgram/mL of non-biotinylated AR52A301.5 respectively. Lanes 9 to 13 were probed with biotinylated AR52A301.5 mixed with 0.5 microgram/mL, 5 microgram/mL, 50 microgram/mL, 500 microgram/mL and 1000 microgram/mL of non-biotinylated AR47A6.4.2 respectively. Lanes 15 to 19 were probed with biotinylated AR52A301.5 mixed with 0.5 microgram/mL, 5 microgram/mL, 50 microgram/mL, 500 microgram/mL and 1000 microgram/mL of non-biotinylated 8A3B.6 respectively. Lanes 8 and 14 were incubated with negative control solution and lane 8 was not incubated in secondary solution. Lanes 1, 2 and 20 were incubated with TBST only.

FIGS. 22 and 23 show the results of the antibody competition experiments. Binding of the biotinylated AR52A301.5 was completely inhibited at a concentration of 50 micrograms/mL and greater of non-biotinylated AR52A301.5 (1000× excess; FIG. 22 lanes 3-7) while the binding of AR47A6.4.2 was completely inhibited at a concentration of 500 micrograms/mL and greater of non-biotinylated AR47A6.4.2 (10000× excess; FIG. 23 lanes 9-13). The binding of biotinylated AR52A301.5 was not inhibited in any of the samples containing IgG2a isotype control antibody (FIG. 22 lanes 15-19). and the binding of biotinylated AR47A6.4.2 was not inhibited in any of the samples containing IgG1 isotype control antibody (FIG. 23 lanes 15-19). This indicates that the inhibition of binding observed with the biotinylated antibodies mixed with the same non-biotinylated antibody was due to the occupation of antigen binding sites by the non-biotinylated antibody, not by non-specific interactions of excess antibody alone. The binding of biotinylated AR52A301.5 was not completely inhibited in any of the samples containing AR47A6.4.2, and the binding of biotinylated AR47A6.4.2 was not completely inhibited in any of the samples containing AR52A301.5. In both Western blots however, the reactivity of each biotinylated TROP-2 antibody at 5 micrograms/mL, 50 micrograms/mL, 500 micrograms/mL, and 1000 micrograms/mL of the other non-biotinylated TROP-2 antibody was less intense than in the corresponding lanes of excess isotype control antibody. These results indicate that the binding of AR52A301.5 does not prevent the binding of AR47A6.4.2 to TROP-2 and vice versa. Overall, the results of the competition Western blots suggest that the epitopes of the TROP-2 molecule that are recognized by AR47A6.4.2 and AR52A301.5 are distinct from one and other, although the binding of one antibody does affect the binding of the other.

EXAMPLE 11

Human Normal Tissue Staining

IHC studies were conducted to characterize the AR52A301.5 antigen distribution in human normal tissues. Slides were postfixed for 10 minutes in cold (−20° C.) acetone and then allowed to come to room temperature. Slides were rinsed in 4° C. cold phosphate buffered saline (PBS) 3 times for 2 minutes each followed by blocking endogenous peroxidase activity with washing in 3 percent hydrogen peroxide for 10 minutes. Slides were then rinsed in PBS 3 times for 5 minutes followed by incubation in Universal blocking solution (Dako, Toronto, Ontario) for 5 minutes at room temperature. AR52A301.5, anti-human muscle actin (Clone HHF35, Dako, Toronto, Ontario), anti-TROP-2 clone 77220.11 (R&D System Inc., Minn., USA) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 micrograms/mL for each antibody except for anti-actin which was 0.5 micrograms/mL and commercial TROP-2 was 1 microgram/mL) and incubated overnight for 1 hour at room temperature. The slides were washed with PBS 3 times for 2 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100 percent) and cleared with xylene. Using mounting media (Dako Faramount, Toronto, Ontario) the slides were coverslipped. Slides were microscopically examined using an Axiovert 200 (Ziess Canada, Toronto, ON) and digital images acquired and stored using Northern Eclipse Imaging Software (Mississauga, ON). Results were read, scored and interpreted by a histopathologist.

Binding of antibodies to 12 human normal organs, ovary, pancreas, thyroid, brain (cerebrum, cerebellum), lung, spleen, uterus, cervix, heart, skin, and skeletal muscle was performed using a human normal tissue screening array (Biochain, Calif., USA). The tissue microarray contained 20 human normal organs; however, 8 of them were uninterruptible either due to detachment or background staining. FIG. 24 presents a summary of the results of AR52A301.5 staining of an array of human normal tissues. AR52A301.5 showed restricted binding to epithelial tissues (endothelium of blood vessels, follicular epithelium of thyroid, acinar and ductal epithelium of pancreas, alveolar epithelium of lung, and epidermal keratinocytes of skin). The antibody also showed equivocal binding to lymphoid tissue of the spleen and negative binding to neural tissue of the brain (FIG. 25). Cellular localization was cytoplasmic and membranous with diffuse staining pattern. AR52A301.5 showed more restricted binding to human normal tissues than the commercial anti-TROP-2 antibody.

EXAMPLE 12

Multi-Tumor Tissue Staining

IHC studies were conducted to characterize the AR52A301.5 antigen prevalence in human cancers. Slides were transferred from −80 to −20° C. After one hour the slides were postfixed for 10 minutes in cold (−20° C.) acetone and then allowed to come to room temperature. Slides were rinsed in 4° C. cold phosphate buffered saline (PBS) 3 times for 2 minutes each followed by blocking endogenous peroxidase activity with washing in 3 percent hydrogen peroxide for 10 minutes. Slides were then rinsed in PBS 3 times for 5 minutes followed by incubation in Universal blocking solution (Dako, Toronto, Ontario) for 5 minutes at room temperature. AR52A301.10, anti-cytokeratin 7 clone OV-TL 12/30 (Dako, Toronto, Ontario), or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration 5 micrograms/mL for each antibody except for anti-actin which was 0.5 microgram/mL and anti-cytokeratin 7 which was ready to use and incubated for 1 hour at room temperature. The slides were washed with PBS 3 times for 2 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanol (75-100 percent) and cleared with xylene. Using mounting media (Dako Faramount, Toronto, Ontario) the slides were coverslipped. For the pancreatic array (Tri Star, Rockville, Md.) the same protocol was followed except for the following modifications. The tissue sections were initially air dried at room temperature for 2 hours and air dried again for 30 minutes after fixation with acetone. The endogenous hydrogen peroxide was blocked using 3 percent hydrogen peroxide in methanol for 15 minutes; this step was done after the primary antibody incubation.

Slides were microscopically examined using an Axiovert 200 (Ziess Canada, Toronto, ON) and digital images acquired and stored using Northern Eclipse Imaging Software (Empix, Mississauga, ON). Results were read, scored and interpreted by a histopathologist.

FIG. 26 presents a summary of the results of AR52A301.5 staining of various human tumors and their corresponding normal tissue sections (8 colon cancers, 9 ovarian cancers and 2 normal ovary, 10 breast cancers and 3 normal breast, 9 lung cancers and 2 normal lung, 13 prostate cancers and 3 normal prostate, and 13 pancreatic cancers and 4 normal pancreas). The tissues were distributed on three different tissue microarrays (Tri Star, Rockville, Md.). The AR52A301.5 antibody showed moderate to strong binding to 4/8 (50 percent), 7/9 (78 percent), 7/10 (70 percent), 6/9 (67 percent), 12/13 (92 percent) and 2/13 (15 percent) of colon, ovarian, breast, lung, prostate and pancreatic cancers, respectively (FIG. 27). In addition, equivocal to weak binding was observed in 3/8 (38 percent), 1/9 (11 percent), 3/10 (30 percent), 3/9 (33 percent), and 1/13 (8 percent) colon, ovarian, breast, lung and pancreatic cancer sections, respectively. In all of the tested tumors, the binding was specific for the tumor cells. For the corresponding normal tissues, the antibody showed no binding to 2/2 ovarian and 1/3 breast tissues. Equivocal to weak binding to 1/2 lung and 4/4 pancreatic normal tissues and moderate to strong binding to 2/3 breast, 1/2 lung and 3/3 prostate normal tissues was also observed. The binding was restricted to epithelial tissues of the normal organs. The positive control antibodies anti-cytokeratin-7 or anti-actin showed the expected positive binding to epithelial and muscular tissues, respectively. The negative IgG isotype control showed no detectable binding to any of the tested tissues.

EXAMPLE 13

Multi-Species Tissue Staining

IHC studies were conducted to characterize the AR52A301.5 antigen cross reactivity in frozen normal tissues of various species in order to select a preclinical toxicology model. Sections of SCID mouse normal tissues (harvested in house), a rat normal tissue array (Biochain, Calif., USA), a multi-species brain array (Biochain, Calif., USA) and a multi-species liver array (Biochain, Calif., USA) were transferred from −80 to −20 ° C. After one hour the slides were post fixed for 10 minutes in cold (−20° C.) acetone and then allowed to come to room temperature. Slides were rinsed in 4° C. cold phosphate buffered saline (PBS) 3 times for 2 minutes each followed by blocking endogenous peroxidase activity with washing in 3 percent hydrogen peroxide for 10 minutes. Slides were then rinsed in PBS 3 times for 5 minutes followed by incubation in Universal blocking solution (Dako, Toronto, Ontario) for 5 minutes at room temperature. AR52A301.5, anti-Grp94 (Stressgen, Victoria, BC, Canada), anti-human muscle actin (Clone HHF35, Dako, Toronto, Ontario) or isotype control antibody (directed towards *Aspergillus niger* glucose oxidase, an enzyme which is neither present nor inducible in mammalian tissues; Dako, Toronto, Ontario) was diluted in antibody dilution buffer (Dako, Toronto, Ontario) to its working concentration (5 micrograms/mL for each antibody except for anti-actin which was 0.5 microgram/mL) and incubated for 1 hour at room temperature. The slides were washed with PBS 3 times for 2 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100 percent) and cleared with xylene. Using mounting media (Dako Faramount, Toronto, Ontario) the slides were coverslipped. For the human, cynomolgus, rabbit, hamster and rhesus individual sections (Biochain, Calif., USA) the same protocol was followed with the following modifications. For the first step, the tissue sections were air dried at room temperature for 30 minutes and then washed with cold PBS without acetone fixation (the sections were acetone fixed from the manufacturer). The endogenous hydrogen peroxide was blocked using 3 percent hydrogen peroxide in methanol for 20 minutes; this step was done after the primary antibody incubation.

Immunoreactivity of the primary antibodies was detected/visualized with anti-mouse HRP conjugated secondary antibodies as supplied (Dako Envision System, Toronto, Ontario) for 30 minutes at room temperature. Slides were microscopically examined using an Axiovert 200 (Ziess Canada, Toronto, ON) and digital images acquired and stored using Northern Eclipse Imaging Software (Mississauga, ON). Results were read, scored and interpreted by a histopathologist.

Binding of the antibodies to a panel of SCID mouse normal tissues (harvested in house), brain tissues of rat, guinea pig, goat, sheep, chicken, cow, horse, dog and pig (Biochain, Calif., USA), liver tissues from rat, goat, chicken and cow (Biochain, Calif., USA) and human, cynomolgus, rhesus, rabbit, hamster and guinea pig individual tissue sections (Biochain, Calif., USA) was determined. The positive control antibody anti-actin (Clone HHF35, Dako, Toronto, Ontario) showed the expected specific binding to muscular tissues. The positive control antibody anti-Grp94 (Stressgen, Victoria, BC) showed the expected positive binding to predominantly the-epithelial tissues. The isotype negative control antibody (Dako, Toronto, Ontario) generally showed no detectable binding to the tested tissues. Tissue sections that showed obvious background staining in the negative control were excluded from interpretation.

FIG. 28 shows the tabulated results of AR52A301.5 staining of the human and various species normal tissues. AR52A301.5 showed no binding to the tested rabbit, mouse, rat, guinea pig, goat, sheep, hamster, chicken, cow, horse or pig normal tissues. For the normal dog tissues, there was dissimilar binding to that observed in the corresponding human tissues. For the cynomolgus normal tissues, AR52A301.5 showed similar tissue specificity as observed in the corresponding human tissues (FIG. 29) for all of the tested organs except for the ovary in which no binding was observed in cynomolgus. For the rhesus normal tissues, AR52A301.5 showed similar tissue specificity as observed in the corresponding human tissues for all of the tested organs (FIG. 29). It should be noted that rhesus normal tissue panel was smaller than what was tested for the cynomolgus. Based on the staining profiles, both the cynomolgus and rhesus monkey are considered to be suitable toxicology models for AR52A301.5.

EXAMPLE 14

AR52A301.5 Murine Sequence 1.0 Cloning Variable Region Genes Into Sequencing Vectors To facilitate production of antibody chimera, the genes encoding the variable regions of both heavy and light chains were separately cloned into the commercial sequencing vector pGEM-T easy (Promega Corp., Madison, Wis.).

1.1 Isolation of mRNA

Messenger ribonucleic acid (mRNA) was isolated from a culture of confluent Master Cell Bank (AR52A301.5) hybridoma cells using PolyA Tract System 1000 mRNA extraction kit (Promega Corp., Madison, Wis.). mRNA was stored at −80° C. until required for further use.

1.2 RT-PCR Amplification of Variable Region Genes

Separate reactions were carried out to amplify the light and heavy chain variable regions. Reverse transcriptase polymerase chain reaction (RT-PCR) synthesized complimentary deoxynucleic acid (cDNA) from the mRNA template and then specifically amplified the targeted gene.

For the light chain, 5.0 microliters of mRNA was mixed with 1.0 microliter of 20 pmol/microliter MuIgGKVL-3' primer OL040 and 5.5 microliters nuclease free water (Promega Corp., Madison, Wis.). For the lambda light chain, 5.0 microliters of mRNA was mixed with 1.0 microliter of 20 pmol/microliter MuIgG)VL-3' primer OL042 and 5.5 microliters nuclease free water (Promega Corp., Madison, Wis.). For the gamma heavy chain, 5 microliters of mRNA was mixed with 1.0 microliter of 20 pmol/microliter MuIgG$V_H$-3' primer OL023 and 5.5 microliters nuclease free water (Promega Corp., Madison, Wis.). All three reaction mixes were placed in the pre-heated block of the thermal cycler set at 70° C. for 5 minutes. The reaction mixes were then chilled on ice for 5 minutes before adding to each 4.0 microliters ImPrommII 5× reaction buffer (Promega Corp., Madison, Wis.), 0.5 microliters RNasin ribonuclease inhibitor (Promega Corp., Madison, Wis.), 2.0 microliters 25mM $MgCl_2$ (Promega Corp., Madison, Wis.), 1.0 microliter 10 mM dNTP mix (Promega Corp., Madison, Wis.) and 1.0 microliter Improm II reverse transcriptase (Promega Corp., Madison, Wis.). These reaction mixes were incubated at room temperature for 5 minutes before being transferred to a pre-heated PCR block set at 42° C. for 1 hour. After this time the reverse transcriptase was heat inactivated by incubating at 70° C. in a PCR block for fifteen minutes.

Heavy and light chain sequences were then specifically amplified using pools of primers (see FIG. 30 for primer sequences; SEQ ID NOS:9-46). The primer working solutions were made up as follows:

1. 5' single primer (MuIgV$_H$5'-A and B; MuIg?V$_L$h5'-A, B and C; MuIg?V$_L$5'-A) contained each primer at a concentration of 20 micromolar;
2. 5' primer pools (MuIgV$_H$5'-C to F; MuIg?V$_L$h5'-D to G) contained each constituent primer at a concentration of 5 micromolar.

Heavy and light chain sequences were amplified from cDNA. A PCR master mix was prepared by adding 37.5 microliters 10× Hi-Fi Expand PCR buffer (Roche, Mannheim, Germany), 7.5 microliters 10mM dNTP mix (Invitrogen, Paisley, UK) and 3.75 microliters Hi-Fi Expand DNA polymerase (Roche, Mannheim, Germany) to 273.75 microliters nuclease free water. This master mix was dispensed in 21.5 microliter aliquots into 15 thin walled PCR reaction tubes, on ice. Into six of these tubes was added 2.5 microliters of MUIgV$_H$-3' reverse transcription reaction mix and 1.0 microliters of heavy chain 5' primer mix A to F. To another seven tubes was added 2.5 microliters of MuIgκV$_L$-3' reverse transcripton reaction and 1.0 microliters of light chain 5' primer mixes A to G. Into the final tube was added 2.5 microliter of MuIgλV$_L$-3' reverse transcripton reaction and 1.0 microliters of lambda light chain primer MuIg?V$_L$5'-A. Reactions were placed in the block of the thermal cycler and heated to 95° C. for 2 minutes. The polymerase chain reaction (PCR) reaction was performed for 40 cycles of 94° C. for 30 seconds, 55° C. for 1 minute and 72° C. for 30 seconds. Finally the PCR products were heated at 72° C. for 5 minutes, and then stored at 4° C. PCR product was purified using QIAquick PCR Purification Kit (QIAGEN, Crawley, UK).

FIG. 31 shows the result of the RT-PCR reactions. The heavy chain reactions (lanes 2-7) demonstrate a strong band at 500 bp amplified using MuIgV$_H$5'-B (lane 3) and MuIgV$_H$5'-E (lane 6). Light chain reactions (lanes 8-15) demonstrate a strong 450 bp product band amplified using forward primer MuIgκV$_L$5'-G (lane 14). PCR products from these reactions were purified using QIAquick PCR Purification Kit (QIAGEN, Crawley, UK).

1.3 Cloning Into Sequencing Vectors

Light chain G and heavy chain B and E purified PCR products were separately cloned into pGEM-T easy vector using the pGEM-T easy Vector System I (Promega Corp., Madison, Wis.). Both the light and heavy chain reactions were prepared by adding 3.0 microliters of purified PCR product to 5.0 microliters of 2× ligation buffer, 1.0 microliters pGEM-T easy vector and 1.0 microliters T4 DNA ligase. Plasmids were transformed into sub-cloning grade XL1-blue competent E. coli (Stratgene, La Jolla, Calif.) as per the manufacturer's instructions. For all transformations, 2.0 microliters of the ligation reaction was used.

100 microliters of transformed cells from each reaction was plated on Luria broth (LB) agar (Q-Biogene, Cambridge, UK) plates containing 50 micrograms/mL ampicillin (Sigma, Poole, UK). The plates were inverted and incubated at 37° C. overnight.

Eight clones from each of the three plates were selected and used to inoculate 20 microliters sterile water. A PCR master mix was prepared by mixing 385.2 microliters sterile water, 25.5 microliters Dimethyl Sulphoximide (Sigma, Poole, UK), 51 microliters 10× Taq buffer (Invitrogen, Paisley, UK), 10.2 microliters 10 mM dNTP mix (Invitrogen, Paisley, UK), 5.1 microliters of 50 pmol/microliter primer OL001, 5.1 microliters of 50 pmol/microliter primer OL002 and 2.5 microliters Taq DNA polymerase (Invitrogen, Paisley, UK). This master mix was dispensed into 24 PCR reaction tubes in 19 microliter aliquots. Into each of these reaction tubes was added 1.0 microliter of the inoculated colony suspensions. PCR reactions were placed in the block of the thermal cycler and heated to 95° C. for 5 minutes. The polymerase chain reaction (PCR) reaction was performed for 25 cycles of 94° C. for 1 minute, 55° C. for 1 minute and 72° C. for 1 minute. Finally the PCR products were heated at 72° C. for 10 minutes. 5 microliters from each reaction was then run on a 1 percent agarose gel.

FIG. 32 shows the PCR screening reactions from eight colonies of AR52A301.5V$_H$-B and eight colonies of AR52A301.5V$_H$-E. Seven of the eight V$_H$B colonies, V$_H$B-2 to V$_H$B-8 (lanes 2-8) and one of the eight V$_H$-E colonies, V$_H$E-2 (lane 11) were positive for a 650 bp product band indicating the successful cloning of a 500 bp product into pGEM-T easy vector. The remaining V$_H$B and seven V$_H$-E reactions produced bands of a different molecular weight indicating a negative result for a 500 bp insert.

FIG. 32 also shows the PCR screening reactions from eight colonies of AR52A301.5V$_L$-G. Four of the eight V$_L$G colonies; V$_L$G-2, V$_L$G-5, V$_L$G-6 and V$_L$G-7 (lanes 19, 22, 23 and 24) were positive for a 600 bp product band indicating the successful cloning of a 450 bp product into pGEM-T easy vector. The remaining 4 V$_L$-G reactions produced bands of a different molecular weight indicating a negative result for a 450 bp insert.

A maximum of 4 positive colonies from each ligation were chosen to inoculate 5 mL of 2YT (Sigma, Poole, UK) broth containing 50 mg/L ampicillin (Sigma, Poole, UK). Cultures were incubated at 37° C. with shaking overnight. Plasmid DNA was extracted from each culture using Qiagen, QIAprep Spin Miniprep Kit (Qiagen, Crawley, UK).

1.4 DNA Sequencing

Plasmid DNA from nine AR52A301.5V$_L$ and V$_H$ clones (V$_L$G-2, V$_L$G-5, V$_L$G-6, V$_L$G-7, V$_H$B-2, V$_H$B-3, V$_H$B-4, V$_H$B-5 and V$_H$E-2) were sequenced at Geneservice Ltd. DNA sequencing facility (Cambridge, UK). Sequences are listed in FIGS. 33 and 34 with the complimentarity determining regions (CDRs) underlined. FIG. 33 shows SEQ ID NO:8 with the underlined CDRs designated SEQ ID NOS:4-6. FIG. 34 shows SEQ ID NO:7 with the underlined CDRs designated SEQ ID NOS: 1-3. CDR definitions and amino acid sequence numbering is done according to Kabat et al. (1991). The Kabat numbering is listed above the amino acid sequence in FIGS. 33 and 34. The hyphen in AR52A301.5 light chain CDR3 (FIG. 33) was inserted in order to match the Kabat numbering system.

The correct AR52A301.5V$_L$ sequence was found in all 4 of the clones amplified with 5' primer MuIgκV$_L$-G. The correct AR52A301.5V$_H$ sequence was found in all 4 of the clones amplified with 5' primer MuIgV$_H$-B. Sequences of products amplified with the 5' primer MuIgV$_H$-E did not align with murine IgG sequences.

EXAMPLE 15

Isolation of Competitive Binders

Given an antibody, an individual ordinarily skilled in the art can generate a competitively inhibiting CDMAB, for example a competing antibody, which is one that recognizes the same epitope (Belanger L et al. *Clinica Chimica Acta* 48:15-18 (1973)). One method entails immunizing with an immunogen that expresses the antigen recognized by the antibody. The sample may include but is not limited to tissues, isolated protein(s) or cell line(s). Resulting hybridomas could be screened using a competition assay, which is one that identifies antibodies that inhibit the binding of the test antibody, such as ELISA, FACS or Western blotting. Another method could make use of phage display antibody libraries and panning for antibodies that recognize at least one epitope of said antigen (Rubinstein J L et al. *Anal Biochem* 314:294-300 (2003)). In either case, antibodies are selected based on their ability to displace the binding of the original labeled antibody to at least one epitope of its target antigen. Such antibodies would therefore possess the characteristic of recognizing at least one epitope of the antigen as the original antibody.

EXAMPLE 16

Cloning of the Variable Regions of the AR52A301.5 Monoclonal Antibody

The sequences of the variable regions from the heavy (V$_H$) and light (V$_L$) chains of monoclonal antibody produced by the AR52A301.5 hybridoma cell line were determined (Example 14). To generate chimeric and humanized IgG, the variable light and variable heavy domains can be subcloned into an appropriate vector for expression.

In another embodiment, AR52A301.5 or its de-immunized, chimeric or humanized version is produced by expressing a nucleic acid encoding the antibody in a transgenic animal, such that the antibody is expressed and can be recovered. For example, the antibody can be expressed in a tissue specific manner that facilitates recovery and purification. In one such embodiment, an antibody of the invention is expressed in the mammary gland for secretion during lactation. Transgenic animals include but are not limited to mice, goat and rabbit.

(i) Monoclonal Antibody

DNA encoding the monoclonal antibody (as outlined in Example 1) is readily isolated and sequenced using conventional procedures (e.g., by using oligonucleotide probes that are capable of binding specifically to genes encoding the heavy and light chains of the monoclonal antibodies). The hybridoma cell serves as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences. Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

(ii) Humanized Antibody

A humanized antibody has one or more amino acid residues introduced into it from a non-human source. These non-human amino acid residues are often referred to as "import" residues, which are typically taken from an "import" variable domain. Humanization can be performed the method of Winter and co-workers by substituting rodent CDRs or CDR sequences for the corresponding sequences of a human antibody (Jones et al., Nature 321:522-525 (1986); Riechmann et al., Nature 332:323-327 (1988); Verhoeyen et al., Science 239:1534-1536 (1988); reviewed in Clark, Immunol. Today 21:397-402 (2000)).

A humanized antibody can be prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

(iii) Antibody Fragments

Various techniques have been developed for the production of antibody fragments. These fragments can be produced by recombinant host cells (reviewed in Hudson, Curr. Opin. Immunol. 11:548-557 (1999); Little et al., Immunol. Today 21:364-370 (2000)). For example, Fab'-SH fragments can be directly recovered from E. coli and chemically coupled to form $F(ab')_2$ fragments (Carter et al., Biotechnology 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture.

EXAMPLE 17

A Composition Comprising the Antibody of the Present Invention

The antibody of the present invention can be used as a composition for preventing/treating cancer. The composition for preventing/treating cancer, which comprises the antibody of the present invention, are low-toxic and can be administered as they are in the form of liquid preparations, or as pharmaceutical compositions of suitable preparations to human or mammals (e.g., rats, rabbits, sheep, swine, bovine, feline, canine, simian, etc.) orally or parenterally (e.g., intravascularly, intraperitoneally, subcutaneously, etc.). The antibody of the present invention may be administered in itself, or may be administered as an appropriate composition. The composition used for the administration may contain a pharmacologically acceptable carrier with the antibody of the present invention or its salt, a diluent or excipient. Such a composition is provided in the form of pharmaceutical preparations suitable for oral or parenteral administration.

Examples of the composition for parenteral administration are injectable preparations, suppositories, etc. The injectable preparations may include dosage forms such as intravenous, subcutaneous, intracutaneous and intramuscular injections, drip infusions, intraarticular injections, etc. These injectable preparations may be prepared by methods publicly known. For example, the injectable preparations may be prepared by dissolving, suspending or emulsifying the antibody of the present invention or its salt in a sterile aqueous medium or an oily medium conventionally used for injections. As the aqueous medium for injections, there are, for example, physiological saline, an isotonic solution containing glucose and other auxiliary agents, etc., which may be used in combination with arm appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mols) adduct of hydrogenated castor oil)), etc. As the oily medium, there are employed, e.g., sesame oil, soybean oil, etc., which may be used in combination with a solubilizing agent such as benzyl benzoate, benzyl alcohol, etc. The injection thus prepared is usually filled in an appropriate ampoule. The suppository used for rectal administration may be prepared by blending the antibody of the present invention or its salt with conventional bases for suppositories. The composition for oral administration includes solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and may contain a vehicle, a diluent or excipient conventionally used in the field of pharmaceutical preparations. Examples of the vehicle or excipient for tablets are lactose, starch, sucrose, magnesium stearate, etc.

Advantageously, the compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the aforesaid compound contained is generally 5 to 500 mg per dosage unit form; it is preferred that the antibody described above is contained in about 5 to about 100 mg especially in the form of injection, and in 10 to 250 mg for the other forms.

The dose of the aforesaid prophylactic/therapeutic agent or regulator comprising the antibody of the present invention may vary depending upon subject to be administered, target disease, conditions, route of administration, etc. For example, when used for the purpose of treating/preventing, e.g., breast cancer in an adult, it is advantageous to administer the antibody of the present invention intravenously in a dose of about 0.01 to about 20 mg/kg body weight, preferably about 0.1 to about 10 mg/kg body weight and more preferably about 0.1 to about 5 mg/kg body weight, about 1 to 5 times/day, preferably about 1 to 3 times/day. In other parenteral and oral administration, the agent can be administered in a dose corresponding to the dose given above. When the condition is especially severe, the dose may be increased according to the condition.

The antibody of the present invention may be administered as it stands or in the form of an appropriate composition. The composition used for the administration may contain a pharmacologically acceptable carrier with the aforesaid antibody or its salts, a diluent or excipient. Such a composition is provided in the form of pharmaceutical preparations suitable for oral or parenteral administration (e.g., intravascular injection, subcutaneous injection, etc.). Each composition described above may further contain other active ingredients. Furthermore, the antibody of the present invention may be used in combination with other drugs, for example, alkylating agents (e.g., cyclophosphamide, ifosfamide, etc.), metabolic antagonists (e.g., methotrexate, 5-fluorouracil, etc.), anti-tumor antibiotics (e.g., mitomycin, adriamycin, etc.), plant-derived anti-tumor agents (e.g., vincristine, vindesine, Taxol®, etc.), cisplatin, carboplatin, etoposide, irinotecan, etc. The antibody of the present invention and the drugs described above may be administered simultaneously or at staggered times to the patient.

The method of treatment described herein, particularly for cancers, may also be carried out with administration of other antibodies or chemotherapeutic agents. For example, an antibody against EGFR, such as ERBITUX® (cetuximab), may also be administered, particularly when treating colon cancer. ERBITUX® has also been shown to be effective for treatment of psoriasis. Other antibodies for combination use include Herceptin® (trastuzumab) particularly when treating breast cancer, AVASTIN® particularly when treating colon cancer and SGN-15 particularly when treating non-small cell lung cancer. The administration of the antibody of the present invention with other antibodies/chemotherapeutic agents may occur simultaneously, or separately, via the same or different route.

The chemotherapeutic agent/other antibody regimens utilized include any regimen believed to be optimally suitable for the treatment of the patient's condition. Different malignancies can require use of specific anti-tumor antibodies and specific chemotherapeutic agents, which will be determined on a patient to patient basis. In a preferred embodiment of the invention, chemotherapy is administered concurrently with or, more preferably, subsequent to antibody therapy. It should be emphasized, however, that the present invention is not limited to any particular method or route of administration.

The preponderance of evidence shows that AR52A301.5 mediate anti-cancer effects and prolongs survival through ligation of epitopes present on TROP-2. It has been shown, in Examples 8 and 9 that AR52A301.5 antibodies can be used to immunoprecipitate the cognate antigen from expressing cells such as MDA-MB-231 cells. Further it has been shown, in Examples 1, 2 and 11-13 that the AR52A301.5 antibody could be used in detection of cells and/or tissues which express a TROP-2 antigenic moiety which specifically binds thereto, utilizing techniques illustrated by, but not limited to FACS, cell ELISA or IHC.

Thus, it could be shown that the immunoprecipitated AR52A301.5 antigen can inhibit the binding of AR52A301.5 to such cells or tissues using FACS, cell ELISA or IHC assays. Further, as with the AR52A301.5 antibody, other anti-TROP-2 antibodies could be used to immunoprecipitate and isolate other forms of the TROP-2 antigen, and the antigen can also be used to inhibit the binding of those antibodies to the cells or tissues that express the antigen using the same types of assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated monoclonal antibody produced by the hybridoma cell line AR52A301.5 deposited with the IDAC as accession number 141205-03.

2. The isolated hybridoma cell line AR52A301.5 deposited with the IDAC as accession number 141205-03.

3. A conjugate of the isolated antibody of claim 1 or an antigen-binding fragment thereof and a member selected from the group consisting of a cytotoxic moiety, an enzyme, a radioactive compound, a cytokine, an interferon, a target moiety and a reporter moiety.

4. An antibody or an antigen-binding fragment thereof that specifically binds the same antigen as the isolated monoclonal antibody produced by the hybridoma cell line AR52A301.5 having IDAC Accession No. 141205-03, wherein said antibody or said antigen-binding fragment thereof comprises: a heavy chain variable region comprising the complementarity determining region amino acid sequences of SEQ ID NO: 1, SEQ ID NO: 2, and SEQ ID NO: 3; and a light chain variable region comprising the complementarity determining region amino acid sequences of SEQ ID NO:4, SEQ ID NO:5, and SEQ ID NO:6.

5. An antibody or an antigen-binding fragment thereof that specifically binds the same antigen as the isolated monoclonal antibody produced by the hybridoma cell line AR52A301.5 having IDAC Accession No. 141205-03, wherein said antibody or said antigen-binding fragment thereof comprises: a heavy chain variable region comprising the complementarity determining region amino acid sequences of SEQ ID NO:1, SEQ ID NO:2, and SEQ ID NO:3; a light chain variable region comprising the complementarity determining region amino acid sequences of SEQ ID NO:4, SEQ ID NO:5, and SEQ ID NO:6; and variable domain framework regions from the heavy and light chains of a human antibody or human antibody consensus framework.

6. An antibody or an antigen-binding fragment thereof that specifically binds the same antigen as the isolated monoclonal antibody produced by the hybridoma cell line AR52A301.5 having IDAC Accession No. 141205-03, wherein said antibody or said antigen-binding fragment thereof comprises a heavy chain variable region amino acid sequence of SEQ ID NO:7; and a light chain variable region amino acid sequence of SEQ ID NO:8.

7. The antibody of any one of claims 4, 5 and 6 or an antigen-binding fragment thereof conjugated to a member selected from the group consisting of a cytotoxic moiety, an enzyme, a radioactive compound, a cytokine, an interferon, a target moiety and a reporter moiety.

8. A composition comprising:
   (a) the antibody of any one claims 1, 4, 5, and 6; and
   (b) a pharmaceutically acceptable carrier.

9. A composition comprising:
   (a) a conjugate of the antibody of any one of claims 1, 4, 5, and 6 and a member selected from the group consisting of a cytotoxic moiety, an enzyme, a radioactive compound, a cytokine, an interferon, a target moiety and a reporter moiety; and
   (b) a pharmacuetically acceptable carrier.

* * * * *

SEQUENCE LISTING

<160> NUMBER OF SEQ ID NOS: 46

<210> SEQ ID NO 1
<211> LENGTH: 5
<212> TYPE: PRT
<213> ORGANISM: Homo sapiens

```
<400> SEQUENCE: 1

Asp Tyr Asn Met His
1               5

<210> SEQ ID NO 2
<211> LENGTH: 17
<212> TYPE: PRT
<213> ORGANISM: Homo sapiens

<400> SEQUENCE: 2

Tyr Ile Tyr Pro Tyr Asn Gly Gly Thr Gly Tyr Asn Gln Phe Arg Lys
1               5                   10                  15

Asn

<210> SEQ ID NO 3
<211> LENGTH: 9
<212> TYPE: PRT
<213> ORGANISM: Homo sapiens

<400> SEQUENCE: 3

Glu Glu Asp Tyr Tyr Gly Phe Asp Tyr
1               5

<210> SEQ ID NO 4
<211> LENGTH: 16
<212> TYPE: PRT
<213> ORGANISM: Homo sapiens

<400> SEQUENCE: 4

Arg Ser Ser Gln Ser Leu Val His Ser Tyr Gly Asn Thr Tyr Leu His
1               5                   10                  15

<210> SEQ ID NO 5
<211> LENGTH: 7
<212> TYPE: PRT
<213> ORGANISM: Homo sapiens

<400> SEQUENCE: 5

Lys Val Ser Asn Arg Phe Ser
1               5

<210> SEQ ID NO 6
<211> LENGTH: 8
<212> TYPE: PRT
<213> ORGANISM: Homo sapiens

<400> SEQUENCE: 6

Ser Gln Ser Thr His Val Tyr Thr
1               5

<210> SEQ ID NO 7
<211> LENGTH: 118
<212> TYPE: PRT
<213> ORGANISM: Homo sapiens

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45
```

-continued

```
Gly Tyr Ile Tyr Pro Tyr Asn Gly Gly Thr Gly Tyr Asn Gln Arg Phe
            50                  55                  60
Lys Asn Lys Ala Thr Leu Thr Val Asp Ile Ser Ser Ser Thr Ala Tyr
 65                  70                  75                  80
Met Glu Leu Arg Ser Leu Thr Ser Glu Asp Ser Ala Val Tyr Tyr Cys
                 85                  90                  95
Ala Arg Glu Glu Asp Tyr Tyr Gly Phe Asp Tyr Trp Gly Gln Gly Thr
            100                 105                 110
Thr Leu Thr Val Ser Ser
            115

<210> SEQ ID NO 8
<211> LENGTH: 111
<212> TYPE: PRT
<213> ORGANISM: Homo sapiens

<400> SEQUENCE: 8

Asp Val Val Met Thr Gln Thr Pro Leu Ser Leu Pro Val Ser Leu Gly
  1               5                  10                  15
Gln Asp Ala Ser Ile Ser Cys Arg Ser Ser Gln Ser Leu Val His Ser
             20                  25                  30
Tyr Gly Asn Thr Tyr Leu His Trp Tyr Leu Gln Lys Pro Gly Gln Ser
             35                  40                  45
Pro Lys Leu Leu Ile Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Met Gly Val Tyr Phe Cys Ser Gln Ser
                 85                  90                  95
Thr His Val Tyr Thr Phe Gly Gly Gly Thr Lys Leu Glu Ile Lys
            100                 105                 110

<210> SEQ ID NO 9
<211> LENGTH: 24
<212> TYPE: DNA
<213> ORGANISM: Artificial
<220> FEATURE:
<223> OTHER INFORMATION: primer sequence used for PCR

<400> SEQUENCE: 9
cgccagggtt ttcccagtca cgac                                              24

<210> SEQ ID NO 10
<211> LENGTH: 24
<212> TYPE: DNA
<213> ORGANISM: Artificial
<220> FEATURE:
<223> OTHER INFORMATION: primer sequence used for PCR

<400> SEQUENCE: 10
agcggataac aatttcacac agga                                              24

<210> SEQ ID NO 11
<211> LENGTH: 25
<212> TYPE: DNA
<213> ORGANISM: Artificial
<220> FEATURE:
<223> OTHER INFORMATION: primer sequence used for PCR
```

<400> SEQUENCE: 11
atgrasttsk ggytmarctk grttt       25

<210> SEQ ID NO 12
<211> LENGTH: 26
<212> TYPE: DNA
<213> ORGANISM: Artificial
<220> FEATURE:
<223> OTHER INFORMATION: primer sequence used for PCR

<400> SEQUENCE: 12
atgraatgsa sctgggtywt yctctt       26

<210> SEQ ID NO 13
<211> LENGTH: 29
<212> TYPE: DNA
<213> ORGANISM: Artificial
<220> FEATURE:
<223> OTHER INFORMATION: primer sequence used for PCR

<400> SEQUENCE: 13
atggactcca ggctcaattt agttttcct       29

<210> SEQ ID NO 14
<211> LENGTH: 26
<212> TYPE: DNA
<213> ORGANISM: Artificial
<220> FEATURE:
<223> OTHER INFORMATION: primer sequence used for PCR

<400> SEQUENCE: 14
atggctgtcy trgbgctgyt cytctg       26

<210> SEQ ID NO 15
<211> LENGTH: 29
<212> TYPE: DNA
<213> ORGANISM: Artificial
<220> FEATURE:
<223> OTHER INFORMATION: primer sequence used for PCR

<400> SEQUENCE: 15
atggvttggs tgtggamctt gcyattcct       29

<210> SEQ ID NO 16
<211> LENGTH: 26
<212> TYPE: DNA
<213> ORGANISM: Artificial
<220> FEATURE:
<223> OTHER INFORMATION: primer sequence used for PCR

<400> SEQUENCE: 16
atgaaatgca gctggrtyat sttctt       26

<210> SEQ ID NO 17
<211> LENGTH: 26
<212> TYPE: DNA
<213> ORGANISM: Artificial
<220> FEATURE:
<223> OTHER INFORMATION: primer sequence used for PCR

<400> SEQUENCE: 17
atggrcagrc ttacwtyytc attcct       26

```
<210> SEQ ID NO 18
<211> LENGTH: 26
<212> TYPE: DNA
<213> ORGANISM: Artificial
<220> FEATURE:
<223> OTHER INFORMATION: primer sequence used for PCR

<400> SEQUENCE: 18
atgatggtgt taagtcttct gtacct                                    26

<210> SEQ ID NO 19
<211> LENGTH: 26
<212> TYPE: DNA
<213> ORGANISM: Artificial
<220> FEATURE:
<223> OTHER INFORMATION: primer sequence used for PCR

<400> SEQUENCE: 19
atgggatgga gctrtatcat sytctt                                    26

<210> SEQ ID NO 20
<211> LENGTH: 23
<212> TYPE: DNA
<213> ORGANISM: Artificial
<220> FEATURE:
<223> OTHER INFORMATION: primer sequence used for PCR

<400> SEQUENCE: 20
atgaagwtgt ggbtraactg grt                                       23

<210> SEQ ID NO 21
<211> LENGTH: 25
<212> TYPE: DNA
<213> ORGANISM: Artificial
<220> FEATURE:
<223> OTHER INFORMATION: primer sequence used for PCR
<220> FEATURE:
<221> NAME/KEY: misc_feature
<223> OTHER INFORMATION: "n" at position 15  represents an unknown
      nucleotide
<220> FEATURE:
<221> NAME/KEY: misc_feature
<222> LOCATION: (15)..(15)
<223> OTHER INFORMATION: n is a, c, g, or t

<400> SEQUENCE: 21
atggratgga sckknrtctt tmtct                                     25

<210> SEQ ID NO 22
<211> LENGTH: 25
<212> TYPE: DNA
<213> ORGANISM: Artificial
<220> FEATURE:
<223> OTHER INFORMATION: primer sequence used for PCR

<400> SEQUENCE: 22
atgaacttyg ggytsagmtt grttt                                     25

<210> SEQ ID NO 23
<211> LENGTH: 25
<212> TYPE: DNA
<213> ORGANISM: Artificial
<220> FEATURE:
<223> OTHER INFORMATION: primer sequence used for PCR

<400> SEQUENCE: 23
atgtacttgg gactgagctg tgtat                                     25
```

<210> SEQ ID NO 24
<211> LENGTH: 23
<212> TYPE: DNA
<213> ORGANISM: Artificial
<220> FEATURE:
<223> OTHER INFORMATION: primer sequence used for PCR

<400> SEQUENCE: 24
atgagagtgc tgattctttt gtg                                           23

<210> SEQ ID NO 25
<211> LENGTH: 28
<212> TYPE: DNA
<213> ORGANISM: Artificial
<220> FEATURE:
<223> OTHER INFORMATION: primer sequence used for PCR

<400> SEQUENCE: 25
atggattttg ggctgatttt ttttattg                                      28

<210> SEQ ID NO 26
<211> LENGTH: 23
<212> TYPE: DNA
<213> ORGANISM: Artificial
<220> FEATURE:
<223> OTHER INFORMATION: primer sequence used for PCR

<400> SEQUENCE: 26
acgaggggga agacatttgg gaa                                           23

<210> SEQ ID NO 27
<211> LENGTH: 26
<212> TYPE: DNA
<213> ORGANISM: Artificial
<220> FEATURE:
<223> OTHER INFORMATION: primer sequence used for PCR
<220> FEATURE:
<221> NAME/KEY: misc_feature
<223> OTHER INFORMATION: "n" at position 21 represents an unknown
      nucleotide
<220> FEATURE:
<221> NAME/KEY: misc_feature
<222> LOCATION: (21)..(21)
<223> OTHER INFORMATION: n is a, c, g, or t

<400> SEQUENCE: 27
ccagggrcca rkggatarac ngrtgg                                        26

<210> SEQ ID NO 28
<211> LENGTH: 24
<212> TYPE: DNA
<213> ORGANISM: Artificial
<220> FEATURE:
<223> OTHER INFORMATION: primer sequence used for PCR

<400> SEQUENCE: 28
atgragwcac akwcycaggt cttt                                          24

<210> SEQ ID NO 29
<211> LENGTH: 25
<212> TYPE: DNA
<213> ORGANISM: Artificial
<220> FEATURE:
<223> OTHER INFORMATION: primer sequence used for PCR

<400> SEQUENCE: 29
atggagacag acacactcct gctat                                         25

```
<210> SEQ ID NO 30
<211> LENGTH: 29
<212> TYPE: DNA
<213> ORGANISM: Artificial
<220> FEATURE:
<223> OTHER INFORMATION: primer sequence used for PCR

<400> SEQUENCE: 30
atggagwcag acacactsct gytatgggt                                      29

<210> SEQ ID NO 31
<211> LENGTH: 32
<212> TYPE: DNA
<213> ORGANISM: Artificial
<220> FEATURE:
<223> OTHER INFORMATION: primer sequence used for PCR
<220> FEATURE:
<221> NAME/KEY: misc_feature
<223> OTHER INFORMATION: "n" at position 27 represents an unknown
      nucleotide
<220> FEATURE:
<221> NAME/KEY: misc_feature
<222> LOCATION: (27)..(27)
<223> OTHER INFORMATION: n is a, c, g, or t

<400> SEQUENCE: 31
atgaggrccc ctgctcagwt tyttggnwtc tt                                  32

<210> SEQ ID NO 32
<211> LENGTH: 31
<212> TYPE: DNA
<213> ORGANISM: Artificial
<220> FEATURE:
<223> OTHER INFORMATION: primer sequence used for PCR

<400> SEQUENCE: 32
atgggcwtca agatgragtc acakwyycwg g                                   31

<210> SEQ ID NO 33
<211> LENGTH: 29
<212> TYPE: DNA
<213> ORGANISM: Artificial
<220> FEATURE:
<223> OTHER INFORMATION: primer sequence used for PCR

<400> SEQUENCE: 33
atgagtgtgc ycactcaggt cctggsgtt                                      29

<210> SEQ ID NO 34
<211> LENGTH: 31
<212> TYPE: DNA
<213> ORGANISM: Artificial
<220> FEATURE:
<223> OTHER INFORMATION: primer sequence used for PCR

<400> SEQUENCE: 34
atgtggggay cgktttyamm cttttcaatt g                                   31

<210> SEQ ID NO 35
<211> LENGTH: 28
<212> TYPE: DNA
<213> ORGANISM: Artificial
<220> FEATURE:
<223> OTHER INFORMATION: primer sequence used for PCR

<400> SEQUENCE: 35
atggaagccc cagctcagct tctcttcc                                       28
```

```
<210> SEQ ID NO 36
<211> LENGTH: 26
<212> TYPE: DNA
<213> ORGANISM: Artificial
<220> FEATURE:
<223> OTHER INFORMATION: primer sequence used for PCR
<220> FEATURE:
<221> NAME/KEY: misc_feature
<223> OTHER INFORMATION: "n" at positions 6, 12 and 18 represents
      unknown nucleotides.
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 36
atgagnmmkt cnmttcantt cytggg                                         26

<210> SEQ ID NO 37
<211> LENGTH: 26
<212> TYPE: DNA
<213> ORGANISM: Artificial
<220> FEATURE:
<223> OTHER INFORMATION: primer sequence used for PCR
<220> FEATURE:
<221> NAME/KEY: misc_feature
<223> OTHER INFORMATION: "n" at positions 12 and 24 represents unknown
      nucleotides
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 37
atgakgthcy cngctcagyt yctnrg                                         26

<210> SEQ ID NO 38
<211> LENGTH: 25
<212> TYPE: DNA
<213> ORGANISM: Artificial
<220> FEATURE:
<223> OTHER INFORMATION: primer sequence used for PCR

<400> SEQUENCE: 38
atggtrtccw casctcagtt ccttg                                          25

<210> SEQ ID NO 39
<211> LENGTH: 27
<212> TYPE: DNA
<213> ORGANISM: Artificial
<220> FEATURE:
<223> OTHER INFORMATION: primer sequence used for PCR

<400> SEQUENCE: 39
atgtatatat gtttgttgtc tatttct                                        27
```

<210> SEQ ID NO 40
<211> LENGTH: 29
<212> TYPE: DNA
<213> ORGANISM: Artificial
<220> FEATURE:
<223> OTHER INFORMATION: primer sequence used for PCR

<400> SEQUENCE: 40
atgaagttgc ctgttaggct gttggtgct                              29

<210> SEQ ID NO 41
<211> LENGTH: 29
<212> TYPE: DNA
<213> ORGANISM: Artificial
<220> FEATURE:
<223> OTHER INFORMATION: primer sequence used for PCR

<400> SEQUENCE: 41
atggatttwc argtgcagat twtcagctt                              29

<210> SEQ ID NO 42
<211> LENGTH: 27
<212> TYPE: DNA
<213> ORGANISM: Artificial
<220> FEATURE:
<223> OTHER INFORMATION: primer sequence used for PCR

<400> SEQUENCE: 42
atggtyctya tvtccttgct gttctgg                                27

<210> SEQ ID NO 43
<211> LENGTH: 27
<212> TYPE: DNA
<213> ORGANISM: Artificial
<220> FEATURE:
<223> OTHER INFORMATION: primer sequence used for PCR

<400> SEQUENCE: 43
atggtyctya tvttrctgct gctatgg                                27

<210> SEQ ID NO 44
<211> LENGTH: 21
<212> TYPE: DNA
<213> ORGANISM: Artificial
<220> FEATURE:
<223> OTHER INFORMATION: primer sequence used for PCR

<400> SEQUENCE: 44
actggatggt gggaagatgg a                                      21

<210> SEQ ID NO 45
<211> LENGTH: 25
<212> TYPE: DNA
<213> ORGANISM: Artificial
<220> FEATURE:
<223> OTHER INFORMATION: primer sequence used for PCR

<400> SEQUENCE: 45
atggcctgga ytycwctywt mytct                                  25

<210> SEQ ID NO 46
<211> LENGTH: 23
<212> TYPE: DNA
<213> ORGANISM: Artificial
<220> FEATURE:
<223> OTHER INFORMATION: primer sequence used for PCR

```
-continued

<220> FEATURE:
<221> NAME/KEY: misc_feature
<223> OTHER INFORMATION: "n" at position 15 represents an unknown
      nucleotide
<220> FEATURE:
<221> NAME/KEY: misc_feature
<222> LOCATION: (15)..(15)
<223> OTHER INFORMATION: n is a, c, g, or t

<400> SEQUENCE: 46
agctcytcwg wgganggygg raa                                             23
```